(12) United States Patent
Betley et al.

(10) Patent No.: US 9,724,682 B2
(45) Date of Patent: Aug. 8, 2017

(54) SYNTHESIS OF ACYCLIC AND CYCLIC AMINES USING IRON-CATALYZED NITRENE GROUP TRANSFER

(71) Applicant: President and Fellows of Harvard College, Cambridge, MA (US)

(72) Inventors: Theodore Alexander Betley, Cambridge, MA (US); Elisabeth Therese Hennessy, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/345,266

(22) Filed: Nov. 7, 2016

(65) Prior Publication Data

US 2017/0072390 A1   Mar. 16, 2017

Related U.S. Application Data

(62) Division of application No. 14/770,217, filed as application No. PCT/US2014/018623 on Feb. 26, 2014, now Pat. No. 9,487,472.

(60) Provisional application No. 61/769,469, filed on Feb. 26, 2013.

(51) Int. Cl.

| | | |
|---|---|---|
| *C07D 263/04* | (2006.01) | |
| *C07D 211/16* | (2006.01) | |
| *C07D 209/54* | (2006.01) | |
| *C07D 207/06* | (2006.01) | |
| *C07D 207/16* | (2006.01) | |
| *C07D 205/04* | (2006.01) | |
| *B01J 31/22* | (2006.01) | |
| *C07C 209/02* | (2006.01) | |
| *C07F 15/02* | (2006.01) | |
| *C07D 263/06* | (2006.01) | |

(52) U.S. Cl.
CPC ......... *B01J 31/2273* (2013.01); *C07C 209/02* (2013.01); *C07D 205/04* (2013.01); *C07D 207/06* (2013.01); *C07D 207/16* (2013.01); *C07D 209/54* (2013.01); *C07D 211/16* (2013.01); *C07D 263/04* (2013.01); *C07D 263/06* (2013.01); *C07F 15/025* (2013.01); *C07C 2101/10* (2013.01); *C07C 2101/14* (2013.01); *C07C 2101/16* (2013.01); *C07C 2101/18* (2013.01); *C07C 2103/74* (2013.01)

(58) Field of Classification Search
CPC .. C07D 263/04; C07D 211/16; C07D 209/54; C07D 207/06; C07D 207/16; C07D 205/04; B01J 31/2273; C07C 209/02; C07C 2101/10; C07C 209/16; C07C 209/18; C07C 2103/74; C07F 15/025
See application file for complete search history.

(56) References Cited

U.S. PATENT DOCUMENTS

| | | |
|---|---|---|
| 9,487,472 B2 | 11/2016 | Betley et al. |
| 2010/0056806 A1 | 3/2010 | Warren |

OTHER PUBLICATIONS

Hennessy, et al., Complex N-Heterocycle Synthesis via Iron-Catalyzed, Direct C—H Bond Amination, Science, vol. 340 (May 3, 2013).*
Invitation to Pay Additional fees, mailed May 27, 2014, in connection with Application No. PCT/US2014/018623.
International Search Report and Written Opinion, mailed Aug. 5, 2014, in connection with Application No. PCT/US2014/018623.
International Preliminary Report on Patentability, mailed Sep. 11, 2015, in connection with Application No. PCT/US2014/018623.
Au et al., Aziridination of Alkenes and Amidation of Alkanes by Bis(tosylimido)ruthenium(VI) Porphyrins. A Mechanistic Study. J Am Chem Soc. Sep. 18, 1999;121(39):9120-9132. doi: 10.1021/ja9913481.
Badiei et al., Copper-nitrene complexes in catalytic C—H amination. Angew Chem Int Ed Engl. 2008;47(51):9961-4. doi: 10.1002/anie.200804304.
Bart et al., Synthesis and hydrogenation of bis(imino)pyridine iron imides. J Am Chem Soc. Apr. 26, 2006;128(16):5302-3.
Bergman, Organometallic chemistry: C-H activation. Nature. Mar. 22, 2007;446(7134):391-3. Erratum in: Nature. Mar. 29, 2007;446(7135):506.
Bernasconi et al., The Role of Equatorial and Axial Ligands in Promoting the Activity of NonHeme Oxidoiron(IV) Catalysts in Alkane Hydroxylation. Eur J Inorg Chem. Jul. 2007;2007(19):3023-3033. doi: 10.1002/ejic.200601238.
Betley et al., Dinitrogen chemistry from trigonally coordinated iron and cobalt platforms. J Am Chem Soc. Sep. 10, 2003;125(36):10782-3.
Brown et al., A low-spin d5 iron imide: nitrene capture by low-coordinate iron(I) provides the 4-coordinate Fe(III) complex [PhB(CH2PPh2)3]Fe=N-p-tolyl. J Am Chem Soc. Jan. 15, 2003;125(2):322-3.
Brown et al., Ground-state singlet L3Fe-(mu-N)-FeL3 and L3Fe(NR) complexes featuring pseudotetrahedral Fe(II) centers. J Am Chem Soc. Feb. 16, 2005;127(6):1913-23.
Cenini et al., Coordination chemistry of organic azides and amination reactions catalyzed by transition metal complexes. Coord Chem Rev. Jun. 2006;250(11-12):1234-1253.

(Continued)

*Primary Examiner* — Erich A Leeser
(74) *Attorney, Agent, or Firm* — Wolf, Greenfield & Sacks, P.C.

(57) ABSTRACT

The present invention provides novel synthetic methods for making acyclic secondary amines by reacting an azide with a compound bearing one or more C—H groups, catalyzed by a $Fe^{II}$-dipyrromethene complex. The acyclic secondary amines are thought to be formed through an intermolecular nitrene transfer. Also provided herein are methods of synthesizing protected (e.g., Boc- or Fmoc-protected) cyclic secondary amines (e.g., 5-, 6-, and 7-membered cyclic secondary amines) by reacting an azide that bears one or more C—H groups, catalyzed by a $Fe^{II}$-dipyrromethene complex. The protected cyclic secondary amines are thought to be formed through an intramolecular nitrene transfer and may be subsequently deprotected to yield cyclic secondary amines.

20 Claims, 10 Drawing Sheets

(56) References Cited

OTHER PUBLICATIONS

Collet et al., Catalytic C—H amination: recent progress and future directions. Chem Commun (Camb). Sep. 14, 2009;(34):5061-74. doi: 10.1039/b905820f. Epub Jul. 7, 2009.

Corey et al., A general, catalytic, and enantioselective synthesis of .alpha.-amino acids. J Am Chem Soc. 1992;114(5):1906-1908. doi: 10.1021/ja00031a069.

Cowley et al., Catalytic nitrene transfer from an imidoiron(III) complex to form carbodiimides and isocyanates. Chem Commun (Camb). Apr. 7, 2009;(13):1760-2. doi: 10.1039/b820620a. Epub Feb. 17, 2009.

Cowley et al., C—H activation by a terminal imidoiron(III) complex to form a cyclopentadienyliron(II) product. Inorganica Chimica Acta. Apr. 15, 2011;369(1):40-44.

Cowley et al., Three-coordinate terminal imidoiron(III) complexes: structure, spectroscopy, and mechanism of formation. Inorg Chem. Jul. 5, 2010;49(13):6172-87. doi: 10.1021/ic100846b.

Davies et al., Catalytic C—H functionalization by metal carbenoid and nitrenoid insertion. Nature. Jan. 24, 2008;451(7177):417-24. doi: 10.1038/nature06485.

Davies et al., Recent advances in catalytic intramolecular C—H aminations. Angew Chem Int Ed Engl. Jun. 6, 2005;44(23):3518-20.

Decker et al., Spectroscopic and quantum chemical studies on low-spin FeIV=O complexes: Fe—O bonding and its contributions to reactivity. J Am Chem Soc. Dec. 26, 2007;129(51):15983-96. Epub Dec. 5, 2007.

Dick et al., Transition metal catalyzed oxidative functionalization of carbon-hydrogen bonds. Tetrahedron. Mar. 13, 2006;62(11):2439-2463.

Drouin et al., Thermolyse et photolyse de cetones non saturees—XXVII : Synthese de composes bicycliques par double thermocyclisation de dienones et de dienediones. Tetrahedron. 1980;36(9):1195-1201.

Halfen, Recent Advances in Metal-Mediated Carbon-Nitrogen Bond Formation Reactions: Aziridination and Amidation. Curr Org Chem. 2005;9(7):657-669. doi: 10.2174/1385272053765024.

Hennessy et al., Iron-mediated intermolecular N-group transfer chemistry with olefinic substrates. Chemical Science. 2014;5(4):1526-1532. doi: 10.1039/C3SC52533C.

King et al., Catalytic C—H bond amination from high-spin iron imido complexes. J Am Chem Soc. Apr. 6, 2011;133(13):4917-23. doi: 10.1021/ja110066j. Epub Mar. 15, 2011.

King et al., C—H bond amination from a ferrous dipyrromethene complex. Inorg Chem. Mar. 16, 2009;48(6):2361-3. doi: 10.1021/ic900219b.

Krebs et al., Non-heme Fe(IV)-oxo intermediates. Acc Chem Res. Jul. 2007;40(7):484-92. Epub Jun. 2, 2007.

Labinger et al., Understanding and exploiting C—H bond activation. Nature. May 30, 2002;417(6888):507-14.

Laskowski et al., A two-coordinate nickel imido complex that effects C—H amination. J Am Chem Soc. Feb. 2, 2011;133(4):771-3. doi: 10.1021/ja101213.

Lu et al., Fe(I)-mediated reductive cleavage and coupling of CO(2): an Fe(II)(mu-O, mu-CO)Fe(II) core. J Am Chem Soc. Jan. 10, 2007;129(1):4-5.

Lyaskovskyy et al., Mechanism of cobalt(II) porphyrin-catalyzed C—H amination with organic azides: radical nature and H-atom abstraction ability of the key cobalt(III)-nitrene intermediates. J Am Chem Soc. Aug. 10, 2011;133(31):12264-73. doi: 10.1021/ja204800a. Epub Jul. 18, 2011.

Müller et al., Enantioselective catalytic aziridinations and asymmetric nitrene insertions into CH bonds. Chem Rev. Aug. 2003;103(8):2905-20.

Ni et al., Reaction of a sterically encumbered iron(I) aryllarene with organoazides: formation of an iron(V) bis(imide). Chem Commun (Camb). Dec. 7, 2008;(45):6045-7. doi: 10.1039/b810941a. Epub Oct. 21, 2008.

Nieto et al., Thermodynamics of hydrogen atom transfer to a high-valent iron imido complex. J Am Chem Soc. Mar. 5, 2008;130(9):2716-7. doi: 10.1021/ja0776834. Epub Feb. 12, 2008.

Osborn et al., The asymmetric synthesis of aziridines. Tetrahedron: Asymmetry. Jun. 12, 1997;8(11):1693-1715.

Powers et al., Oxidative group transfer to a triiron complex to form a nucleophilic μ(3)-nitride, [Fe3(μ(3)-N)]-. J Am Chem Soc. Mar. 16, 2011;133(10):3336-8. doi: 10.1021/ja2003445. Epub Feb. 18, 2011.

Ryabov, Mechanisms of intramolecular activation of carbon-hydrogen bonds in transition-metal complexes, Chem Rev. Mar. 1990;90(2):403-424. doi: 10.1021/cr00100a004.

Scepaniak et al., Formation of ammonia from an iron nitrido complex. Angew Chem Int Ed Engl. 2009;48(17):3158-60. doi:10.1002/anie.200900381.

Sorokin et al., Intramolecular kinetic isotope effects in alkane hydroxylations catalyzed by manganese and iron porphyrin complexes. J Am Chem Soc. Aug. 1993;115(16):7293-7299. doi: 10.1021/ja00069a031.

Sweeney, Aziridines: epoxides' ugly cousins? Chem Soc Rev. Sep. 2002;31(5):247-58.

Tanner et al., Chiral Aziridines—Their Synthesis and Use in Stereoselective Transformations. Angew Chem Int Ed. Mar. 31, 1994;33(6):599-619. doi: 10.1002/anie.199405991.

Thomas et al., Characterization of the terminal iron(IV)imides [[PhBP(t)(Bu)2(pz')]Fe(IV)NAd]+. J Am Chem Soc. Apr. 19, 2006;128(15):4956-7.

Verma et al., A Stable Terminal Imide on Iron. J Am Chem Soc. 2000;122(44):11013-11014. doi: 10.1021/ja001147t.

Wiese et al., C—H functionalization reactivity of a nickel-imide. J Am Chem Soc. Jun. 20, 2012;134(24):10114-21. doi: 10.1021/ja302149k. Epub Jun. 1, 2012.

Ye et al., Quantum chemical studies of C—H activation reactions by high-valent nonheme iron centers. Curr Opin Chem Biol. Feb. 2009;13(1):89-98. doi: 10.1016/j.cbpa.2009.02.007. Epub Mar. 9, 2009.

Zalatan et al., Metal-catalyzed oxidations of C—H to C—N bonds. Top Curr Chem. 2010;292:347-78.

Zhang et al., C—H bond amination by iron-imido/nitrene species. Chinese Science Bulletin. Jul. 2012;57(19):2352-2360. doi: 10.1007/s11434-012-5151-x.

Zhao et al., [((H)L)2Fe6(NCMe)m]n+ (m=0, 2, 4, 6; n=-1, 0, 1, 2, 3, 4, 6): an electron-transfer series featuring octahedral Fe6 clusters supported by a hexaamide ligand platform. J Am Chem Soc. Jun. 1, 2011;133(21):8293-306. doi: 10.1021/ja2015845.

* cited by examiner

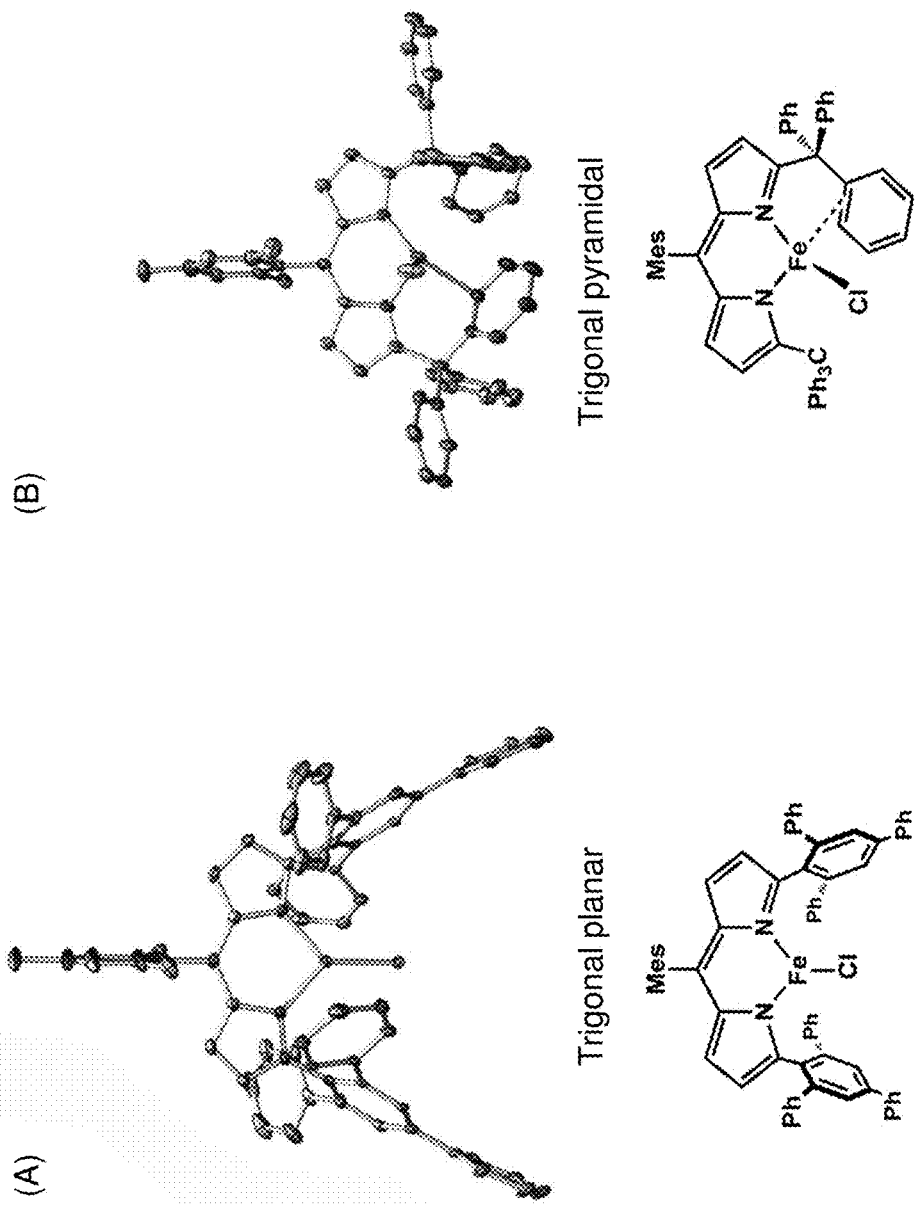
Figure 1A-B

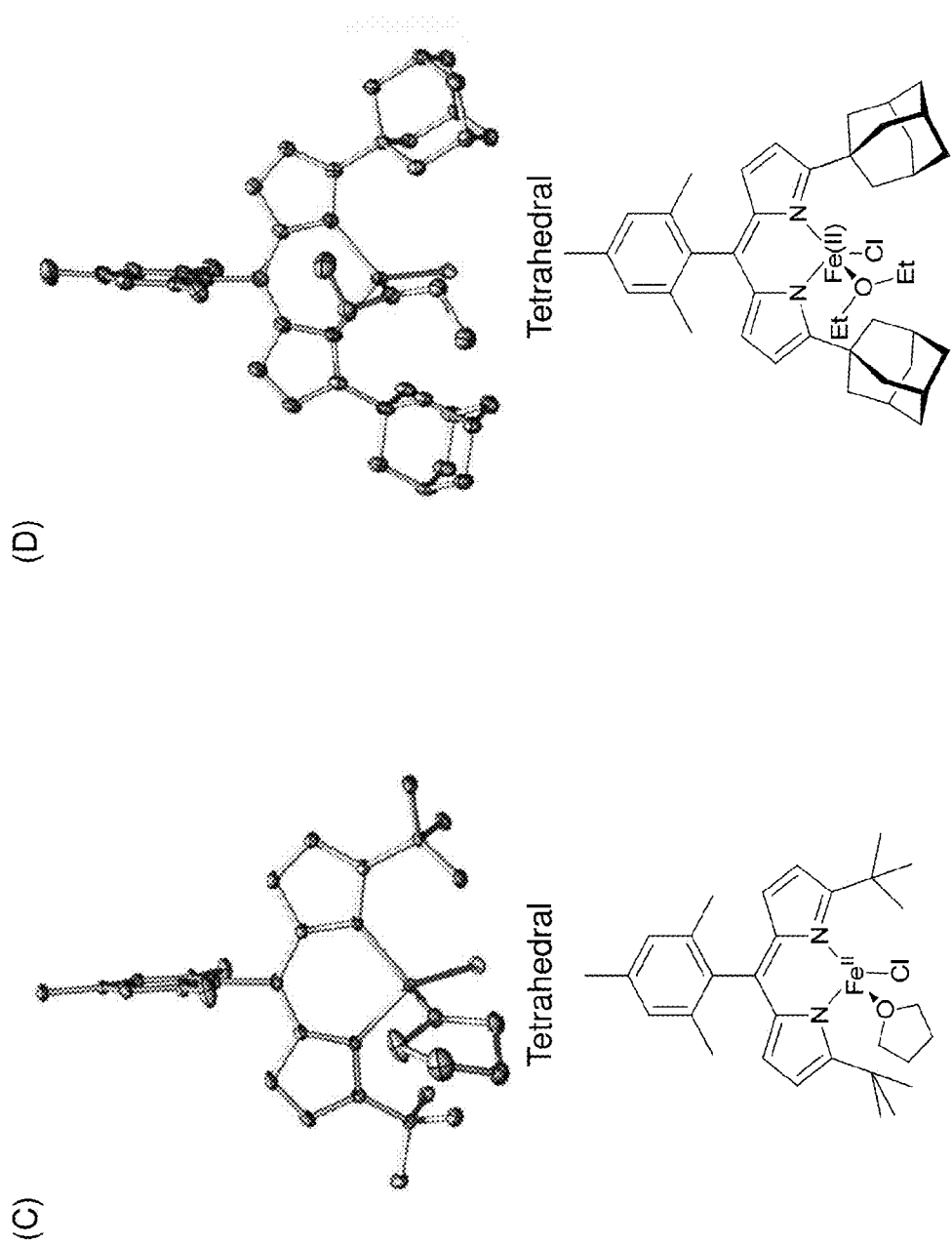
Figure 1C-D

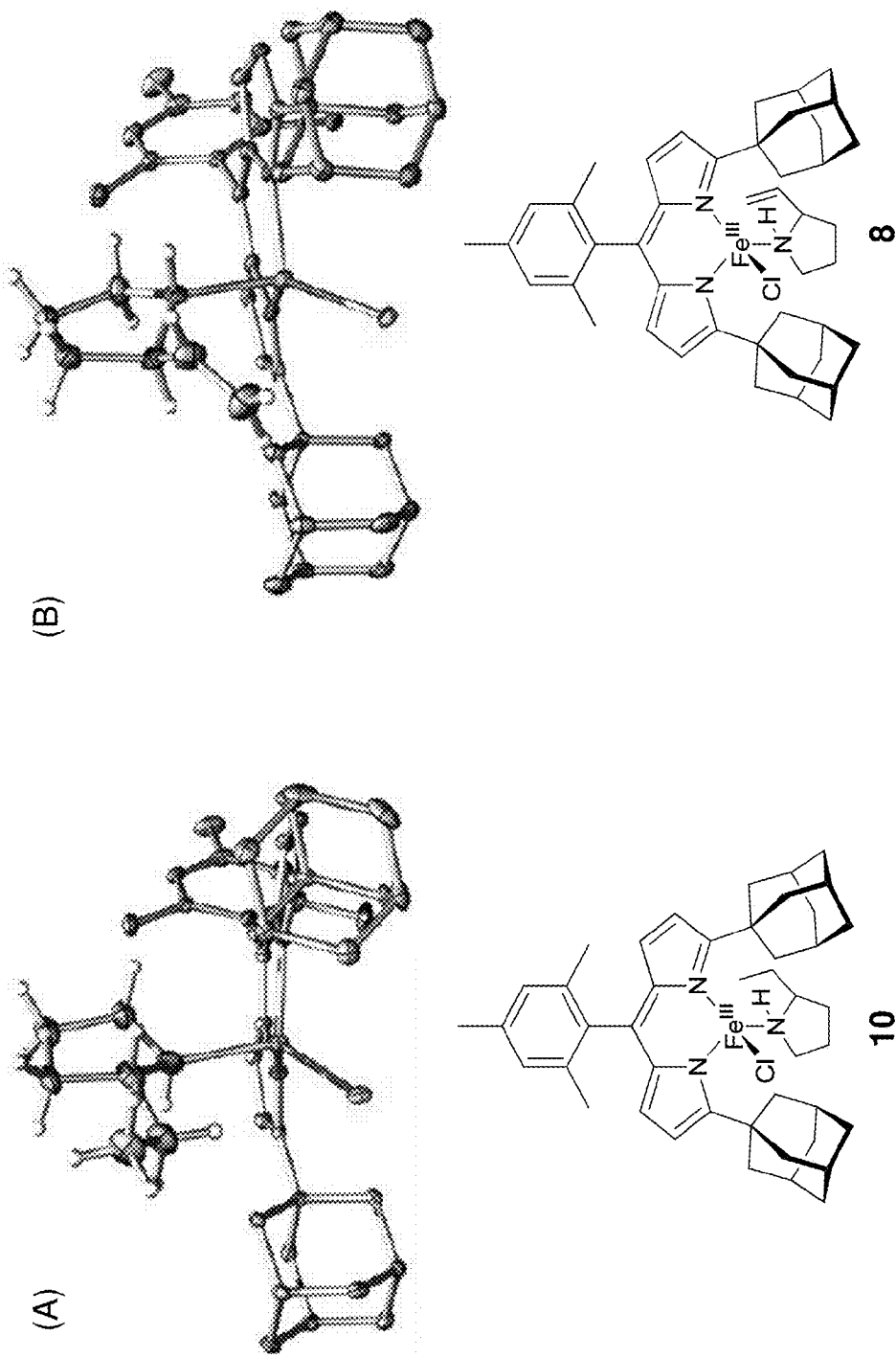
Figure 4A-B

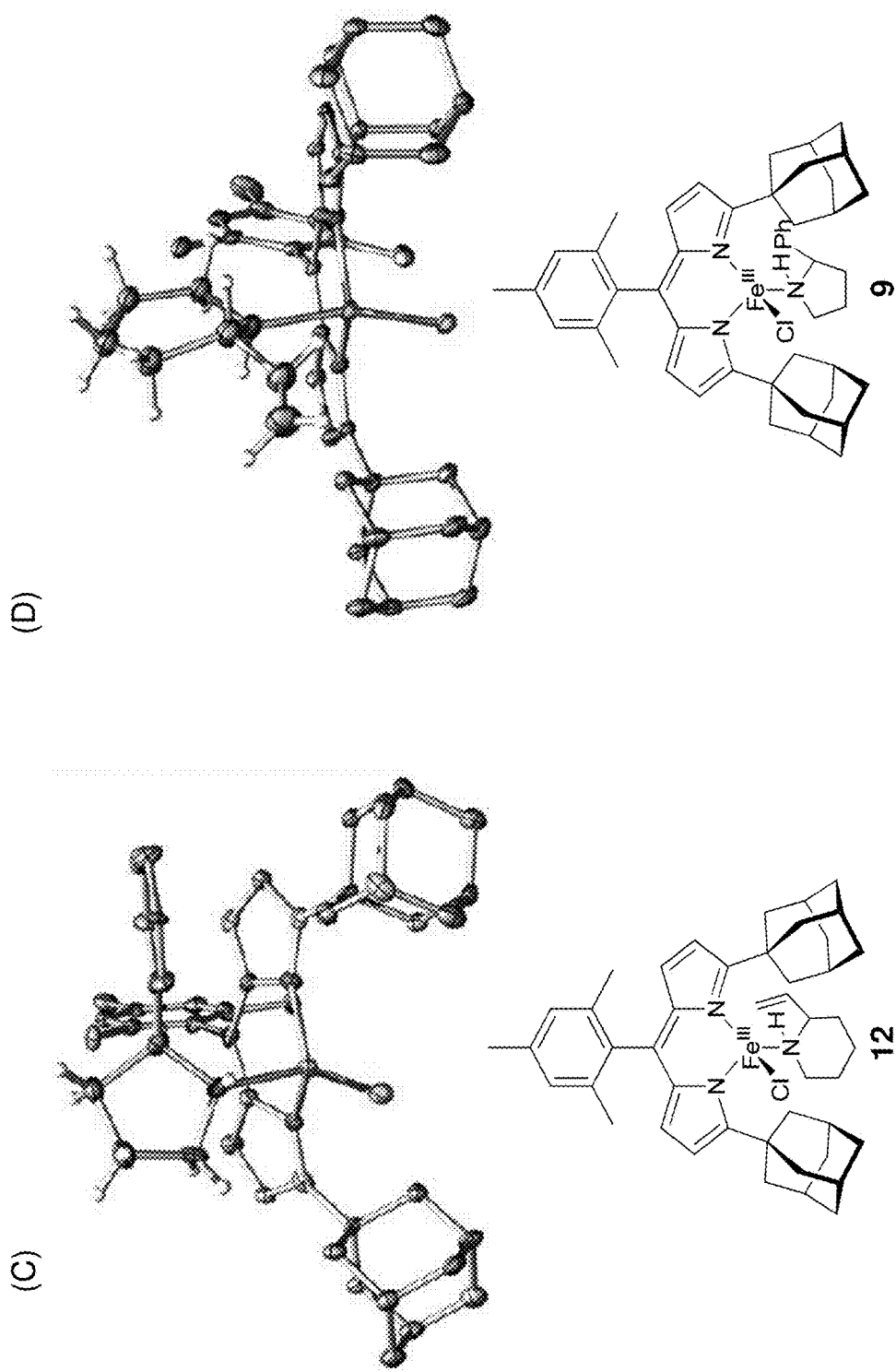
Figure 4C-D

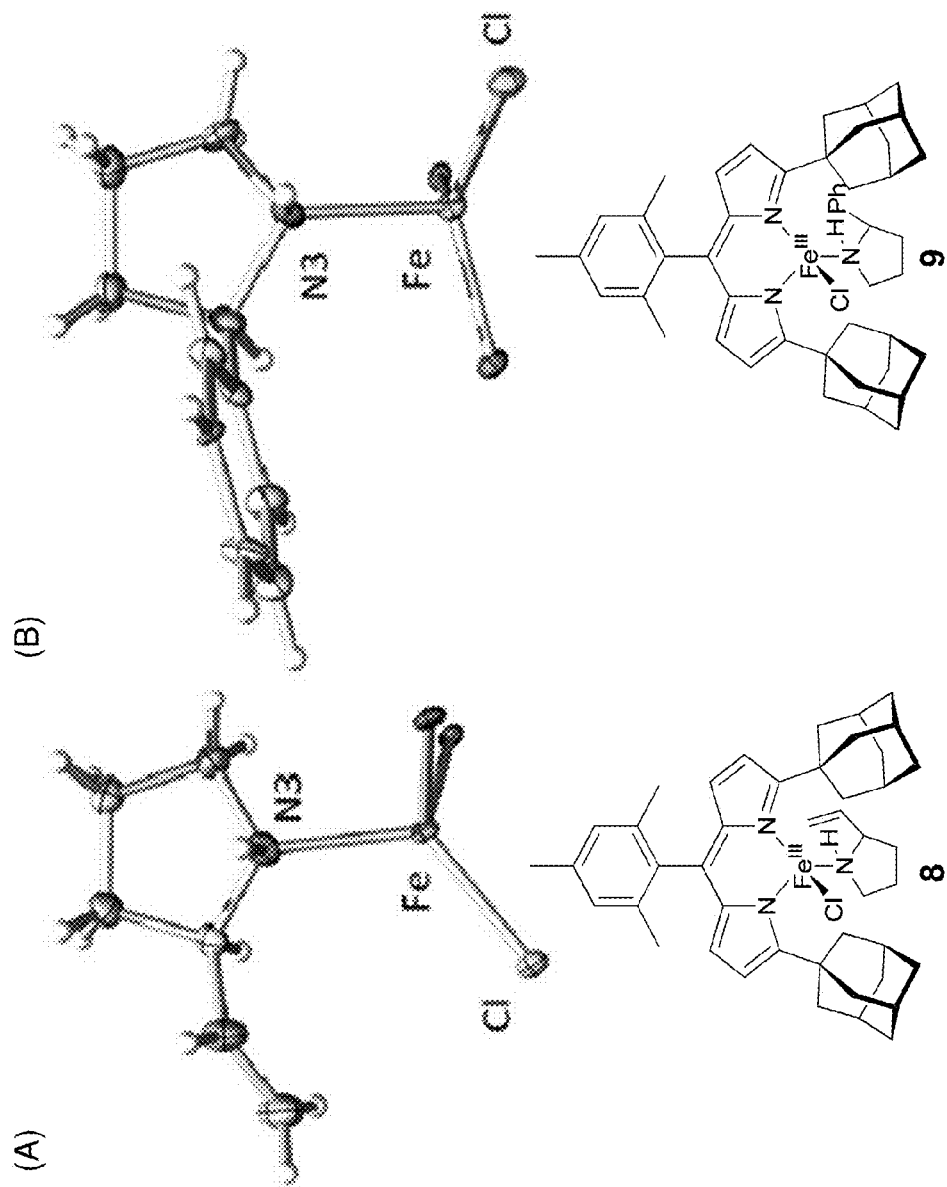
Figure 5A-B

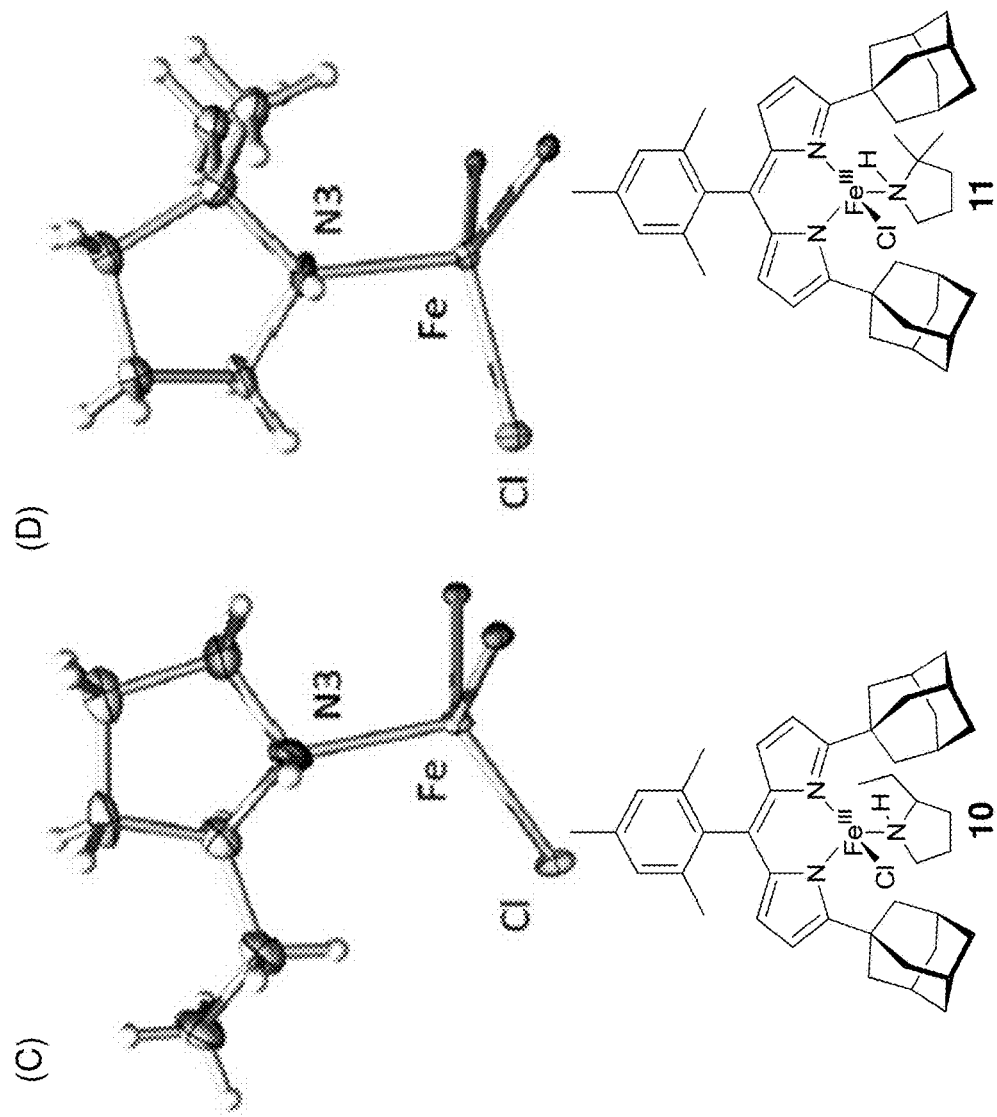
Figure 5C-D

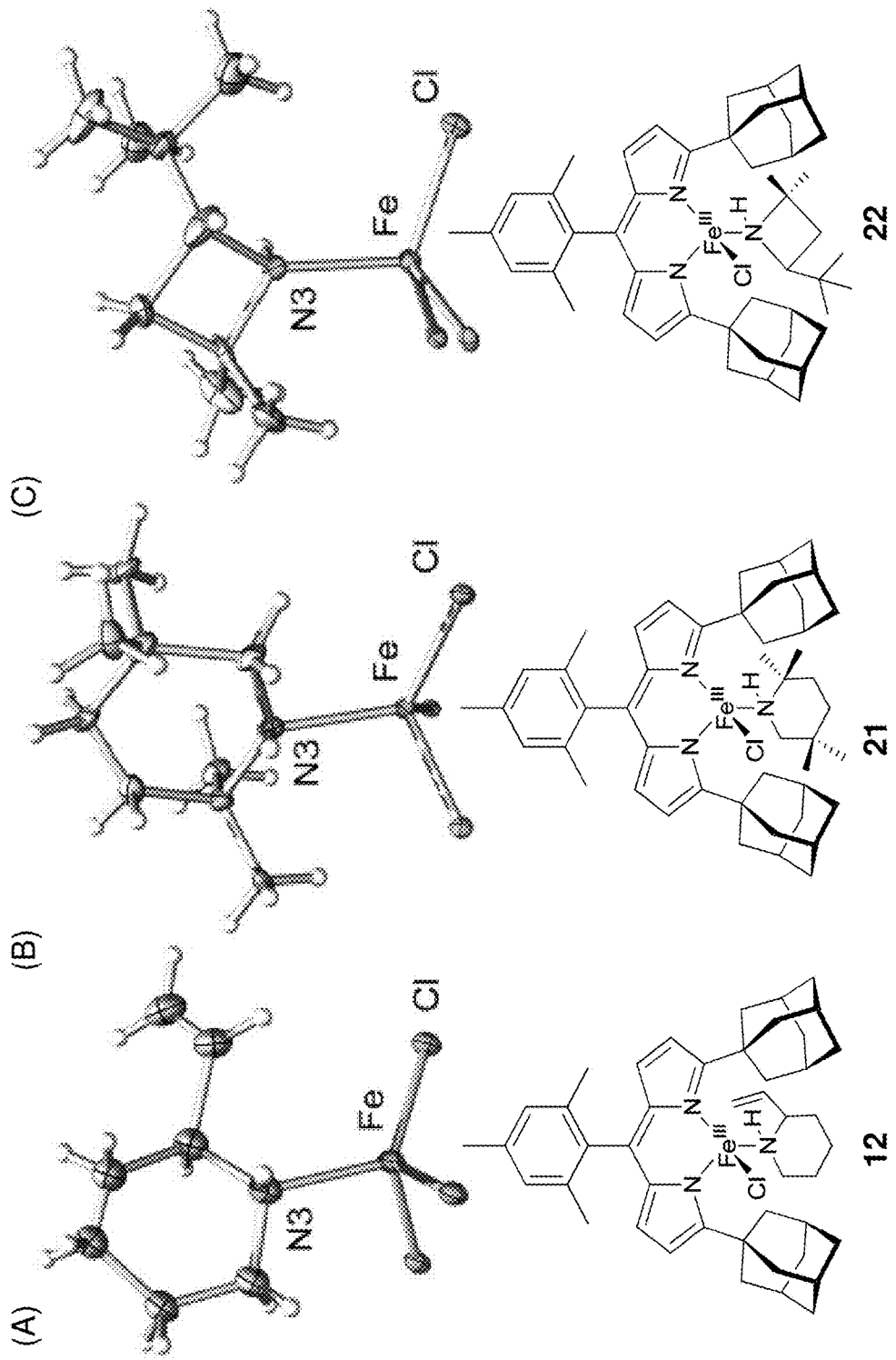
Figure 7A-C

SYNTHESIS OF ACYCLIC AND CYCLIC AMINES USING IRON-CATALYZED NITRENE GROUP TRANSFER

RELATED APPLICATIONS

The present application is a divisional of and claims priority under 35 U.S.C. §120 to U.S. Ser. No. 14/770,217, filed Aug. 25, 2015, now issued as U.S. Pat. No. 9,487,472, which is a national stage filing under 35 U.S.C. §371 of international PCT application, PCT/US2014/018623, filed Feb. 26, 2014, which claims priority under 35 U.S.C. §119(e) to U.S. provisional patent application, U.S. Ser. No. 61/769,469, filed Feb. 26, 2013, each of which is incorporated herein by reference.

GOVERNMENT SUPPORT

This invention was made with government support under grant number CHE-0955885 awarded by the National Science Foundation. The government has certain rights in the invention.

BACKGROUND OF THE INVENTION

Introducing functionality into unactivated C—H bonds remains a significant challenge both in the realm of complex molecule synthesis as well as in the elaboration of simple hydrocarbon feedstocks into value-added commodity chemicals (Bergman, *Nature* 2007, 446, 391; Labinger et al., *Nature* 2002, 417, 507). A challenge to the development of a general and mild aliphatic C—H bond functionalization strategy is the unreactive nature of the substrates themselves. Saturated hydrocarbons are chemically inert due to the large C—H bond dissociation energy (BDE, 93-105 kcal/mol) coupled with the energetic and spatial inaccessibility of the C—H bonding and antibonding orbitals. C—H bond activation processes are only realized under forcing conditions (Labinger et al., *Nature* 2002, 417, 507) or when directing functionalities pre-organize a substrate to interact with transition metal based catalysts (Ryabov, *Chem. Rev.* 90, 403 (1990); Dick et al., *Tetrahedron* 62, 2439 (2006)). Although the C—H bonds of unsaturated substrates (e.g., aromatic and olefinic C—H bonds substrates) are stronger than their aliphatic counterparts (BDE>110 kcal/mol), the available $\pi$-electron system provides a handle to engage the transition metal catalyst prior to C—H bond activation; furthermore, the C—H bonding orbitals are more exposed and thus exhibit greater reactivity. Although chemists have exploited these attributes en route to the functionalization of $sp^2$ C—H bonds, where oxidative addition and reductive elimination reaction pathways are operative (Cho et al., *Science* 295, 305 (2002); Ishiyama et al., *J. Am. Chem. Soc.* 124, 390 (2002)), the catalytic conversion of $sp^3$ C—H bonds within saturated hydrocarbon substrates to carbon-heteroatom bonds remains elusive.

Biological C—H bond functionalization is primarily performed by iron-containing enzymes that utilize dioxygen as the terminal oxidant. A key structural element of the putative hydroxylation catalyst in both heme (where iron is embedded in a porphyrin) and non-heme systems is a transiently formed terminal iron oxo species, typically thought to involve multiple bond character (iron-oxo) (Ortiz de Montellano; Ed. *Cytochrome P450: Structure, Mechanism, and Biochemistry*, 4th ed.; Kluwer Academic/Plenum Publishers: New York, 2005; Krebs et al., *Acc. Chem. Res.* 2007, 40, 484). The iron-oxo contains two electrons residing in Fe—O $\pi^*$ orbitals [Fe($d_{xz}$, $d_{yz}$)-O($p_x$,$p_y$)], which result in a weakened Fe—O bond vector possessing radical character, and thus renders the entire unit a reactive functionality. As a consequence of this electronic configuration, the iron-oxo can activate substrate aliphatic C—H bonds via an H-atom abstraction mechanism and thereby circumvent the orbital spatial restrictions that hinder oxidative addition pathways. Subsequent substrate functionalization results from recombination of the organic radical generated in the activation step with the open-shell iron-hydroxyl to produce an alcohol product with concomitant reduction of the iron species. Despite this mechanistic precedent (Groves et al., *Biochem. Biophys. Res. Commun.* 81, 154 (1978), viable catalysts fashioned with these design principles are only now being discovered. Furthermore, the reactivity of this intermediate is believed to be dictated by its electronic structure (Decker et al., *J. Am. Chem. Soc.* 2007, 129, 15938; Bernasconi et al., *Eur. J. Inorg. Chem.* 2007, 3023; Ye et al., *Curr. Opin. Chem. Biol.* 2009, 13, 89). In non-heme enzymes, four such $Fe^{IV}$ (oxo) complexes have been characterized, and their reactivity has been linked to a common electronic feature: namely a high-spin ground state (S=2) (Krebs et al., *Acc. Chem. Res.* 2007, 40, 484).

The direct functionalization of C—H bonds based on a strategy exemplified by cytochrome P450 would be transformative in converting ubiquitous C—H bonds into functional group handles and would circumvent the traditional synthetic requirement for functional group exchange (King et al., *Top. Organometallic Chem.* 6, 205, (2004)). The electronic structure of the cytochrome P450 reactive iron-oxo intermediate can be, in principle, be replicated with any metal-ligand multiple bond (Nugent et al., *Metal-Ligand Multiple Bonds*; Wiley: New York, N.Y., 1988), and would constitute a general strategy for the conversion of unactivated C—H bonds into a variety of C-heteroatom bond products. Indeed, metal stabilized carbene and nitrene transfer has garnered significant interest using noble metal catalysts (Zalatan et al., *Top. Curr. Chem.* 292, 347 (2010); Au et al., *J. Am. Chem. Soc.* 121, 9120 (1999); Davies et al., *Nature* 451, 417 (2008)). In contrast, late, first row-transition metal complexes are potentially ideal catalyst candidates but have been less explored. Their high d-electron count and compressed ligand fields (compared to their second and third row analogues) favor population of metal-ligand antibonding orbitals leading to destabilization and reactivity akin to the cytochrome P450 iron-oxo intermediate (Badiei et al., *Angew. Chem., Int. Ed.* 47, 9961 (2008); Laskowski et al., *J. Am. Chem. Soc.* 133, 771 (2011); King et al., *J. Am. Chem. Soc.* 133, 4917 (2011); Lyaskovskyy et al., *J. Am. Chem. Soc.* 133, 12264 (2011); Wiese et al., *J. Am. Chem. Soc.* 134, 10114 (2012)).

Parallel to the work targeted at iron-mediated hydroxylation chemistry, C—H bond amination (Müller et al., *Chem. Rev.* 2003, 103, 2905; Davies et al., *Angew. Chem., Int. Ed.* 2005, 44, 3518; Halfen, *Curr. Org. Chem.* 2005, 9, 657; Cenini et al., *Coord. Chem. Rev.* 2006, 250, 1234. Davies et al., *Nature* 2008, 451, 417; Collet et al., *Chem. Commun.* 2009, 5061; Zalatan et al., *J. Top. Curr. Chem.* 2010, 292, 347) and olefin aziridination (Müller et al., *Chem. Rev.* 2003, 103, 2905; Halfen, Curr. *Org. Chem.* 2005, 9, 657; Tanner, *Angew. Chem., Int. Ed.* 1994, 33, 599; Osborn et al., *Tetrahedron: Asymmetry* 1997, 8, 1693; Sweeney, *Chem. Soc. Rev.* 2002, 31, 247) have been reported. The synthesis and characterization of Fe(imido) complexes as isoelectronic surrogates to Fe(oxo) functionalities have been targeted in the pursuit of effecting viable catalytic delivery of the nitrene functional unit to a C—H bond or olefinic substrates. Iron imido complexes have now been characterized in four oxidation states spanning a range of spin states ($Fe^{II}$, S=0 (Brown et al., *J. Am. Chem. Soc.* 2005, 127, 1913); $Fe^{III}$, S=1/2, 1, 3/2 (Brown et al., *J. Am. Chem. Soc.* 2003, 125, 322; Betley et al., *J. Am. Chem. Soc.* 2003, 125, 10782; Bart et al., *J. Am. Chem. Soc.* 2006, 128, 5302; Lu et al., *J. Am. Chem. Soc.* 2007, 129, 4; Scepaniak et al., *Angew. Chem., Int. Ed.* 2009, 48, 3158; Cowley et al., *Inorg. Chem.* 2010, 49, 6172); $Fe^{IV}$, S=1; (Verma et al., *J. Am. Chem. Soc.* 2000, 122, 11013; Thomas et al., *J. Am. Chem. Soc.* 2006, 128, 4956; Nieto et al., *J. Am. Chem. Soc.* 2008, 130, 2716); Fe(V), S=1/2 (Ni et al., *Chem. Commun.* 2008, 6045)) and have been shown to engage in group transfer to carbon monoxide to produce isocyanates (Brown et al., *J. Am. Chem. Soc.* 2003, 125, 322; Cowley et al., *Chem. Commun.* 2009, 1760) and to isocyanides to produce carbodiimides (Cowley et al., *Chem. Commun.* 2009, 1760), undergo hydrogenation (Bart et al., *J. Am. Chem. Soc.* 2006, 128, 5302), and perform H atom abstraction from C—H bonds (Cowley et al., *Inorg. Chim. Acta* 2011, 369, 40-44; King et al, *Inorg. Chem.* 2009, 48, 2361).

For example, it has been recently reported that a catalytic C—H bond amination of toluene yields secondary benzylamines through a transiently formed, high-spin (S=2) iron imido complex (Scheme 1). See, e.g., King et al. (*J. Am. Chem. Soc.* 2011, 133, 4917-4923). Isolation and characterization of the reactive intermediate elucidated the unique electronic structure of its high-spin iron-bound imido radical, wherein a high-spin Fe(III) (S=5/2) is antiferromagnetically coupled to the imido radical (S=−1/2) to give a high-spin ground state. This electronic structure places significant radical character on both the Fe—N σ and π bond vectors, facilitating both radical H-atom abstraction and radical recombination pathways to proceed. Furthermore, the amination catalytic cycle remains in the quintet spin state (S=5/2), making each step of the catalytic cycle spin-allowed.

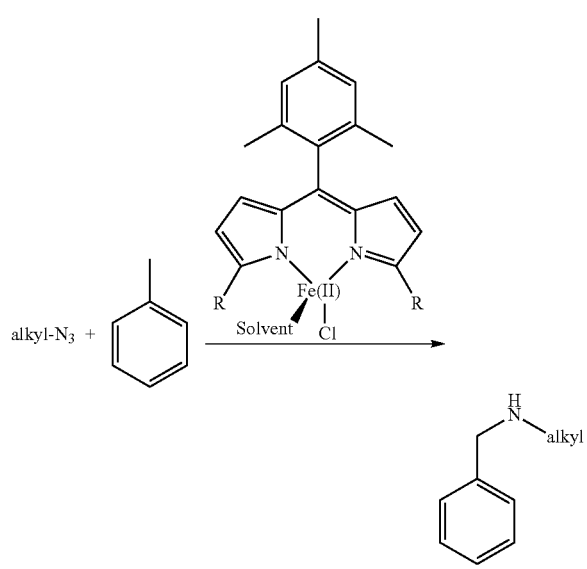

Scheme 1.

Also reported is the preparation of substituted aziridines through a catalytic C—H bond amination of styrene (Scheme 2). See, e.g., King et al. (*J. Am. Chem. Soc.* 2011, 133, 4917-4923).

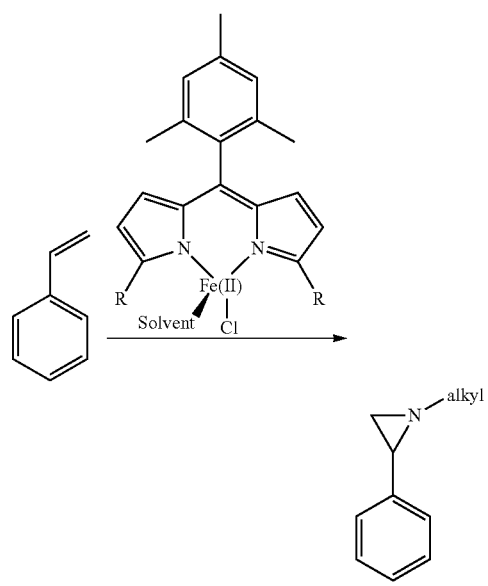

Scheme 2.

Despite these efforts, a facile synthetic route to a wide range of functionalized amines (e.g., acyclic and cyclic secondary amines) is still in need.

SUMMARY OF THE INVENTION

The ability to selectively incorporate functionality into unactivated C—H bonds represents a significant advance in chemical synthesis of a range of useful compounds, such as acyclic and cyclic amines. Such amines are important building blocks for the synthesis of biologically active natural products, pharmaceutical agents. Reported strategies for constructing those amines, such as saturated heterocyclic amines, are heavily dependent on functional group exchange, leading to inefficient synthetic protocols with poor atom economy and waste generation. A catalyst capable of the direct amination of aliphatic C—H bonds may be employed for a streamlined synthetic approach to those amines. One of the advantages of this method is its potential to harness saturated hydrocarbon feedstocks. Unfortunately, current C—H bond functionalization protocols often require substrate preoxidation or strong chemical oxidants (Zalatan et al., *Top. Curr. Chem.* 292, 347 (2010)), which contribute to a lack of generality for this bond construction. The present invention provides a selective synthesis of a variety of acyclic and cyclic amines using iron-catalyzed nitrene group transfer into tertiary, secondary, and primary C—H bonds. The present invention not only provides the synthetic methodology to such amines but also provide the catalysts, ligands, intermediates, and systems useful in the inventive methodology. The iron-based catalysts used in the inventive methods are capable of functionalizing a broad range of aliphatic C—H bonds to form the amines. This novel methodology provides access to acyclic and cyclic amines of various chain-lengths or ring sizes and of architectural diversity that will find significant utility in, e.g., pharmaceutical and fine chemical synthesis.

In one aspect, the present invention provides methods of preparing acyclic secondary amines of Formula (I):

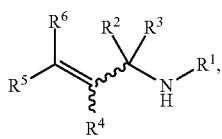
(I)

and salts and stereoisomers thereof, wherein $R^1$-$R^6$ are as described herein. The inventive methods comprise the steps of:

reacting an azide of Formula (A), or a salt or stereoisomer thereof, with a ferrous ($Fe^{II}$) compound of Formula (B) (a $Fe^{II}$-dipyrromethene complex), or a salt or stereoisomer thereof, to provide a ferric ($Fe^{III}$) compound of Formula (C) (a $Fe^{III}$-dipyrromethene complex), or a salt or stereoisomer thereof:

(A)

$N_3$—$R^1$ (B)

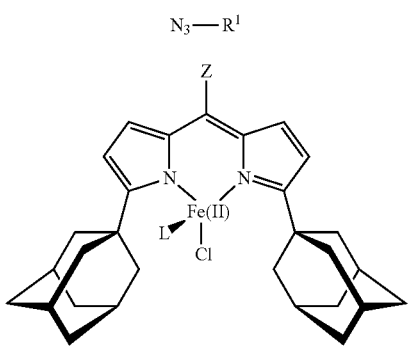

(C)

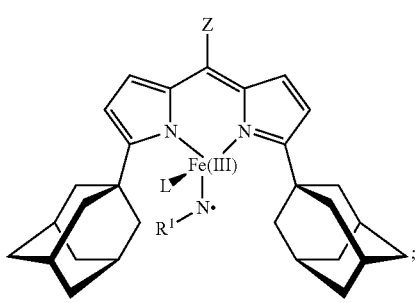

and reacting the ferric compound of Formula (C), or a salt or stereoisomer thereof, with a compound of Formula (D) or (E), or a salt or stereoisomer thereof, to provide a compound of Formula (I):

(D)

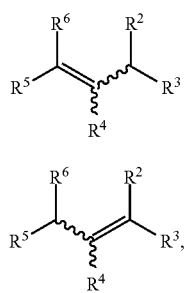

(E)

or a salt or stereoisomer thereof.

The inventive methods involve an iron-based catalyst, e.g., the ferrous ($Fe^{II}$) compound of Formula (B), that may leverage the reactivity of the iron-born metal-ligand multiple bonds to promote the direct amination of the aliphatic C—H bonds of the compound of Formula (D) or (E), or a salt or stereoisomer thereof. Exposure of an organic azide (e.g., the compounds of Formula (A), or a salt or stereoisomer thereof) to the iron-based catalyst furnishes amines (e.g., the compound of Formula (I), or a salt or stereoisomer thereof) that may bear complex core-substitution patterns.

Another aspect of the present invention relates to methods of preparing a compound of Formula (II-1):

(II-1)

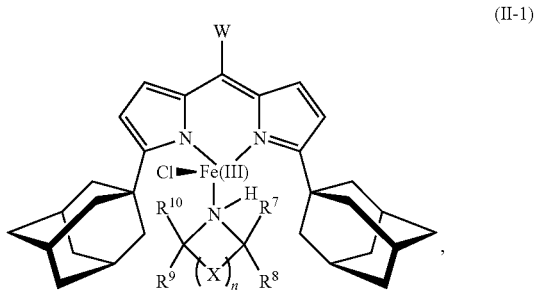

or a salt or stereoisomer thereof, the method comprising reacting an azide of Formula (F), or a salt or stereoisomer thereof, with a ferrous compound of Formula (G) (a $Fe^{II}$-dipyrromethene complex), or a salt or stereoisomer thereof:

(F)

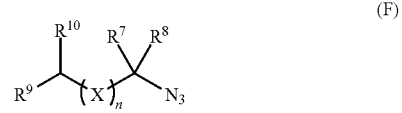

(G)

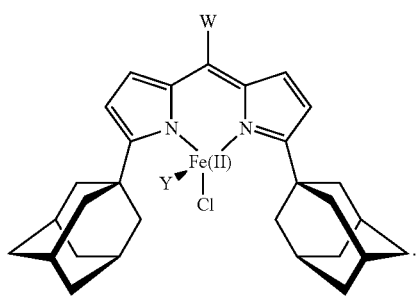

In another aspect, the method of preparing a compound of Formula (II-1), or a salt or stereoisomer thereof, further comprises reacting the compound of Formula (II-1), or a salt or stereoisomer thereof, with $Boc_2O$ to provide a compound of Formula (II-2-A):

(II-2-A)

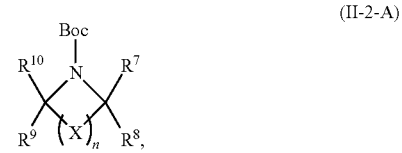

or a salt or stereoisomer thereof.

In another aspect, the method of preparing a compound of Formula (II-1), or a salt or stereoisomer thereof, further comprises reacting the compound of Formula (II-1), or a salt or stereoisomer thereof, with Fmoc-OSuc to provide a compound of Formula (II-2-B), or a salt thereof:

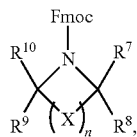
(II-2-B)

or a salt or stereoisomer thereof.

In still another aspect, the method of preparing a compound of Formula (II-2-A) or (II-2-B), or a salt or stereoisomer thereof, further comprises deprotecting the compound of Formula (II-2-A) or (II-2-B), or a salt or stereoisomer thereof, to provide a cyclic amine of Formula (II-3):

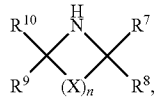
(II-3)

or a salt or stereoisomer thereof.

Exemplary compounds that may be prepared using the inventive methods include, but are not limited to:

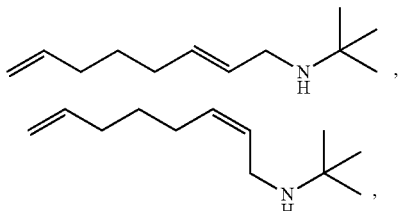

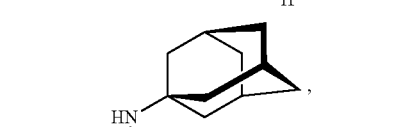

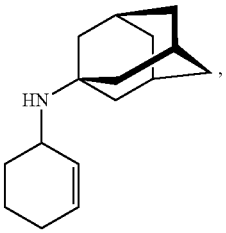

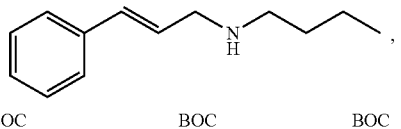

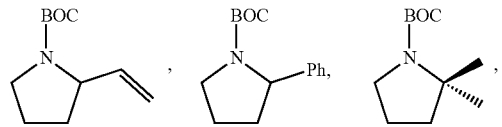

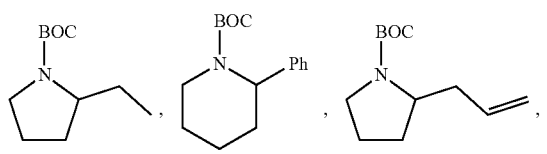

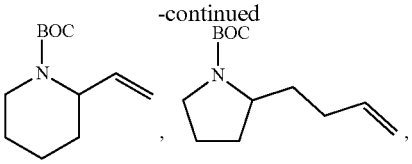

-continued

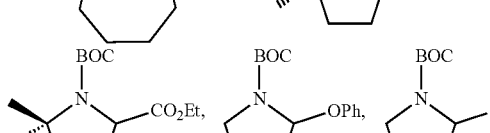

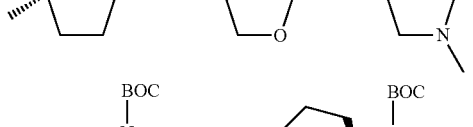

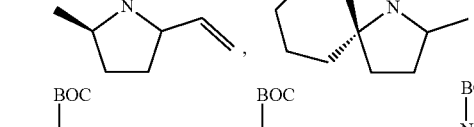

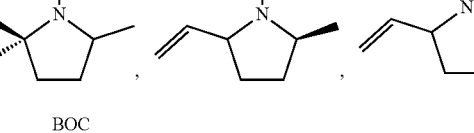

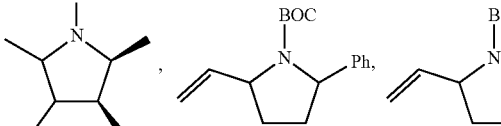

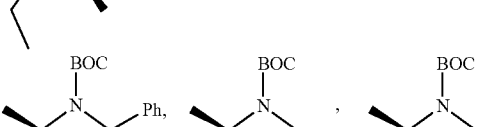

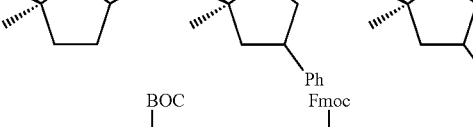

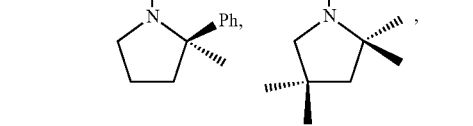

and salts and stereoisomers thereof.

The present application refers to various issued patent, published patent applications, journal articles, and other publications, all of which are incorporated herein by reference.

The details of one or more embodiments of the invention are set forth herein. Other features, objects, and advantages of the invention will be apparent from the Detailed Description, the Figures, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

When a range of values is listed, it is intended to encompass each value and sub-range within the range. For example "$C_{1-6}$" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$.

The term "aliphatic" refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., —$CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclic ring, as defined above, is fused with one or more aryl or heteroaryl groups wherein the point of attachment is on the carbocyclic ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclic ring, as defined above, is fused with one or more carbocyclyl groups wherein the point of attachment is either on the carbocyclyl or heterocyclic ring, or ring systems wherein the heterocyclic ring, as defined above, is fused with one or more aryl or heteroaryl groups, wherein the point of attachment is on the heterocyclic ring, and in such instances, the number of ring members continue to designate the number of ring members in the heterocyclic ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, and thiiranyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6-membered heterocyclyl groups containing three heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 p electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Aralkyl" is a subset of alkyl and aryl, as defined herein, and refers to an optionally substituted alkyl group substituted by an optionally substituted aryl group. In certain embodiments, the aralkyl is optionally substituted benzyl. In certain embodiments, the aralkyl is benzyl. In certain embodiments, the aralkyl is optionally substituted phenethyl. In certain embodiments, the aralkyl is phenethyl.

"Heteroaryl" refers to a radical of a 5-10 membered monocyclic or bicyclic 4n+2 aromatic ring system (e.g., having 6 or 10 p electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted (an "unsubstituted heteroaryl") or substituted (a "substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

"Heteroaralkyl" is a subset of alkyl and heteroaryl, as defined herein, and refers to an optionally substituted alkyl group substituted by an optionally substituted heteroaryl group.

"Partially unsaturated" refers to a group that includes at least one double or triple bond. A "partially unsaturated" ring system is further intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, which are divalent bridging groups are further referred to using the suffix -ene, e.g., alkylene, alkenylene, alkynylene, carbocyclylene, heterocyclylene, arylene, and heteroarylene.

As used herein, the term "optionally substituted" refers to optionally substituted.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —SCN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{cc}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —SCN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —SCN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —C(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$-perhaloalkyl, C$_{2-6}$ alkenyl, C$_{2-4}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl and 5-10 membered heteroaryl, or two R groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —SCN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-4}$ alkyl), —NHC(=O)NH$_2$, —C(=NH)O(C$_{1-4}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(H)NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, —C(=S)NH(C$_{1-6}$ alkyl), —C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(X)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

"Acyl" as used herein refers to a moiety selected from the group consisting of —C(=O)R$^{aa}$, —CHO, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —C(=O)NR$^{bb}$SO$_2$R$^{aa}$, —C(=S)N(R$^{bb}$)$_2$, —C(=O)SR$^{aa}$, or —C(=S)SR$^{aa}$, wherein R$^{aa}$ and R$^{bb}$ are as defined herein.

Nitrogen atoms can be optionally substituted as valency permits, and include primary, secondary, tertiary, and quaternary nitrogen atoms. Exemplary nitrogen atom substituents include, but are not limited to, hydrogen, —OH, —OR$^{aa}$, —N(R$^{cc}$)$_2$, —CN, —SCN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

For example, nitrogen protecting groups such as amide groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, and o-(benzoyloxymethyl)benzamide.

Nitrogen protecting groups such as carbamate groups (e.g., —C(=O)OR$^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-1-butyl-[9-(10, 10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (or t-butyloxycarbonyl (BOC or Boc)), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate,

[2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-pnitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, t-butyloxycarbonyl (BOC or Boc), alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})$ $R^{aa}$, —$C(=NR^{bb})OR^{aa}$, —$C(=NR^{bb})N(R^{bb})_2$, —$S(=O)$ $R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

"Adamantyl" or "Ad" refers to adamantane radical

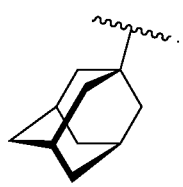

"Mesityl" or "Mes" refers to 2,4,6-trimethylphenyl.

"$Boc_2O$" or "$(BOC)_2O$" refers to Boc anhydride or, in other words, di-t-butyl dicarbonate.

As used herein, the term "nitrene" refers to a compound that can be represented by the general formula

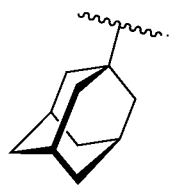

wherein $R^N$ is an atom or group including, but not limited to, hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl. A nitrene is the nitrogen analog of a carbene. The nitrogen atom of a nitrene has only six valence electrons and is, therefore, an electrophile. In the most simple nitrene, the linear imidogen (HN:), two of the six available electrons form a covalent bond with hydrogen, and two other create a free electron pair and the two remaining electrons occupy two degenerate p orbitals. Because nitrenes are highly reactive, they are usually not isolated. Instead, they are formed as reactive intermediates during a reaction. There are two common ways to generate nitrenes: (1) from azides by thermolysis or photolysis, with expulsion of nitrogen gas; and (2) from isocyanates, with expulsion of carbon monoxide.

The term "amination" refers to a chemical reaction that involves the formation of one or more carbon-nitrogen bond, wherein the nitrogen is trivalent.

The term "catalysis" refers to the change in rate of a chemical reaction due to the participation of a substance called a "catalyst." Unlike other reagents that participate in the chemical reaction, a catalyst is not consumed by the reaction itself. A catalyst works by providing an alternative reaction pathway to the reaction product. Catalytic reactions have a lower rate-limiting free energy of activation than the corresponding uncatalyzed reaction, resulting in a higher reaction rate at the same temperature. A reaction is "catalyzed" when the addition of a catalyst into the reaction increases the reaction rate of the reaction. Exemplary mechanistic explanations of catalysis include that catalysts may affect the reaction environment favorably, bind to the reagents to polarize bonds, form specific intermediates that are not produced naturally, or cause lysis of reagents to reactive forms. Kinetically, catalytic reactions are typical chemical reactions; i.e., the reaction rate depends on the frequency of contact of the reactants in the rate-determining step. Usually, the catalyst participates in this slowest step, and reaction rates are limited by the amount of catalyst and its activity. Many transition metals and transition metal complexes as illustrated by the present invention are catalysts.

The term "Fmoc-OSuc" refers to 9-fluorenylmethyl N-succinimidyl carbonate or Fmoc-OSu.

As used herein, the terms "$Fe^{II}$" and "Fe(II)" are used interchangeably.

As used herein, the terms "$Fe^{III}$" and "Fe(III)" are used interchangeably.

These and other exemplary substituents are described in more detail in the Detailed Description, Figures, Examples, and Claims. The invention is not intended to be limited in any manner by the above exemplary listing of substituents.

OTHER DEFINITIONS

The following definitions are more general terms used throughout the present application:

As used herein, the term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4^-$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, loweralkyl sulfonate, and aryl sulfonate.

The term "tautomers" refer to compounds that are interchangeable forms of a particular compound structure, and that vary in the displacement of hydrogen atoms and electrons. Thus, two structures may be in equilibrium through the movement of π electrons and an atom (usually H). For example, enols and ketones are tautomers because they are rapidly interconverted by treatment with either acid or base. Another example of tautomerism is the acid- and nitro-forms of phenylnitromethane, that are likewise formed by treatment with acid or base.

Tautomeric forms may be relevant to the attainment of the optimal chemical reactivity and biological activity of a compound of interest.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A non-human animal may be a transgenic animal.

The terms "administer," "administering," or "administration," as used herein refers to implanting, absorbing, ingesting, injecting, inhaling, or otherwise introducing a compound (e.g., an acyclic or cyclic amine synthesized using the methods of the invention), or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

BRIEF DESCRIPTION OF THE DRAWINGS

FIGS. 1A-D show exemplary X-ray crystal structures of $Fe^{II}$-dipyrromethene complexes useful in catalyzing C—H bond amination reactions.

FIGS. 4A-D are exemplary X-ray crystal structures of $Fe^{III}Cl$ (cyclic amine)-dipyrromethene complexes.

FIGS. 5A-D are exemplary solid-state core structures of $Fe^{III}Cl$ (cyclic amine)-dipyrromethene complexes. (A) $(^{Ad}L)$FeCl(2-$C_2H_3$—NHC$_4H_7$) 8; (B) $(^{Ad}L)$FeCl(2-Ph-NHC$_4H_7$) 9; (C) $(^{Ad}L)$FeCl(2-Et-NHC$_4H_7$) 10; (D) $(^{Ad}L)$FeCl(2,2-Me$_2$-NHC$_4H_7$) 11. Thermal ellipsoids were set at the 50% probability level. Average bond lengths (Å) for: Fe—$N_{dipyrrin}$ 2.046(3), 2.062(3); Fe—N3, 2.145(3); Fe—Cl, 2.266(4).

FIGS. 7A-C are exemplary solid-state core structures of $Fe^{III}Cl$ (cyclic amine)-dipyrromethene complexes. (A) $(^{Ad}L)$FeCl(2-$C_2H_3$—NHC$_5H_9$) 12; (B) $(^{Ad}L)$FeCl(2,2-Me$_2$-5,5-

Figure 2:
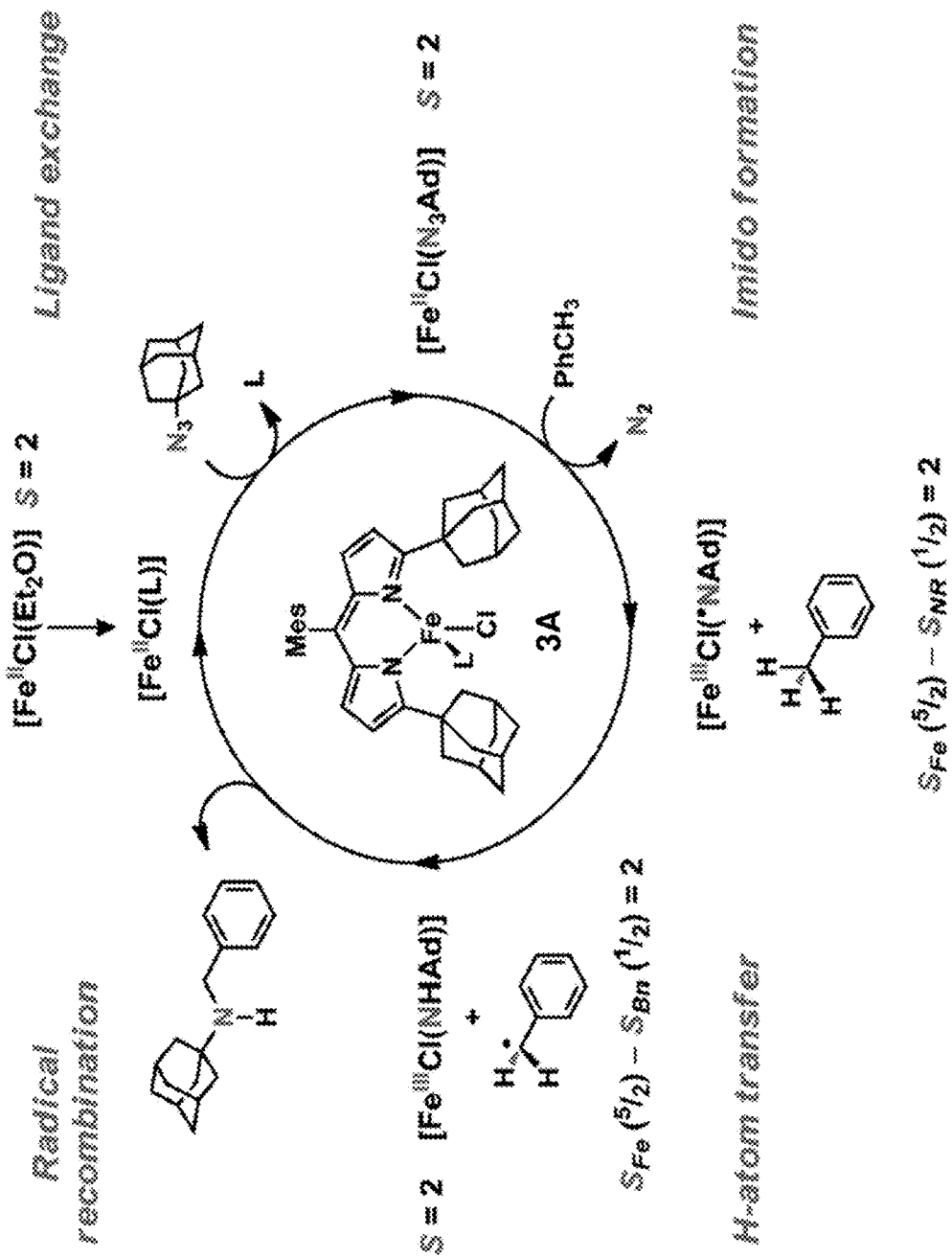
FIG. 2 illustrates a proposed mechanism of an intermolecular C—H amination reaction catalyzed by $Fe^{II}$-dipyrromethene complex 3A to yield acyclic secondary amines.

Me$_2$-NHC$_5$H$_6$) 21; (C) ($^{Ad}$L)FeCl(2,2-Me$_2$-4-(t-Bu)-NHC$_3$H$_3$) 22. Thermal ellipsoids were set at the 50% probability level.

DETAILED DESCRIPTION OF CERTAIN EMBODIMENTS OF THE INVENTION

A class of electrophilic complexes has been synthesized that are capable of mediating C—H bond functionalization through transiently-formed, or metastable, transition states. Using dipyrromethene ligand platforms as truncated models of the porphyrin platform found in P450 hydroxylase enzymes, it has been observed that the reactivity from the ferrous-ligand constructs mirrors their porphyrin analogs. Illustrated in FIG. 1 are exemplary dipyrromethene ligand platforms that may be useful in the present invention. All these Fe$^{II}$-dipyrromethene complexes show a high-spin state (S=2). Catalytic C—H bond (e.g., a sp$^3$ C—H bond) amination has been observed from the reaction of organic azides R—N$_3$ with Fe$^{II}$ coordination complex 1 to form Fe$^{III}$ (imido) complex 2 (Scheme 3). Shown in Table 1 are mass spectrometric data indicating the formation of 2.

TABLE 1

| Mass spectrometric data (TOF/ESI) of Fe$^{III}$ (imido) complex 2. | | |
|---|---|---|
| R | Calculated m/z [M + H]$^+$ | Observed m/z [M + H]$^+$ |
| Ad | 648.4318 | 648.4284 |
| t-Bu | 570.3848 | 570.3851 |
| Ph | 590.3535 | 590.3509 |
| Mes | 632.4004 | 632.3965 |
| Ts | 668.3310 | 668.3306 |

The iron-catalyzed amination reaction is useful with a variety of organic azides and has shown reactivity with a range of organic substrates to form acyclic and cyclic secondary amines. For example, linear azides can be intramolecularly aminated to form pyrrolidine or piperidine derivatives having an array of ring-substitutions, including heteroatom-bearing functional groups. It is well known in the art that the azides employed in the inventive methods can be prepared using a variety of synthetic methods. For example, alkyl azides may be made by ring-opening an epoxide using a nucleophilic compound (e.g., a Grignard reagent or alkyl lithium reagent) to afford a terminal alcohol, followed by conversion of the terminal alcohol to the corresponding azide. See, e.g., Corey et al., J. Am. Chem. Soc., 1992, 114, 1906-1908, incorporated herein by reference. Aryl azides may be prepared through a copper(II)-catalyzed conversion of organoboron compounds. See, e.g., Grimes et al., Synthesis, 2010, 1441-1448, incorporated herein by reference. Acyl azides may be synthesized by reacting carboxylic acids with trichloroacetonitrile, triphenylphosphine, and sodium azide. See, e.g., Kim et al., Synlett, 2008, 2072-2074, incorporated herein by reference.

Therefore, by iron-catalyzed nitrene group transfer into tertiary, secondary, and primary C—H bonds, a wide range of functionalized products (e.g., acyclic and cyclic secondary amines) can be readily synthesized. For example, acyclic secondary amines may be prepared by an intermolecular reaction of an azide with a C—H source, catalyzed by a Fe$^{II}$-dipyrromethene complex, e.g., compound 3A shown in FIG. 1D. Cyclic secondary amines (e.g., 5-, 6-, and 7-membered cyclic secondary amines) may be synthesized by an intramolecular reaction of an azide that bears one or more C—H groups, catalyzed by a Fe$^{II}$-dipyrromethene complex, e.g., compound 3A (FIG. 1D). These reactions generate little waste and are useful in the synthesis of fine chemicals and pharmaceuticals.

Scheme 3.

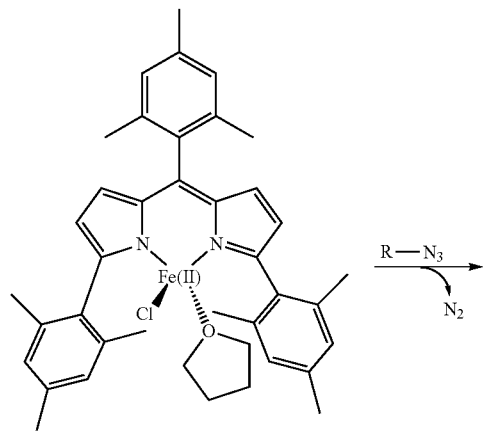

1

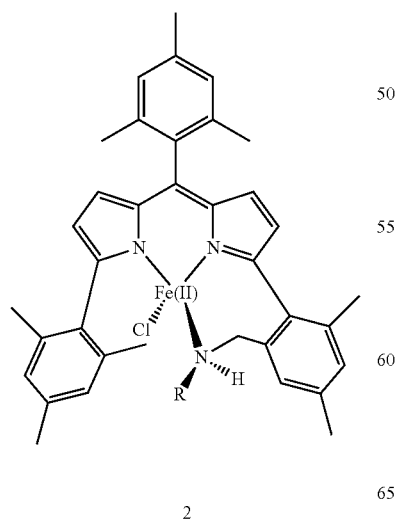

2

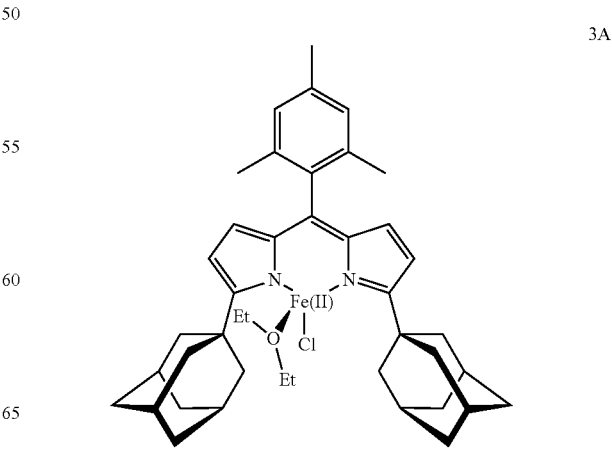

3A

-continued

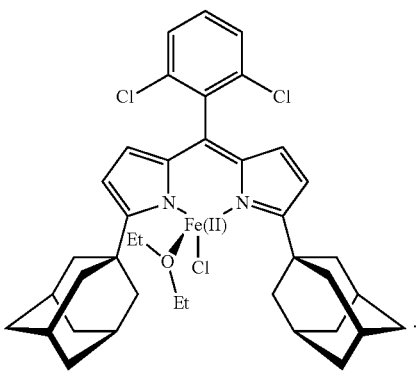
3B

Synthesis of Acyclic Secondary Amines

In one aspect, the present invention provides methods of preparing compounds of Formula (I), which are acyclic secondary amines:

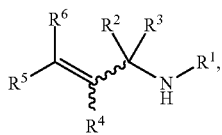
(I)

and salts and stereoisomers thereof, the method comprising the steps of:

reacting an azide of Formula (A), or a salt or stereoisomer thereof, with a ferrous compound of Formula (B), or a salt or stereoisomer thereof, to provide a ferric compound of Formula (C), or a salt or stereoisomer thereof:

$N_3$—$R^1$  (A)

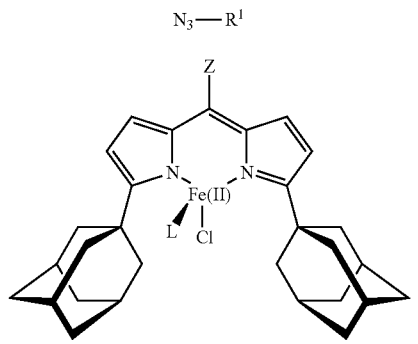
(B)

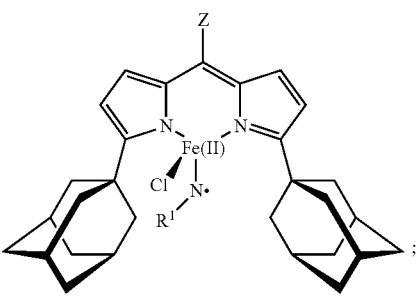
(C)

reacting the ferric compound of Formula (C), or a salt or stereoisomer thereof, with a compound of Formula (D) or (E), or a salt or stereoisomer thereof, to provide a compound of Formula (I), or a salt or stereoisomer thereof:

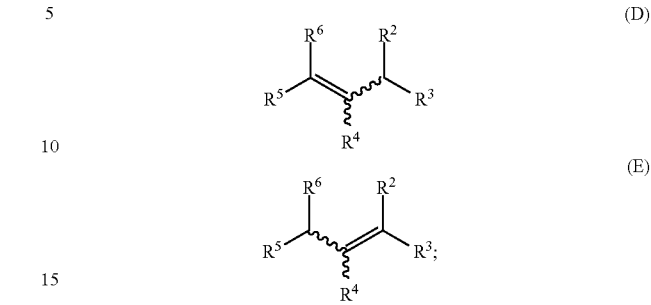

wherein:

Z is selected from the group consisting of mesityl and 2,6-dichlorophenyl;

$R^1$ is selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl;

each one of $R^2$, $R^3$, $R^4$, $R^5$, and $R^6$ is independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^a$, —$N(R^a)_2$, —$SR^a$, —CN, —C(=$NR^a$)$R^a$, —C(=$NR^a$)$OR^a$, —C(=$NR^a$)$N(R^a)_2$, —$NO_2$, —$NR^aC$(=O)$R^a$, —$NR^aC$(=O)$OR^a$, —$NR^aC$(=O)$N(R^a)_2$, —OC(=O)$R^a$, —OC(=O)$OR^a$, —OC(=O)$N(R^a)_2$, and —$ON(R^a)_2$;

optionally two of $R^2$, $R^3$, $R^4$, $R^5$, and $R^6$ groups are joined to form an optionally substituted carbocyclyl or optionally substituted heterocyclic ring;

each occurrence of $R^a$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally two $R^a$ groups are joined to form an optionally substituted heterocyclic ring;

L is selected from the group consisting of $N(R^b)_3$, $R^b$—O—$R^b$, $R^b$—S—$R^b$, optionally substituted heterocyclyl, and optionally substituted heteroaryl; and each occurrence of $R^b$ is independently selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl.

In compounds described herein, Z is selected from the group consisting of mesityl and 2,6-dichlorophenyl. In certain embodiments, Z is mesityl. In certain embodiments, Z is 2,6-dichlorophenyl.

In compounds of Formula (I), $R^1$ is a substituent on the nitrogen atom. In compounds of Formula (A), $R^1$ is a substituent on the azide group. In certain embodiments, $R^1$ is substituted alkyl. In certain embodiments, $R^1$ is unsubstituted alkyl. In certain embodiments, $R^1$ is $C_{1-6}$ alkyl. In certain embodiments, $R^1$ is methyl. In certain embodiments, $R^1$ is ethyl. In certain embodiments, $R^1$ is propyl. In certain embodiments, $R^1$ is butyl. In certain embodiments, $R^1$ is t-butyl. In certain embodiments, $R^1$ is Ad. In certain embodiments, $R^1$ is substituted alkenyl. In certain embodiments, $R^1$ is unsubstituted alkenyl. In certain embodiments, $R^1$ is vinyl. In certain embodiments, $R^1$ is substituted alkynyl. In certain embodiments, $R^1$ is unsubstituted alkynyl. In certain embodiments, $R^1$ is ethynyl. In certain embodiments, $R^1$ is substituted carbocyclyl. In certain embodiments, $R^1$ is unsubstituted carbocyclyl. In certain embodiments, $R^1$ is cyclopropyl. In certain embodiments, $R^1$ is cyclobutyl. In certain embodiments, $R^1$ is cyclopentyl. In certain embodiments, $R^1$ is cyclohexyl. In certain embodiments, $R^1$ is cycloheptyl. In certain embodiments, $R^1$ is substituted heterocyclyl. In certain embodiments, $R^1$ is unsubstituted heterocyclyl. In certain embodiments, $R^1$ is substituted aryl. In certain embodiments, $R^1$ is unsubstituted aryl. In certain embodiments, $R^1$ is substituted phenyl. In certain embodiments, $R^1$ is tolyl. In certain embodiments, $R^1$ is 4-tolyl. In certain embodiments, $R^1$ is Mes. In certain embodiments, $R^1$ is unsubstituted phenyl. In certain embodiments, $R^1$ is substituted naphthyl. In certain embodiments, $R^1$ is unsubstituted naphthyl. In certain embodiments, $R^1$ is substituted heteroaryl. In certain embodiments, $R^1$ is unsubstituted heteroaryl. In certain embodiments, $R^1$ is monocyclic heteroaryl. In certain embodiments, $R^1$ is 5-membered monocyclic heteroaryl. In certain embodiments, $R^1$ is 5-membered monocyclic heteroaryl, wherein only one of the five atoms in the ring of the heteroaryl is selected from the group consisting of nitrogen, oxygen, and sulfur. In certain embodiments, $R^1$ is 5-membered monocyclic heteroaryl, wherein only two of the five atoms in the ring of the heteroaryl are independently selected from the group consisting of nitrogen, oxygen, and sulfur. In certain embodiments, $R^1$ is 5-membered monocyclic heteroaryl, wherein only three of the five atoms in the ring of the heteroaryl are independently selected from the group consisting of nitrogen, oxygen, and sulfur. In certain embodiments, $R^1$ is tetrazolyl. In certain embodiments, $R^1$ is 6-membered monocyclic heteroaryl. In certain embodiments, $R^1$ is 6-membered monocyclic heteroaryl, wherein only one of the six atoms in the ring of the heteroaryl is selected from the group consisting of nitrogen, oxygen, and sulfur. In certain embodiments, $R^1$ is 6-membered monocyclic heteroaryl, wherein only two of the six atoms in the ring of the heteroaryl are independently selected from the group consisting of nitrogen, oxygen, and sulfur. In certain embodiments, $R^1$ is triazinyl. In certain embodiments, $R^1$ is tetrazinyl. In certain embodiments, $R^1$ is bicyclic heteroaryl, wherein the point of attachment may be at any atom of the heteroaryl, as valency permits. In certain embodiments, $R^1$ is a monocyclic heteroaryl fused with phenyl. In certain embodiments, $R^1$ is a 5-membered monocyclic heteroaryl fused with phenyl. In certain embodiments, $R^1$ is a 6-membered monocyclic heteroaryl fused with phenyl. In certain embodiments, $R^1$ is a monocyclic heteroaryl fused with another monocyclic heteroaryl. In certain embodiments, $R^1$ is a 5-membered monocyclic heteroaryl fused with another 5-membered monocyclic heteroaryl. In certain embodiments, $R^1$ is a 5-membered monocyclic heteroaryl fused with a 6-membered monocyclic heteroaryl. In certain embodiments, $R^1$ is a 6-membered monocyclic heteroaryl fused with another 6-membered monocyclic heteroaryl. In certain embodiments, $R^1$ is —C(=NR$^a$)R$^a$. In certain embodiments, $R^1$ is —C(=NR$^a$)OR$^a$. In certain embodiments, $R^1$ is —C(=NR$^a$)N(R$^a$)$_2$. In certain embodiments, $R^1$ is —C(=O)R$^a$. In certain embodiments, $R^1$ is —C(=O)OR$^a$. In certain embodiments, $R^1$ is —C(=O)N(R$^a$)$_2$. In certain embodiments, $R^1$ is a nitrogen protecting group. In certain embodiments, $R^1$ is Bn, Boc, Cbz, Fmoc, trifluoroacetyl, triphenylmethyl, or Ts.

Compounds of Formulae (I), (D), and (E) each include a substituent $R^2$. In certain embodiments, $R^2$ is H. In certain embodiments, $R^2$ is halogen. In certain embodiments, $R^2$ is F. In certain embodiments, $R^2$ is Cl. In certain embodiments, $R^2$ is Br. In certain embodiments, $R^2$ is I (iodine). In certain embodiments, $R^2$ is substituted acyl. In certain embodiments, $R^2$ is unsubstituted acyl. In certain embodiments, $R^2$ is —C(=O)R$^a$. In certain embodiments, $R^2$ is acetyl. In certain embodiments, $R^2$ is —C(=O)OR$^a$. In certain embodiments, $R^2$ is —C(=O)N(R$^a$)$_2$. In certain embodiments, $R^2$ is substituted alkyl. In certain embodiments, $R^2$ is unsubstituted alkyl. In certain embodiments, $R^2$ is $C_1$ alkyl. In certain embodiments, $R^2$ is methyl. In certain embodiments, $R^2$ is ethyl. In certain embodiments, $R^2$ is propyl. In certain embodiments, $R^2$ is butyl. In certain embodiments, $R^2$ is Ad. In certain embodiments, $R^2$ is substituted alkenyl. In certain embodiments, $R^2$ is unsubstituted alkenyl. In certain embodiments, $R^2$ is vinyl. In certain embodiments, $R^2$ is substituted alkynyl. In certain embodiments, $R^2$ is unsubstituted alkynyl. In certain embodiments, $R^2$ is ethynyl. In certain embodiments, $R^2$ is substituted carbocyclyl. In certain embodiments, $R^2$ is unsubstituted carbocyclyl. In certain embodiments, $R^2$ is cyclopropyl. In certain embodiments, $R^2$ is cyclobutyl. In certain embodiments, $R^2$ is cyclopentyl. In certain embodiments, $R^2$ is cyclohexyl. In certain embodiments, $R^2$ is cycloheptyl. In certain embodiments, $R^2$ is substituted heterocyclyl. In certain embodiments, $R^2$ is unsubstituted heterocyclyl. In certain embodiments, $R^2$ is substituted aryl. In certain embodiments, $R^2$ is unsubstituted aryl. In certain embodiments, $R^2$ is substituted phenyl. In certain embodiments, $R^2$ is unsubstituted phenyl. In certain embodiments, $R^2$ is substituted naphthyl. In certain embodiments, $R^2$ is unsubstituted naphthyl. In certain embodiments, $R^2$ is substituted heteroaryl. In certain embodiments, $R^2$ is unsubstituted heteroaryl. In certain embodiments, $R^2$ is monocyclic heteroaryl. In certain embodiments, $R^2$ is 5-membered monocyclic heteroaryl. In certain embodiments, $R^2$ is 5-membered monocyclic heteroaryl, wherein only one of the five atoms in the ring of the heteroaryl is selected from the group consisting of nitrogen, oxygen, and sulfur. In certain embodiments, $R^2$ is 5-membered monocyclic heteroaryl, wherein only two of the five atoms in the ring of the heteroaryl are independently selected from the group consisting of nitrogen, oxygen, and sulfur. In certain embodiments, $R^2$ is 5-membered monocyclic heteroaryl, wherein only three of the five atoms in the ring of the heteroaryl are independently selected from the group consisting of nitrogen, oxygen, and sulfur. In certain embodiments, $R^2$ is tetrazolyl. In certain embodiments, $R^2$ is 6-membered monocyclic heteroaryl. In certain embodiments, $R^2$ is 6-membered monocyclic heteroaryl, wherein only one of the six atoms in the ring of the heteroaryl is selected from the group consisting of nitrogen, oxygen, and sulfur. In certain embodiments, $R^2$ is 6-membered monocyclic heteroaryl, wherein only two of the six atoms in the ring of the heteroaryl are independently selected from the group consisting of nitrogen, oxygen, and sulfur. In certain embodiments, $R^2$ is triazinyl. In certain embodiments, $R^2$ is tetrazinyl. In certain embodiments, $R^2$ is bicyclic heteroaryl, wherein the point of attachment may be at any atom of the heteroaryl, as valency permits. In certain embodiments, $R^2$ is a monocyclic heteroaryl fused with phenyl. In certain embodiments, $R^2$ is a 5-membered monocyclic heteroaryl fused with phenyl. In certain embodiments, $R^2$ is a 6-membered monocyclic heteroaryl fused with phenyl. In certain embodiments, $R^2$ is a monocyclic heteroaryl fused with another monocyclic heteroaryl. In certain embodiments, $R^2$ is a 5-membered monocyclic heteroaryl fused with another 5-membered monocyclic heteroaryl. In certain embodiments, $R^2$ is a 5-membered monocyclic heteroaryl fused with a 6-membered monocyclic heteroaryl. In certain embodiments, $R^2$ is a 6-membered monocyclic heteroaryl fused with another 6-membered monocyclic heteroaryl. In certain embodiments, $R^2$ is —$OR^a$. In certain embodiments, $R^2$ is —OH when attached to an $sp^3$ carbon atom. In certain embodiments, $R^2$ is —$SR^a$. In certain embodiments, $R^2$ is —SH when attached to an $sp^3$ carbon atom. In certain embodiments, $R^2$ is —$N(R^a)_2$. In certain embodiments, $R^2$ is —$NH_2$ when attached to an $sp^3$ carbon atom. In certain embodiments, $R^2$ is —CN. In certain embodiments, $R^2$ is —SCN. In certain embodiments, $R^2$ is —$C(=NR^a)R^a$, —$C(=NR^a)OR^a$, or —$C(=NR^a)N(R^a)_2$. In certain embodiments, $R^2$ is —$C(=O)R^a$, —$C(=O)OR^a$, or —$C(=O)N(R^a)_2$. In certain embodiments, $R^2$ is —$NO_2$. In certain embodiments, $R^2$ is —$NR^aC(=O)R^a$, —$NR^aC(=O)OR^a$, or —$NR^aC(=O)N(R^a)_2$. In certain embodiments, $R^2$ is —$OC(=O)R^a$, —$OC(=O)OR^a$, or —$OC(=O)N(R^a)_2$. In certain embodiments, $R^2$ is —$ON(R^a)_2$.

Compounds of Formulae (I), (D), and (E) each include a substituent $R^3$. In certain embodiments, $R^3$ is H. In certain embodiments, $R^3$ is halogen. In certain embodiments, $R^3$ is F. In certain embodiments, $R^3$ is Cl. In certain embodiments, $R^3$ is Br. In certain embodiments, $R^3$ is I (iodine). In certain embodiments, $R^3$ is substituted acyl. In certain embodiments, $R^3$ is unsubstituted acyl. In certain embodiments, $R^3$ is —$C(=O)R^a$. In certain embodiments, $R^3$ is acetyl. In certain embodiments, $R^3$ is —$C(=O)OR^a$. In certain embodiments, $R^3$ is —$C(=O)N(R^a)_2$. In certain embodiments, $R^3$ is substituted alkyl. In certain embodiments, $R^3$ is unsubstituted alkyl. In certain embodiments, $R^3$ is $C_{1-6}$ alkyl. In certain embodiments, $R^3$ is methyl. In certain embodiments, $R^3$ is ethyl. In certain embodiments, $R^3$ is propyl. In certain embodiments, $R^3$ is butyl. In certain embodiments, $R^3$ is Ad. In certain embodiments, $R^3$ is substituted alkenyl. In certain embodiments, $R^3$ is unsubstituted alkenyl. In certain embodiments, $R^3$ is vinyl. In certain embodiments, $R^3$ is substituted alkynyl. In certain embodiments, $R^3$ is unsubstituted alkynyl. In certain embodiments, $R^3$ is ethynyl. In certain embodiments, $R^3$ is substituted carbocyclyl. In certain embodiments, $R^3$ is unsubstituted carbocyclyl. In certain embodiments, $R^3$ is cyclopropyl. In certain embodiments, $R^3$ is cyclobutyl. In certain embodiments, $R^3$ is cyclopentyl. In certain embodiments, $R^3$ is cyclohexyl. In certain embodiments, $R^3$ is cycloheptyl. In certain embodiments, $R^3$ is substituted heterocyclyl. In certain embodiments, $R^3$ is unsubstituted heterocyclyl. In certain embodiments, $R^3$ is substituted aryl. In certain embodiments, $R^3$ is unsubstituted aryl. In certain embodiments, $R^3$ is substituted phenyl. In certain embodiments, $R^3$ is unsubstituted phenyl. In certain embodiments, $R^3$ is substituted naphthyl. In certain embodiments, $R^3$ is unsubstituted naphthyl. In certain embodiments, $R^3$ is substituted heteroaryl. In certain embodiments, $R^3$ is unsubstituted heteroaryl. In certain embodiments, $R^3$ is monocyclic heteroaryl. In certain embodiments, $R^3$ is 5-membered monocyclic heteroaryl. In certain embodiments, $R^3$ is 5-membered monocyclic heteroaryl, wherein only one of the five atoms in the ring of the heteroaryl is selected from the group consisting of nitrogen, oxygen, and sulfur. In certain embodiments, $R^3$ is 5-membered monocyclic heteroaryl, wherein only two of the five atoms in the ring of the heteroaryl are independently selected from the group consisting of nitrogen, oxygen, and sulfur. In certain embodiments, $R^3$ is 5-membered monocyclic heteroaryl, wherein only three of the five atoms in the ring of the heteroaryl are independently selected from the group consisting of nitrogen, oxygen, and sulfur. In certain embodiments, $R^3$ is tetrazolyl. In certain embodiments, $R^3$ is 6-membered monocyclic heteroaryl. In certain embodiments, $R^3$ is 6-membered monocyclic heteroaryl, wherein only one of the six atoms in the ring of the heteroaryl is selected from the group consisting of nitrogen, oxygen, and sulfur. In certain embodiments, $R^3$ is 6-membered monocyclic heteroaryl, wherein only two of the six atoms in the ring of the heteroaryl are independently selected from the group consisting of nitrogen, oxygen, and sulfur. In certain embodiments, $R^3$ is triazinyl. In certain embodiments, $R^3$ is tetrazinyl. In certain embodiments, $R^3$ is bicyclic heteroaryl, wherein the point of attachment may be at any atom of the heteroaryl, as valency permits. In certain embodiments, $R^3$ is a monocyclic heteroaryl fused with phenyl. In certain embodiments, $R^3$ is a 5-membered monocyclic heteroaryl fused with phenyl. In certain embodiments, $R^3$ is a 6-membered monocyclic heteroaryl fused with phenyl. In certain embodiments, $R^3$ is a monocyclic heteroaryl fused with another monocyclic heteroaryl. In certain embodiments, $R^3$ is a 5-membered monocyclic heteroaryl fused with another 5-membered monocyclic heteroaryl. In certain embodiments, $R^3$ is a 5-membered monocyclic heteroaryl fused with a 6-membered monocyclic heteroaryl. In certain embodiments, $R^3$ is a 6-membered monocyclic heteroaryl fused with another 6-membered monocyclic heteroaryl. In certain embodiments, $R^3$ is —$OR^a$. In certain embodiments, $R^3$ is —OH when attached to an $sp^3$ carbon atom. In certain embodiments, $R^3$ is —$SR^a$. In certain embodiments, $R^3$ is —SH when attached to an $sp^3$ carbon atom. In certain embodiments, $R^3$ is —$N(R^a)_2$. In certain embodiments, $R^3$ is —$NH_2$ when attached to an $sp^3$ carbon atom. In certain embodiments, $R^3$ is —CN. In certain embodiments, $R^3$ is —SCN. In certain embodiments, $R^3$ is —$C(=NR^a)R^a$, —$C(=NR^a)OR^a$, or —$C(=NR^a)N(R^a)_2$. In certain embodiments, $R^3$ is —$C(=O)R^a$, —$C(=O)OR^a$, or —$C(=O)N(R^a)_2$. In certain embodiments, $R^3$ is —$NO_2$. In certain embodiments, $R^3$ is —$NR^aC(=O)R^a$, —$NR^aC(=O)OR^a$, or —$NR^aC(=O)N(R^a)_2$. In certain embodiments, $R^3$ is —$OC(=O)R^a$, —$OC(=O)OR^a$, or —$OC(=O)N(R^a)_2$. In certain embodiments, $R^3$ is —$ON(R^a)_2$.

Compounds of Formulae (I), (D), and (E) each include a substituent $R^4$. In certain embodiments, $R^4$ is H. In certain embodiments, $R^4$ is halogen. In certain embodiments, $R^4$ is F. In certain embodiments, $R^4$ is Cl. In certain embodiments, $R^4$ is Br. In certain embodiments, $R^4$ is I (iodine). In certain embodiments, $R^4$ is substituted acyl. In certain embodiments, $R^4$ is unsubstituted acyl. In certain embodiments, $R^4$ is —$C(=O)R^a$. In certain embodiments, $R^4$ is acetyl. In certain embodiments, $R^4$ is —$C(=O)OR^a$. In certain embodiments, $R^4$ is —$C(=O)N(R^a)_2$. In certain embodiments, $R^4$ is substituted alkyl. In certain embodiments, $R^4$ is unsubstituted alkyl. In certain embodiments, $R^4$ is $C_{1-6}$ alkyl. In certain embodiments, $R^4$ is methyl. In certain embodiments, $R^4$ is ethyl. In certain embodiments, $R^4$ is propyl. In certain embodiments, $R^4$ is butyl. In certain embodiments, $R^4$ is Ad. In certain embodiments, $R^4$ is substituted alkenyl. In certain embodiments, $R^4$ is unsubstituted alkenyl. In certain embodiments, $R^4$ is vinyl. In certain embodiments, $R^4$ is substituted alkynyl. In certain embodiments, $R^4$ is unsubstituted alkynyl. In certain embodiments, $R^4$ is ethynyl. In certain embodiments, $R^4$ is substituted carbocyclyl. In certain embodiments, $R^4$ is unsubstituted carbocyclyl. In certain embodiments, $R^4$ is cyclopropyl. In certain embodiments, $R^4$ is cyclobutyl. In certain embodiments, $R^4$ is cyclopentyl. In certain embodiments, $R^4$ is cyclohexyl. In certain embodiments, $R^4$ is cycloheptyl. In certain embodiments, $R^4$ is substituted heterocyclyl. In certain embodiments, $R^4$ is unsubstituted heterocyclyl. In certain embodiments, $R^4$ is substituted aryl. In certain embodiments, $R^4$ is unsubstituted aryl. In certain embodiments, $R^4$ is substituted phenyl. In certain embodiments, $R^4$ is unsubstituted phenyl. In certain embodiments, $R^4$ is substituted naphthyl. In certain embodiments, $R^4$ is unsubstituted naphthyl. In certain embodiments, $R^4$ is substituted heteroaryl. In certain embodiments, $R^4$ is unsubstituted heteroaryl. In certain embodiments, $R^4$ is monocyclic heteroaryl. In certain embodiments, $R^4$ is 5-membered monocyclic heteroaryl. In certain embodiments, $R^4$ is 5-membered monocyclic heteroaryl, wherein only one of the five atoms in the ring of the heteroaryl is selected from the group consisting of nitrogen, oxygen, and sulfur. In certain embodiments, $R^4$ is 5-membered monocyclic heteroaryl, wherein only two of the five atoms in the ring of the heteroaryl are independently selected from the group consisting of nitrogen, oxygen, and sulfur. In certain embodiments, $R^4$ is 5-membered monocyclic heteroaryl, wherein only three of the five atoms in the ring of the heteroaryl are independently selected from the group consisting of nitrogen, oxygen, and sulfur. In certain embodiments, $R^4$ is tetrazolyl. In certain embodiments, $R^4$ is 6-membered monocyclic heteroaryl. In certain embodiments, $R^4$ is 6-membered monocyclic heteroaryl, wherein only one of the six atoms in the ring of the heteroaryl is selected from the group consisting of nitrogen, oxygen, and sulfur. In certain embodiments, $R^4$ is 6-membered monocyclic heteroaryl, wherein only two of the six atoms in the ring of the heteroaryl are independently selected from the group consisting of nitrogen, oxygen, and sulfur. In certain embodiments, $R^4$ is triazinyl. In certain embodiments, $R^4$ is tetrazinyl. In certain embodiments, $R^4$ is bicyclic heteroaryl, wherein the point of attachment may be at any atom of the heteroaryl, as valency permits. In certain embodiments, $R^4$ is a monocyclic heteroaryl fused with phenyl. In certain embodiments, $R^4$ is a 5-membered monocyclic heteroaryl fused with phenyl. In certain embodiments, $R^4$ is a 6-membered monocyclic heteroaryl fused with phenyl. In certain embodiments, $R^4$ is a monocyclic heteroaryl fused with another monocyclic heteroaryl. In certain embodiments, $R^4$ is a 5-membered monocyclic heteroaryl fused with another 5-membered monocyclic heteroaryl. In certain embodiments, $R^4$ is a 5-membered monocyclic heteroaryl fused with a 6-membered monocyclic heteroaryl. In certain embodiments, $R^4$ is a 6-membered monocyclic heteroaryl fused with another 6-membered monocyclic heteroaryl. In certain embodiments, $R^4$ is —$OR^a$. In certain embodiments, $R^4$ is —OH when attached to an sp$^3$ carbon atom. In certain embodiments, $R^4$ is —$SR^a$. In certain embodiments, $R^4$ is —SH when attached to an sp$^3$ carbon atom. In certain embodiments, $R^4$ is —$N(R^a)_2$. In certain embodiments, $R^4$ is —$NH_2$ when attached to an sp$^3$ carbon atom. In certain embodiments, $R^4$ is —CN. In certain embodiments, $R^4$ is —SCN. In certain embodiments, $R^4$ is —$C(=NR^a)R^a$, —$C(=NR^a)OR^a$, or —$C(=NR^a)N(R^a)_2$. In certain embodiments, $R^4$ is —$C(=O)R^a$, —$C(=O)OR^a$, or —$C(=O)N(R^a)_2$. In certain embodiments, $R^4$ is —$NO_2$. In certain embodiments, $R^4$ is —$NR^aC(=O)R^a$, —$NR^aC(=O)OR^a$, or —$NR^aC(=O)N(R^a)_2$. In certain embodiments, $R^4$ is —$OC(=O)R^a$, —$OC(=O)OR^a$, or —$OC(=O)N(R^a)_2$. In certain embodiments, $R^4$ is —$ON(R^a)_2$.

Compounds of Formulae (I), (D), and (E) each include a substituent $R^5$. In certain embodiments, $R^5$ is H. In certain embodiments, $R^5$ is halogen. In certain embodiments, $R^5$ is F. In certain embodiments, $R^5$ is Cl. In certain embodiments, $R^5$ is Br. In certain embodiments, $R^5$ is I (iodine). In certain embodiments, $R^5$ is substituted acyl. In certain embodiments, $R^5$ is unsubstituted acyl. In certain embodiments, $R^5$ is —$C(=O)R^a$. In certain embodiments, $R^5$ is acetyl. In certain embodiments, $R^5$ is —$C(=O)OR^a$. In certain embodiments, $R^5$ is —$C(=O)N(R^a)_2$. In certain embodiments, $R^5$ is substituted alkyl. In certain embodiments, $R^5$ is unsubstituted alkyl. In certain embodiments, $R^5$ is $C_{1-6}$ alkyl. In certain embodiments, $R^5$ is methyl. In certain embodiments, $R^5$ is ethyl. In certain embodiments, $R^5$ is propyl. In certain embodiments, $R^5$ is butyl. In certain embodiments, $R^5$ is Ad. In certain embodiments, $R^5$ is substituted alkenyl. In certain embodiments, $R^5$ is unsubstituted alkenyl. In certain embodiments, $R^5$ is vinyl. In certain embodiments, $R^5$ is substituted alkynyl. In certain embodiments, $R^5$ is unsubstituted alkynyl. In certain embodiments, $R^5$ is ethynyl. In certain embodiments, $R^5$ is substituted carbocyclyl. In certain embodiments, $R^5$ is unsubstituted carbocyclyl. In certain embodiments, $R^5$ is cyclopropyl. In certain embodiments, $R^5$ is cyclobutyl. In certain embodiments, $R^5$ is cyclopentyl. In certain embodiments, $R^5$ is cyclohexyl. In certain embodiments, $R^5$ is cycloheptyl. In certain embodiments, $R^5$ is substituted heterocyclyl. In certain embodiments, $R^5$ is unsubstituted heterocyclyl. In certain embodiments, $R^5$ is substituted aryl. In certain embodiments, $R^5$ is unsubstituted aryl. In certain embodiments, $R^5$ is substituted phenyl. In certain embodiments, $R^5$ is unsubstituted phenyl. In certain embodiments, $R^5$ is substituted naphthyl. In certain embodiments, $R^5$ is unsubstituted naphthyl. In certain embodiments, $R^5$ is substituted heteroaryl. In certain embodiments, $R^5$ is unsubstituted heteroaryl. In certain embodiments, $R^5$ is monocyclic heteroaryl. In certain embodiments, $R^5$ is 5-membered monocyclic heteroaryl. In certain embodiments, $R^5$ is 5-membered monocyclic heteroaryl, wherein only one of the five atoms in the ring of the heteroaryl is selected from the group consisting of nitrogen, oxygen, and sulfur. In certain embodiments, $R^5$ is 5-membered monocyclic heteroaryl, wherein only two of the five atoms in the ring of the heteroaryl are independently selected from the group consisting of nitrogen, oxygen, and sulfur. In certain embodiments, $R^5$ is 5-membered monocyclic heteroaryl, wherein only three of the five atoms in the ring of the heteroaryl are independently selected from the group consisting of nitrogen, oxygen, and sulfur. In certain embodiments, $R^5$ is tetrazolyl. In certain embodiments, $R^5$ is 6-membered monocyclic heteroaryl. In certain embodiments, $R^5$ is 6-membered monocyclic heteroaryl, wherein only one of the six atoms in the ring of the heteroaryl is selected from the group consisting of nitrogen, oxygen, and sulfur. In certain embodiments, $R^5$ is 6-membered monocyclic heteroaryl, wherein only two of the six atoms in the ring of the heteroaryl are independently selected from the group consisting of nitrogen, oxygen, and sulfur. In certain embodiments, $R^5$ is triazinyl. In certain embodiments, $R^5$ is tetrazinyl. In certain embodiments, $R^5$ is bicyclic heteroaryl, wherein the point of attachment may be at any atom of the heteroaryl, as valency permits. In certain embodiments, $R^5$ is a monocyclic heteroaryl fused with phenyl. In certain embodiments, $R^5$ is a 5-membered monocyclic heteroaryl fused with phenyl. In certain embodiments, $R^5$ is a 6-membered monocyclic heteroaryl fused with phenyl. In certain embodiments, $R^5$ is a monocyclic heteroaryl fused with another monocyclic heteroaryl. In certain embodiments, $R^5$ is a 5-membered monocyclic heteroaryl fused with another 5-membered monocyclic heteroaryl. In certain embodiments, $R^5$ is a 5-membered monocyclic heteroaryl fused with a 6-membered monocyclic heteroaryl. In certain embodiments, $R^5$ is a 6-membered monocyclic heteroaryl fused with another 6-membered monocyclic heteroaryl. In certain embodiments, $R^5$ is —$OR^a$. In certain embodiments, $R^5$ is —OH when attached to an $sp^3$ carbon atom. In certain embodiments, $R^5$ is —$SR^a$. In certain embodiments, $R^5$ is —SH when attached to an $sp^3$ carbon atom. In certain embodiments, $R^5$ is —$N(R^a)_2$. In certain embodiments, $R^5$ is —$NH_2$ when attached to an $sp^3$ carbon atom. In certain embodiments, $R^5$ is —CN. In certain embodiments, $R^5$ is —SCN. In certain embodiments, $R^5$ is —$C(=NR^a)R^a$, —$C(=NR^a)OR^a$, or —$C(=NR^a)N(R^a)_2$. In certain embodiments, $R^5$ is —$C(=O)R^a$, —$C(=O)OR^a$, or —$C(=O)N(R^a)_2$. In certain embodiments, $R^5$ is —$NO_2$. In certain embodiments, $R^5$ is —$NR^aC(=O)R^a$, —$NR^aC(=O)OR^a$, or —$NR^aC(=O)N(R^a)_2$. In certain embodiments, $R^5$ is —$OC(=O)R^a$, —$OC(=O)OR^a$, or —$OC(=O)N(R^a)_2$. In certain embodiments, $R^5$ is —$ON(R^a)_2$.

Compounds of Formulae (I), (D), and (E) each include a substituent $R^6$. In certain embodiments, $R^6$ is H. In certain embodiments, $R^6$ is halogen. In certain embodiments, $R^6$ is F. In certain embodiments, $R^6$ is Cl. In certain embodiments, $R^6$ is Br. In certain embodiments, $R^6$ is I (iodine). In certain embodiments, $R^6$ is substituted acyl. In certain embodiments, $R^6$ is unsubstituted acyl. In certain embodiments, $R^6$ is —$C(=O)R^a$. In certain embodiments, $R^6$ is acetyl. In certain embodiments, $R^6$ is —$C(=O)OR^a$. In certain embodiments, $R^6$ is —$C(=O)N(R^a)_2$. In certain embodiments, $R^6$ is substituted alkyl. In certain embodiments, $R^6$ is unsubstituted alkyl. In certain embodiments, $R^6$ is $C_{1-6}$ alkyl. In certain embodiments, $R^6$ is methyl. In certain embodiments, $R^6$ is ethyl. In certain embodiments, $R^6$ is propyl. In certain embodiments, $R^6$ is butyl. In certain embodiments, $R^6$ is Ad. In certain embodiments, $R^6$ is substituted alkenyl. In certain embodiments, $R^6$ is unsubstituted alkenyl. In certain embodiments, $R^6$ is vinyl. In certain embodiments, $R^6$ is substituted alkynyl. In certain embodiments, $R^6$ is unsubstituted alkynyl. In certain embodiments, $R^6$ is ethynyl. In certain embodiments, $R^6$ is substituted carbocyclyl. In certain embodiments, $R^6$ is unsubstituted carbocyclyl. In certain embodiments, $R^6$ is cyclopropyl. In certain embodiments, $R^6$ is cyclobutyl. In certain embodiments, $R^6$ is cyclopentyl. In certain embodiments, $R^6$ is cyclohexyl. In certain embodiments, $R^6$ is cycloheptyl. In certain embodiments, $R^6$ is substituted heterocyclyl. In certain embodiments, $R^6$ is unsubstituted heterocyclyl. In certain embodiments, $R^6$ is substituted aryl. In certain embodiments, $R^6$ is unsubstituted aryl. In certain embodiments, $R^6$ is substituted phenyl. In certain embodiments, $R^6$ is unsubstituted phenyl. In certain embodiments, $R^6$ is substituted naphthyl. In certain embodiments, $R^6$ is unsubstituted naphthyl. In certain embodiments, $R^6$ is substituted heteroaryl. In certain embodiments, $R^6$ is unsubstituted heteroaryl. In certain embodiments, $R^6$ is monocyclic heteroaryl. In certain embodiments, $R^6$ is 5-membered monocyclic heteroaryl. In certain embodiments, $R^6$ is 5-membered monocyclic heteroaryl, wherein only one of the five atoms in the ring of the heteroaryl is selected from the group consisting of nitrogen, oxygen, and sulfur. In certain embodiments, $R^6$ is 5-membered monocyclic heteroaryl, wherein only two of the five atoms in the ring of the heteroaryl are independently selected from the group consisting of nitrogen, oxygen, and sulfur. In certain embodiments, $R^6$ is 5-membered monocyclic heteroaryl, wherein only three of the five atoms in the ring of the heteroaryl are independently selected from the group consisting of nitrogen, oxygen, and sulfur. In certain embodiments, $R^6$ is tetrazolyl. In certain embodiments, $R^6$ is 6-membered monocyclic heteroaryl. In certain embodiments, $R^6$ is 6-membered monocyclic heteroaryl, wherein only one of the six atoms in the ring of the heteroaryl is selected from the group consisting of nitrogen, oxygen, and sulfur. In certain embodiments, $R^6$ is 6-membered monocyclic heteroaryl, wherein only two of the six atoms in the ring of the heteroaryl are independently selected from the group consisting of nitrogen, oxygen, and sulfur. In certain embodiments, $R^6$ is triazinyl. In certain embodiments, $R^6$ is tetrazinyl. In certain embodiments, $R^6$ is bicyclic heteroaryl, wherein the point of attachment may be at any atom of the heteroaryl, as valency permits. In certain embodiments, $R^6$ is a monocyclic heteroaryl fused with phenyl. In certain embodiments, $R^6$ is a 5-membered monocyclic heteroaryl fused with phenyl. In certain embodiments, $R^6$ is a 6-membered monocyclic heteroaryl fused with phenyl. In certain embodiments, $R^6$ is a monocyclic heteroaryl fused with another monocyclic heteroaryl. In certain embodiments, $R^6$ is a 5-membered monocyclic heteroaryl fused with another 5-membered monocyclic heteroaryl. In certain embodiments, $R^6$ is a 5-membered monocyclic heteroaryl fused with a 6-membered monocyclic heteroaryl. In certain embodiments, $R^6$ is a 6-membered monocyclic heteroaryl fused with another 6-membered monocyclic heteroaryl. In certain embodiments, $R^6$ is —$OR^a$. In certain embodiments, $R^6$ is —OH when attached to an $sp^3$ carbon atom. In certain embodiments, $R^6$ is —$SR^a$. In certain embodiments, $R^6$ is —SH when attached to an $sp^3$ carbon atom. In certain embodiments, $R^6$ is —$N(R^a)_2$. In certain embodiments, $R^6$ is —$NH_2$ when attached to an $sp^3$ carbon atom. In certain embodiments, $R^6$ is —CN. In certain embodiments, $R^6$ is —SCN. In certain embodiments, $R^6$ is —$C(=NR^a)R^a$, —$C(=NR^a)OR^a$, or —$C(=NR^a)N(R^a)_2$. In certain embodiments, $R^6$ is —$C(=O)R^a$, —$C(=O)OR^a$, or —$C(=O)N(R^a)_2$. In certain embodiments, $R^6$ is —$NO_2$. In certain embodiments, $R^6$ is —$NR^aC(=O)R^a$, —$NR^aC(=O)OR^a$, or —$NR^aC(=O)N(R^a)_2$. In certain embodiments, $R^6$ is —$OC(=O)R^a$, —$OC(=O)OR^a$, or —$OC(=O)N(R^a)_2$. In certain embodiments, $R^6$ is —$ON(R^a)_2$.

In certain embodiments, at least one $R^a$ is H. In certain embodiments, at least one $R^a$ is substituted acyl. In certain embodiments, at least one $R^a$ is unsubstituted acyl. In certain embodiments, at least one $R^a$ is acetyl. In certain embodiments, at least one $R^a$ is substituted alkyl. In certain embodiments, at least one $R^a$ is unsubstituted alkyl. In certain embodiments, at least one $R^a$ is $C_{1-6}$ alkyl. In certain embodiments, at least one $R^a$ is methyl. In certain embodiments, at least one $R^a$ is ethyl. In certain embodiments, at least one $R^a$ is propyl. In certain embodiments, at least one $R^a$ is butyl. In certain embodiments, at least one $R^a$ is substituted alkenyl. In certain embodiments, at least one $R^a$ is unsubstituted alkenyl. In certain embodiments, at least one $R^a$ is vinyl. In certain embodiments, at least one $R^a$ is substituted alkynyl. In certain embodiments, at least one $R^a$ is unsubstituted alkynyl. In certain embodiments, at least one $R^a$ is ethynyl. In certain embodiments, at least one $R^a$ is substituted carbocyclyl. In certain embodiments, at least one $R^a$ is unsubstituted carbocyclyl. In certain embodiments, at least one $R^a$ is cyclopropyl. In certain embodiments, at least one $R^a$ is cyclobutyl. In certain embodiments, at least one $R^a$ is cyclopentyl. In certain embodiments, at least one $R^a$ is cyclohexyl. In certain embodiments, at least one $R^a$ is cycloheptyl. In certain embodiments, at least one $R^a$ is substituted heterocyclyl. In certain embodiments, at least one $R^a$ is unsubstituted heterocyclyl. In certain embodiments, at least one $R^a$ is substituted aryl. In certain embodiments, at least one $R^a$ is unsubstituted aryl. In certain embodiments, at least one $R^a$ is substituted phenyl. In certain embodiments, at least one $R^a$ is unsubstituted phenyl. In certain embodiments, at least one $R^a$ is substituted heteroaryl. In certain embodiments, at least one $R^a$ is unsubstituted heteroaryl. In certain embodiments, at least one $R^a$ is substituted pyridyl. In certain embodiments, at least one $R^a$ is unsubstituted pyridyl. In certain embodiments, at least one $R^a$ is a nitrogen protecting group when attached to a nitrogen atom. In certain embodiments, at least one $R^a$ is Bn, Boc, Cbz, Fmoc, trifluoroacetyl, triphenylmethyl, or Ts when attached to a nitrogen atom. In certain embodiments, at least one $R^a$ is an oxygen protecting group when attached to an oxygen atom. In certain embodiments, at least one $R^a$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, two $R^a$ groups are joined to form a substituted heterocyclic ring. In certain embodiments, two $R^a$ groups are joined to form an unsubstituted heterocyclic ring. In certain embodiments, two $R^a$ groups are joined to form a substituted heteroaryl ring. In certain embodiments, two $R^a$ groups are joined to form an unsubstituted heteroaryl ring. In certain embodiments, —$OR^a$ is not —OH when —$OR^a$ is attached to a carbon atom of a C=C bond. In certain embodiments, —$N(R^a)_2$ is not —$NH_2$ when —$N(R^a)_2$ is attached to a carbon atom of a C=C bond. In certain embodiments, —$SR^a$ is not —SH when —$SR^a$ is attached to a carbon atom of a C=C bond.

In compounds of Formulae (I), (D), and (E), any two of $R^2$, $R^3$, $R^4$, $R^5$, and $R^6$ groups may be joined to form a optionally substituted carbocyclyl ring or optionally substituted heterocyclic ring. In certain embodiments, $R^2$ and $R^3$ are joined to form a optionally substituted carbocyclyl ring. In certain embodiments, $R^2$ and $R^3$ are joined to form a optionally substituted heterocyclic ring. In certain embodiments, $R^2$ and $R^4$ are joined to form a optionally substituted carbocyclyl ring. In certain embodiments, $R^2$ and $R^4$ are joined to form a optionally substituted heterocyclic ring. In certain embodiments, $R^2$ and $R^5$ are joined to form a optionally substituted carbocyclyl ring. In certain embodiments, $R^2$ and $R^5$ are joined to form a optionally substituted heterocyclic ring. In certain embodiments, $R^2$ and $R^6$ are joined to form a optionally substituted carbocyclyl ring. In certain embodiments, $R^2$ and $R^6$ are joined to form a optionally substituted heterocyclic ring. In certain embodiments, $R^3$ and $R^4$ are joined to form a optionally substituted carbocyclyl ring. In certain embodiments, $R^3$ and $R^4$ are joined to form a optionally substituted heterocyclic ring. In certain embodiments, $R^3$ and $R^5$ are joined to form a optionally substituted carbocyclyl ring. In certain embodiments, $R^3$ and $R^5$ are joined to form a optionally substituted heterocyclic ring. In certain embodiments, $R^3$ and $R^6$ are joined to form a optionally substituted carbocyclyl ring. In certain embodiments, $R^3$ and $R^6$ are joined to form a optionally substituted heterocyclic ring. In certain embodiments, $R^4$ and $R^5$ are joined to form a optionally substituted carbocyclyl ring. In certain embodiments, $R^4$ and $R^5$ are joined to form a optionally substituted heterocyclic ring. In certain embodiments, $R^4$ and $R^6$ are joined to form a optionally substituted carbocyclyl ring. In certain embodiments, $R^4$ and $R^6$ are joined to form a optionally substituted heterocyclic ring. In certain embodiments, $R^5$ and $R^6$ are joined to form a optionally substituted carbocyclyl ring. In certain embodiments, $R^5$ and $R^6$ are joined to form a optionally substituted heterocyclic ring.

In compounds of Formulae (I), (D), and (E) ⁓ represents a single bond with any stereochemistry (e.g., geometric isomer). In certain embodiments, in compounds of Formulae (I) and (D), $R^4$ is cis to $R^5$ and trans to $R^6$. In certain embodiments, in compounds of Formulae (I) and (D), $R^4$ is trans to $R^5$ and cis to $R^6$. In certain embodiments, in compounds of Formula (E), $R^4$ is cis to $R^2$ and trans to $R^3$. In certain embodiments, in compounds of Formula (E), $R^4$ is trans to $R^2$ and cis to $R^3$.

In certain embodiments, $R^2$ and $R^3$ are each hydrogen. In certain embodiments, $R^2$ and $R^3$ are each hydrogen; and $R^5$ or $R^6$ is optionally substituted alkyl. In certain embodiments, $R^2$ and $R^3$ are each hydrogen; and $R^5$ or $R^6$ is $C_{1-12}$ alkyl. In certain embodiments, $R^2$ and $R^3$ are each hydrogen; and $R^5$ or $R^6$ is $C_{1-6}$ alkyl. In certain embodiments, $R^2$ and $R^3$ are each hydrogen; and $R^5$ or $R^6$ is optionally substituted aryl. In certain embodiments, $R^2$ and $R^3$ are each hydrogen; and $R^5$ or $R^6$ is optionally substituted phenyl. In certain embodiments, $R^2$ and $R^3$ are each hydrogen; and $R^5$ or $R^6$ is phenyl.

In certain embodiments, $R^2$, $R^3$, and $R^4$ are each hydrogen. In certain embodiments, $R^2$, $R^3$, and $R^4$ are each hydrogen; and $R^5$ or $R^6$ is optionally substituted alkyl. In certain embodiments, $R^2$, $R^3$, and $R^4$ are each hydrogen; and $R^5$ or $R^6$ is $C_{1-12}$ alkyl. In certain embodiments, $R^2$, $R^3$, and $R^4$ are each hydrogen; and $R^5$ or $R^6$ is $C_{1-6}$ alkyl. In certain embodiments, $R^2$, $R^3$, and $R^4$ are each hydrogen; and $R^5$ or $R^6$ is optionally substituted aryl. In certain embodiments, $R^2$, $R^3$, and $R^4$ are each hydrogen; and $R^5$ or $R^6$ is optionally substituted phenyl. In certain embodiments, $R^2$, $R^3$, and $R^4$ are each hydrogen; and $R^5$ or $R^6$ is phenyl.

In certain embodiments, $R^2$, $R^3$, $R^4$, and $R^5$ are each hydrogen. In certain embodiments, $R^2$, $R^3$, $R^4$, and $R^5$ are each hydrogen; and $R^6$ is optionally substituted alkyl. In certain embodiments, $R^2$, $R^3$, $R^4$, and $R^5$ are each hydrogen; and $R^6$ is $C_{1-12}$ alkyl. In certain embodiments, $R^2$, $R^3$, $R^4$, and $R^5$ are each hydrogen; and $R^6$ is $C_{1-6}$ alkyl. In certain embodiments, $R^2$, $R^3$, $R^4$, and $R^5$ are each hydrogen; and $R^6$ is optionally substituted alkenyl. In certain embodiments, $R^2$, $R^3$, $R^4$, and $R^5$ are each hydrogen; and $R^6$ is $C_{1-12}$ alkenyl. In certain embodiments, $R^2$, $R^3$, $R^4$, and $R^5$ are each hydrogen; and $R^6$ is $C_{1-6}$ alkenyl. In certain embodiments, $R^2$, $R^3$, $R^4$, and $R^5$ are each hydrogen; and $R^6$ is optionally substituted alkynyl. In certain embodiments, $R^2$, $R^3$, $R^4$, and $R^5$ are each hydrogen; and $R^6$ is $C_{1-12}$ alkynyl. In certain embodiments, $R^2$, $R^3$, $R^4$, and $R^5$ are each hydrogen; and $R^6$ is $C_{1-6}$ alkynyl. In certain embodiments, $R^2$, $R^3$, $R^4$, and $R^5$ are each hydrogen; and $R^6$ is optionally substituted aryl. In certain embodiments, $R^2$, $R^3$, $R^4$, and $R^5$ are each hydrogen; and $R^6$ is optionally substituted phenyl. In certain embodiments, $R^2$, $R^3$, $R^4$, and $R^5$ are each hydrogen; and $R^6$ is phenyl. In certain embodiments, $R^2$, $R^3$, $R^4$, and $R^5$ are each hydrogen; and $R^6$ is optionally substituted heteroaryl.

In certain embodiments, $R^2$, $R^3$, $R^4$, and $R^6$ are each hydrogen. In certain embodiments, $R^2$, $R^3$, $R^4$, and $R^6$ are each hydrogen; and $R^5$ is optionally substituted alkyl. In certain embodiments, $R^2$, $R^3$, $R^4$, and $R^6$ are each hydrogen; and $R^5$ is $C_{1-12}$ alkyl. In certain embodiments, $R^2$, $R^3$, $R^4$, and $R^6$ are each hydrogen; and $R^5$ is $C_{1-6}$ alkyl. In certain embodiments, $R^2$, $R^3$, $R^4$, and $R^6$ are each hydrogen; and $R^5$ is optionally substituted aryl. In certain embodiments, $R^2$, $R^3$, $R^4$, and $R^6$ are each hydrogen; and $R^5$ is optionally substituted phenyl. In certain embodiments, $R^2$, $R^3$, $R^4$, and $R^6$ are each hydrogen; and $R^5$ is phenyl.

In certain embodiments, the compound of Formula (D) is of the formula:

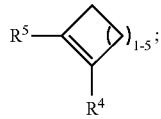

and the compound of Formula (I) is of the formula:

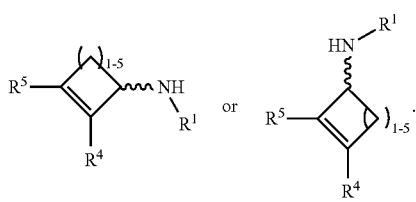

In certain embodiments, the compound of Formula (D) is of the formula:

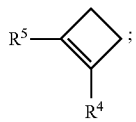

and the compound of Formula (I) is of the formula:

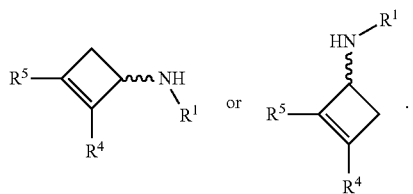

In certain embodiments, the compound of Formula (D) is of the formula:

and the compound of the Formula (I) is of the formula:

In certain embodiments, the compound of Formula (D) is of the formula:

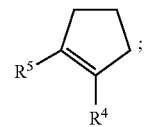

and the compound of the Formula (I) is of the formula:

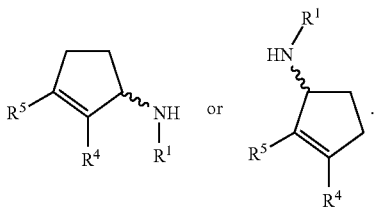

In certain embodiments, the compound of Formula (D) is of the formula:

and the compound of the Formula (I) is of the formula:

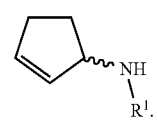

In certain embodiments, the compound of Formula (D) is of the formula:

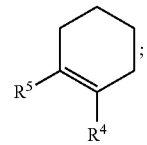

and the compound of the Formula (I) is of the formula:

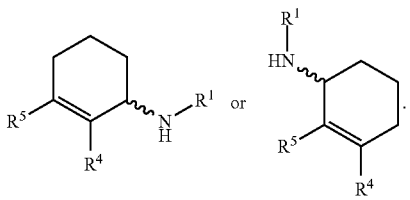

In certain embodiments, the compound of Formula (D) is of the formula:

and the compound of the Formula (I) is of the formula:

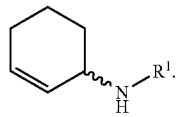

In certain embodiments, the compound of Formula (D) is of the formula:

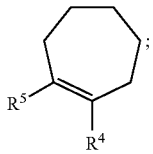

and the compound of the Formula (I) is of the formula:

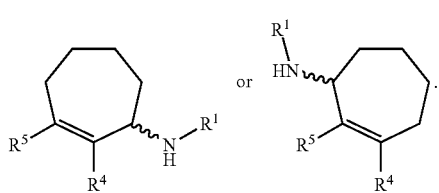

In certain embodiments, the compound of Formula (D) is of the formula:

and the compound of the Formula (I) is of the formula:

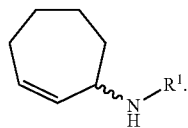

In certain embodiments, the compound of Formula (D) is of the formula:

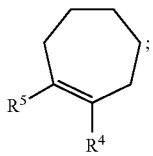

and the compound of the Formula (I) is of the formula:

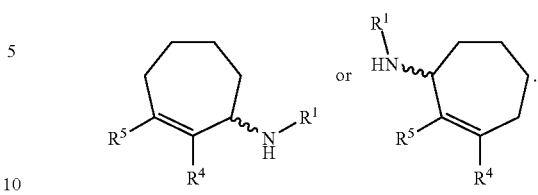

In certain embodiments, the compound of Formula (D) is of the formula:

and the compound of the Formula (I) is of the formula:

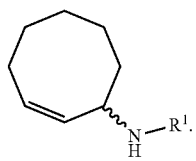

Compounds of Formula (B) include a ligand L attached to the $Fe^{II}$ atom. L may be any ligand capable of binding to the $Fe^{II}$ atom to form a coordination complex. In certain embodiments, L is a compound including one or more electron donating moieties. In certain embodiments, L a compound including one or more heteroatoms. In certain embodiments, L is a solvent. In certain embodiments, L is $N(R^b)_3$. In certain embodiments, L is $NEt_3$. In certain embodiments, L is $(i-Pr)_2NEt$. In certain embodiments, L is $R^b$—O—$R^b$. In certain embodiments, L is $R^b$—O—$R^b$; and each occurrence of $R^b$ is independently optionally substituted alkyl. In certain embodiments, L is $R^b$—O—$R^b$; and each occurrence of $R^b$ is independently $C_{1-6}$ alkyl. In certain embodiments, L is diethyl ether. In certain embodiments, L is methyl t-butyl ether. In certain embodiments, L is $R^b$—S—$R^b$. In certain embodiments, L is dimethyl sulfide. In certain embodiments, L is diethyl sulfide. In certain embodiments, L is substituted heterocyclyl. In certain embodiments, L is unsubstituted heterocyclyl. In certain embodiments, L is substituted tetrahydrofuran. In certain embodiments, L is 2-methyltetrahydrofuran. In certain embodiments, L is unsubstituted tetrahydrofuran. In certain embodiments, L is substituted tetrahydropyran. In certain embodiments, L is unsubstituted tetrahydropyran. In certain embodiments, L is substituted heteroaryl. In certain embodiments, L is unsubstituted heteroaryl. In certain embodiments, L is substituted pyridine. In certain embodiments, L is 2,6-lutidine. In certain embodiments, L is unsubstituted pyridine.

In certain embodiments, at least one $R^b$ is substituted alkyl. In certain embodiments, at least one $R^b$ is unsubstituted alkyl. In certain embodiments, at least one $R^b$ is $C_{1-6}$ alkyl. In certain embodiments, at least one $R^b$ is methyl. In certain embodiments, at least one $R^b$ is ethyl. In certain embodiments, at least one $R^b$ is propyl. In certain embodiments, at least one $R^b$ is butyl. In certain embodiments, at least one $R^b$ is Ad. In certain embodiments, at least one $R^b$ is substituted alkenyl. In certain embodiments, at least one $R^b$ is unsubstituted alkenyl. In certain embodiments, at least one $R^b$ is vinyl. In certain embodiments, at least one $R^b$ is substituted alkynyl. In certain embodiments, at least one $R^b$ is unsubstituted alkynyl. In certain embodiments, at least one $R^b$ is ethynyl. In certain embodiments, at least one $R^b$ is substituted carbocyclyl. In certain embodiments, at least one $R^b$ is unsubstituted carbocyclyl. In certain embodiments, at least one $R^b$ is cyclopropyl. In certain embodiments, at least one $R^b$ is cyclobutyl. In certain embodiments, at least one $R^b$ is cyclopentyl. In certain embodiments, at least one $R^b$ is cyclohexyl. In certain embodiments, at least one $R^b$ is cycloheptyl. In certain embodiments, at least one $R^b$ is substituted heterocyclyl. In certain embodiments, at least one $R^b$ is unsubstituted heterocyclyl. In certain embodiments, at least one $R^b$ is substituted aryl. In certain embodiments, at least one $R^b$ is unsubstituted aryl. In certain embodiments, at least one $R^b$ is substituted phenyl. In certain embodiments, at least one $R^b$ is unsubstituted phenyl. In certain embodiments, at least one $R^b$ is substituted heteroaryl. In certain embodiments, at least one $R^b$ is unsubstituted heteroaryl. In certain embodiments, at least one $R^b$ is substituted pyridyl. In certain embodiments, at least one $R^b$ is unsubstituted pyridyl.

Shown in FIG. 2 is a proposed mechanism for the intermolecular C—H amination reaction of an azide $RN_3$ (e.g., $AdN_3$) and a C—H source $R'CH_3$ (e.g., PhMe), catalyzed by a $Fe^{II}Cl(L)$-dipyrromethene complex (e.g., 3A), to yield an acyclic secondary amine RNHR' (e.g., $AdNHCH_2Ph$). First, the $Fe^{II}Cl(L)$-dipyrromethene complex undergoes a ligand exchange to form $Fe^{II}Cl(N_3R)$ (e.g., $Fe^{II}Cl(N_3Ad)$)-dipyrromethene complex. The $Fe^{II}Cl(N_3R)$-dipyrromethene complex reacts with the C—H source $R'CH_3$ (e.g., PhMe) to release a molecule of $N_2$ and form $Fe^{III}Cl(.NR)$ (e.g., $Fe^{III}Cl(.NAd)$)-dipyrromethene complex (a "$Fe^{III}$(imido) complex"). Hydrogen transfer from $R'CH_3$ to the $Fe^{III}$(imido) complex gives rise to $Fe^{III}Cl(NHR)$ (e.g., $Fe^{III}Cl(NHAd)$)-dipyrromethene complex and $R'CH_2$. radical. A radical recombination furnishes the C—H amination product RNHR' (e.g., $AdNHCH_2Ph$), regenerates the $Fe^{II}Cl$ (L)-dipyrromethene complex, and therefore, completes the catalytic cycle. The net effect of such a reaction is that a nitrene group RN: (e.g., AdN:) is transferred to a C—H source $R'CH_3$ (e.g., PhMe). The mechanism for a similar reaction using compound 3B as the catalyst instead of 3A is similar to or the same as the mechanism described herein.

The steps of the methods of the invention may be performed under any suitable conditions. A suitable condition is a combination of physical and chemical parameters under which an intended product (e.g., an acyclic or cyclic amine) or intermediate may be formed using the inventive methods. A suitable condition may include a suitable solvent, such as an organic solvent (e.g., benzene, toluene, xylene, acetone, acetonitrile (ACN), N,N-dimethylformamide (DMF), N,N-dimethylacetamide (DMA), dimethysulfoxide (DMSO), N-methyl-2-pyrrolidone (NMP), 2-pyrrolidone, tetrahydrofuran (THF), or a mixture thereof). In certain embodiments, the suitable solvent is benzene.

A suitable condition may also include a suitable temperature under which one or more steps of a method of the invention are performed. In certain embodiments, the suitable temperature is at least about 0° C., at least about 20° C., at least about 23° C., at least about 25° C., at least about 40° C., at least about 60° C., at least about 65° C., at least about 80° C., at least about 100° C., or at least about 120° C. In certain embodiments, the suitable temperature is lower than about 120° C., lower than about 100° C., lower than about 80° C., lower than about 65° C., lower than about 60° C., lower than about 40° C., lower than about 25° C., lower than about 23° C., lower than about 20° C., or lower than about 0° C. Combinations of the above-referenced ranges are also possible (e.g., a suitable temperature of at least about 0° C. and lower than about 65° C.). Other ranges are also possible. In certain embodiments, the suitable temperature is about 0° C. In certain embodiments, the suitable temperature is about 23° C. In certain embodiments, the suitable temperature is about 60° C. In certain embodiments, the suitable temperature is about 65° C. A suitable temperature may be a variable temperature during one or more steps of a method of the invention.

A suitable condition may also include a suitable pressure under which one or more steps of the inventive methods are performed. In certain embodiments, the suitable pressure is about 1 atmosphere. A suitable pressure may also be higher or lower than 1 atmosphere.

A suitable condition may also include a suitable atmosphere under which one or more steps of the inventive methods are performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that one or more steps of a method of the invention last. In certain embodiments, the suitable time duration is in the order of minutes, hours (e.g., about 6 or about 12 hours), or days (e.g., about 1 day).

A suitable condition may also include irradiation with microwave, shielding from ambient light, and/or agitating (e.g., stirring). One or more intermediates resulting from a step of a method of the invention may be isolated and/or purified, and the isolated and/or purified intermediates may be reacted in a next step of the method. The isolated and/or purified intermediates may be substantially pure or may contain one or more other components, such as reagents and solvents employed in the step yielding the intermediates and byproducts. The one or more intermediates may also be reacted in a next step without being isolated and/or purified.

Synthesis of Coordination Complexes of Cyclic Secondary Amines and a Ferrous Compound The present invention also provides methods of preparing compounds of Formula (II-1), which are coordination complexes of cyclic secondary amines and a ferrous compound:

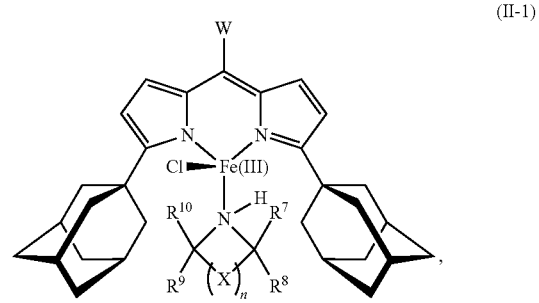

(II-1)

and salts and stereoisomers thereof, the method comprising the steps of:

reacting an azide of Formula (F), or a salt or stereoisomer thereof, with a ferrous compound of Formula (G), or a salt or stereoisomer thereof:

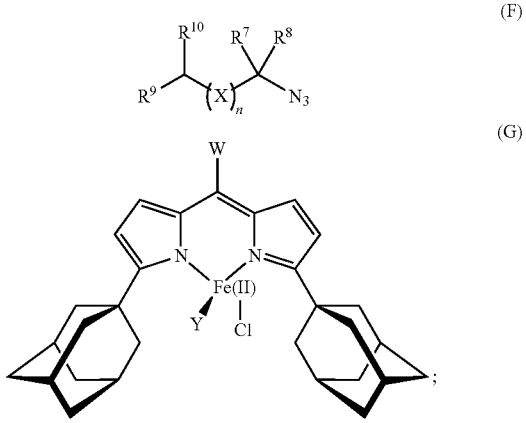

(F)

(G)

wherein:

W is selected from the group consisting of mesityl and 2,6-dichlorophenyl;

each occurrence of X is independently selected from the group consisting of —O—, —S—, —NR$^c$—, and —C(R$^d$)$_2$—;

R$^c$ is selected from the group consisting of hydrogen, a nitrogen protecting group, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;

each one of R$^7$, R$^8$, R$^9$, and R$^{10}$, and each occurrence of R$^d$, are independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^e$, —N(R$^e$)$_2$, —SR$^e$, —CN, —C(=NR$^e$)R$^e$, —C(=NR$^e$)OR$^e$, —C(=NR$^e$)N(R$^e$)$_2$, —NO$_2$, —NR$^e$C(=O)R$^e$, —NR$^e$C(=O)OR$^e$, —NR$^e$C(=O)N(R$^e$)$_2$, —C(=O)R$^e$, —OC(=O)OR$^e$, —OC(=O)N(R$^e$)$_2$, and —ON(R$^e$)$_2$;

each occurrence of R$^e$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or optionally two R$^e$ groups are joined to form an optionally substituted heterocyclic ring;

optionally two of R$^7$, R$^8$, R$^9$, R$^{10}$, R$^c$, and R$^d$ groups are joined to form an optionally substituted carbocyclyl or optionally substituted heterocyclic ring;

Y is selected from the group consisting of N(R$^f$)$_3$, R$^f$—O—R$^f$, R$^f$—S—R$^f$, optionally substituted heterocyclyl, and optionally substituted heteroaryl;

each occurrence of R$^f$ is independently selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl; and n is 1, 2, 3, 4, or 5.

In compounds described herein, W is selected from the group consisting of mesityl and 2,6-dichlorophenyl. In certain embodiments, W is mesityl. In certain embodiments, W is 2,6-dichlorophenyl.

In compounds of Formulae (II-1) and (F), each occurrence of X is independently selected from the group consisting of —O—, —S—, —NR$^c$—, and —C(R$^d$)$_2$—. In certain embodiments, at least one X is —O—. In certain embodiments, at least one X is —S—. In certain embodiments, at least one X is —NR$^c$—. In certain embodiments, at least one X is —N(C$_{1-6}$ alkyl)-. In certain embodiments, at least one X is —N(Me)-. In certain embodiments, at least one X is —NH—. In certain embodiments, at least one X is —C(R$^d$)$_2$—. In certain embodiments, at least one X is —C(C$_{1-6}$ alkyl)$_2$-. In certain embodiments, at least one X is —C(Me)$_2$-. In certain embodiments, at least one X is —C(Et)$_2$-. In certain embodiments, at least one X is —C(Pr)$_2$—. In certain embodiments, at least one X is —C(Bu)$_2$-. In certain embodiments, at least one X is —C(C$_{1-6}$ alkenyl)$_2$-. In certain embodiments, at least one X is —C(vinyl)$_2$-. In certain embodiments, at least one X is —C(allyl)$_2$-. In certain embodiments, at least one X is —CH(4-butenyl)-. In certain embodiments, at least one X is —C(C$_{1-6}$ alkynyl)$_2$-. In certain embodiments, at least one X is —C(ethynyl)$_2$-. In certain embodiments, at least one X is —CH(R$^d$)—. In certain embodiments, at least one X is —CH(C$_{1-6}$ alkyl)-. In certain embodiments, at least one X is —CH(Me)-. In certain embodiments, at least one X is —CH(Et)-. In certain embodiments, at least one X is —C(Pr)$_2$—. In certain embodiments, at least one X is —C(Bu)$_2$-. In certain embodiments, at least one X is —CH(C$_{1-6}$ alkenyl)-. In certain embodiments, at least one X is —CH(vinyl)-. In certain embodiments, at least one X is —CH(allyl)-. In certain embodiments, at least one X is —CH(4-butenyl)-. In certain embodiments, at least one X is —CH(C$_{1-6}$ alkynyl)-. In certain embodiments, at least one X is —CH(ethynyl)-. In certain embodiments, at least one X is —CH(aryl)-. In certain embodiments, at least one X is —CH(Ph)-. In certain embodiments, at least one X is —CH(heteroaryl)-. In certain embodiments, at least one X is —CH(pyridyl)-. In certain embodiments, at least one X is —CH(OR$^e$)—. In certain embodiments, at least one X is —CH(O-aryl)-. In certain embodiments, at least one X is —CH(OPh)-. In certain embodiments, at least one X is —CH(O—C$_{1-6}$ alkyl)-. In certain embodiments, at least one X is —CH(OH)—. In certain embodiments, at least one X is —CH(N(R$^e$)$_2$)—. In certain embodiments, at least one X is —CH(N(C$_{1-6}$ alkyl)$_2$)-. In certain embodiments, at least one X is —CH(NH$_2$)—. In certain embodiments, at least one X is —CH(C(=O)OR$^e$)—. In certain embodiments, at least one X is —CH(C(=O)OMe)-. In certain embodiments, at least one X is —CH(C(=O)OEt)-. In certain embodiments, at least one X is —CH$_2$—.

In compounds of Formulae (II-1) and (F), when X is —NR$^c$—, R$^c$ is a substituent on the nitrogen atom. In certain embodiments, at least one R$^c$ is H. In certain embodiments, at least one R$^c$ is substituted alkyl. In certain embodiments, at least one R$^c$ is unsubstituted alkyl. In certain embodiments, at least one R$^c$ is C$_{1-6}$ alkyl. In certain embodiments, at least one R$^c$ is methyl. In certain embodiments, at least one R$^c$ is ethyl. In certain embodiments, at least one R$^c$ is propyl. In certain embodiments, at least one R$^c$ is butyl. In certain embodiments, at least one R$^c$ is t-butyl. In certain embodiments, at least one R$^c$ is Ad. In certain embodiments, at least one R$^c$ is substituted alkenyl. In certain embodiments, at least one R$^c$ is unsubstituted alkenyl. In certain embodiments, at least one R$^c$ is vinyl. In certain embodiments, at least one $R^c$ is substituted alkynyl. In certain embodiments, at least one $R^c$ is unsubstituted alkynyl. In certain embodiments, at least one $R^c$ is ethynyl. In certain embodiments, at least one $R^c$ is substituted carbocyclyl. In certain embodiments, at least one $R^c$ is unsubstituted carbocyclyl. In certain embodiments, at least one $R^c$ is cyclopropyl. In certain embodiments, at least one $R^c$ is cyclobutyl. In certain embodiments, at least one $R^c$ is cyclopentyl. In certain embodiments, at least one $R^c$ is cyclohexyl. In certain embodiments, at least one $R^c$ is cycloheptyl. In certain embodiments, at least one $R^c$ is substituted heterocyclyl. In certain embodiments, at least one $R^c$ is unsubstituted heterocyclyl. In certain embodiments, at least one $R^c$ is substituted aryl. In certain embodiments, at least one $R^c$ is unsubstituted aryl. In certain embodiments, at least one $R^c$ is substituted phenyl. In certain embodiments, at least one $R^c$ is tolyl. In certain embodiments, at least one $R^c$ is 4-tolyl. In certain embodiments, at least one $R^c$ is Mes. In certain embodiments, at least one $R^c$ is unsubstituted phenyl. In certain embodiments, at least one $R^c$ is substituted naphthyl. In certain embodiments, at least one $R^c$ is unsubstituted naphthyl. In certain embodiments, at least one $R^c$ is substituted heteroaryl. In certain embodiments, at least one $R^c$ is unsubstituted heteroaryl. In certain embodiments, at least one $R^c$ is monocyclic heteroaryl. In certain embodiments, at least one $R^c$ is 5-membered monocyclic heteroaryl. In certain embodiments, at least one $R^c$ is 5-membered monocyclic heteroaryl, wherein only one of the five atoms in the ring of the heteroaryl is selected from the group consisting of nitrogen, oxygen, and sulfur. In certain embodiments, at least one $R^c$ is 5-membered monocyclic heteroaryl, wherein only two of the five atoms in the ring of the heteroaryl are independently selected from the group consisting of nitrogen, oxygen, and sulfur. In certain embodiments, at least one $R^c$ is 5-membered monocyclic heteroaryl, wherein only three of the five atoms in the ring of the heteroaryl are independently selected from the group consisting of nitrogen, oxygen, and sulfur. In certain embodiments, at least one $R^c$ is tetrazolyl. In certain embodiments, at least one $R^c$ is 6-membered monocyclic heteroaryl. In certain embodiments, at least one $R^c$ is 6-membered monocyclic heteroaryl, wherein only one of the six atoms in the ring of the heteroaryl is selected from the group consisting of nitrogen, oxygen, and sulfur. In certain embodiments, at least one $R^c$ is 6-membered monocyclic heteroaryl, wherein only two of the six atoms in the ring of the heteroaryl are independently selected from the group consisting of nitrogen, oxygen, and sulfur. In certain embodiments, at least one $R^c$ is triazinyl. In certain embodiments, at least one $R^c$ is tetrazinyl. In certain embodiments, at least one $R^c$ is bicyclic heteroaryl, wherein the point of attachment may be at any atom of the heteroaryl, as valency permits. In certain embodiments, at least one $R^c$ is a monocyclic heteroaryl fused with phenyl. In certain embodiments, at least one $R^c$ is a 5-membered monocyclic heteroaryl fused with phenyl. In certain embodiments, at least one $R^c$ is a 6-membered monocyclic heteroaryl fused with phenyl. In certain embodiments, at least one $R^c$ is a monocyclic heteroaryl fused with another monocyclic heteroaryl. In certain embodiments, at least one $R^c$ is a 5-membered monocyclic heteroaryl fused with another 5-membered monocyclic heteroaryl. In certain embodiments, at least one $R^c$ is a 5-membered monocyclic heteroaryl fused with a 6-membered monocyclic heteroaryl. In certain embodiments, at least one $R^c$ is a 6-membered monocyclic heteroaryl fused with another 6-membered monocyclic heteroaryl. In certain embodiments, at least one $R^c$ is a nitrogen protecting group. In certain embodiments, at least one $R^c$ is Bn, Boc, Cbz, Fmoc, trifluoroacetyl, triphenylmethyl, or Ts.

In compounds of Formulae (II-1) and (F), when X is $-C(R^d)_2-$, at least one $R^d$ is a substituent on the carbon atom. In certain embodiments, at least one $R^d$ is H. In certain embodiments, at least one $R^d$ is halogen. In certain embodiments, at least one $R^d$ is F. In certain embodiments, at least one $R^d$ is Cl. In certain embodiments, at least one $R^d$ is Br. In certain embodiments, at least one $R^d$ is I (iodine). In certain embodiments, at least one $R^d$ is substituted acyl. In certain embodiments, at least one $R^d$ is unsubstituted acyl. In certain embodiments, at least one $R^d$ is $-C(=O)R^e$. In certain embodiments, at least one $R^d$ is acetyl. In certain embodiments, at least one $R^d$ is $-C(=O)OR^e$. In certain embodiments, at least one $R^d$ is $-C(=O)N(R^e)_2$. In certain embodiments, at least one $R^d$ is substituted alkyl. In certain embodiments, at least one $R^d$ is unsubstituted alkyl. In certain embodiments, at least one $R^d$ is $C_{1-6}$ alkyl. In certain embodiments, at least one $R^d$ is methyl. In certain embodiments, at least one $R^d$ is ethyl. In certain embodiments, at least one $R^d$ is propyl. In certain embodiments, at least one $R^d$ is butyl. In certain embodiments, at least one $R^d$ is Ad. In certain embodiments, at least one $R^d$ is substituted alkenyl. In certain embodiments, at least one $R^d$ is unsubstituted alkenyl. In certain embodiments, at least one $R^d$ is vinyl. In certain embodiments, at least one $R^d$ is substituted alkynyl. In certain embodiments, at least one $R^d$ is unsubstituted alkynyl. In certain embodiments, at least one $R^d$ is ethynyl. In certain embodiments, at least one $R^d$ is substituted carbocyclyl. In certain embodiments, at least one $R^d$ is unsubstituted carbocyclyl. In certain embodiments, at least one $R^d$ is cyclopropyl. In certain embodiments, at least one $R^d$ is cyclobutyl. In certain embodiments, at least one $R^d$ is cyclopentyl. In certain embodiments, at least one $R^d$ is cyclohexyl. In certain embodiments, at least one $R^d$ is cycloheptyl. In certain embodiments, at least one $R^d$ is substituted heterocyclyl. In certain embodiments, at least one $R^d$ is unsubstituted heterocyclyl. In certain embodiments, at least one $R^d$ is substituted aryl. In certain embodiments, at least one $R^d$ is unsubstituted aryl. In certain embodiments, at least one $R^d$ is substituted phenyl. In certain embodiments, at least one $R^d$ is unsubstituted phenyl. In certain embodiments, at least one $R^d$ is substituted naphthyl. In certain embodiments, at least one $R^d$ is unsubstituted naphthyl. In certain embodiments, at least one $R^d$ is substituted heteroaryl. In certain embodiments, at least one $R^d$ is unsubstituted heteroaryl. In certain embodiments, at least one $R^d$ is monocyclic heteroaryl. In certain embodiments, at least one $R^d$ is 5-membered monocyclic heteroaryl. In certain embodiments, at least one $R^d$ is 5-membered monocyclic heteroaryl, wherein only one of the five atoms in the ring of the heteroaryl is selected from the group consisting of nitrogen, oxygen, and sulfur. In certain embodiments, at least one $R^d$ is 5-membered monocyclic heteroaryl, wherein only two of the five atoms in the ring of the heteroaryl are independently selected from the group consisting of nitrogen, oxygen, and sulfur. In certain embodiments, at least one $R^d$ is 5-membered monocyclic heteroaryl, wherein only three of the five atoms in the ring of the heteroaryl are independently selected from the group consisting of nitrogen, oxygen, and sulfur. In certain embodiments, at least one $R^d$ is tetrazolyl. In certain embodiments, at least one $R^d$ is 6-membered monocyclic heteroaryl. In certain embodiments, at least one $R^d$ is 6-membered monocyclic heteroaryl, wherein only one of the six atoms in the ring of the heteroaryl is selected from the group consisting of nitrogen, oxygen, and sulfur. In certain embodiments, at least one $R^d$ is 6-membered monocyclic heteroaryl, wherein only two of the six atoms in the ring of the heteroaryl are independently selected from the group consisting of nitrogen, oxygen, and sulfur. In certain embodiments, at least one $R^d$ is triazinyl. In certain embodiments, at least one $R^d$ is tetrazinyl. In certain embodiments, at least one $R^d$ is bicyclic heteroaryl, wherein the point of attachment may be at any atom of the heteroaryl, as valency permits. In certain embodiments, at least one $R^d$ is a monocyclic heteroaryl fused with phenyl. In certain embodiments, at least one $R^d$ is a 5-membered monocyclic heteroaryl fused with phenyl. In certain embodiments, at least one $R^d$ is a 6-membered monocyclic heteroaryl fused with phenyl. In certain embodiments, at least one $R^d$ is a monocyclic heteroaryl fused with another monocyclic heteroaryl. In certain embodiments, at least one $R^d$ is a 5-membered monocyclic heteroaryl fused with another 5-membered monocyclic heteroaryl. In certain embodiments, at least one $R^d$ is a 5-membered monocyclic heteroaryl fused with a 6-membered monocyclic heteroaryl. In certain embodiments, at least one $R^d$ is a 6-membered monocyclic heteroaryl fused with another 6-membered monocyclic heteroaryl. In certain embodiments, at least one $R^d$ is —$OR^e$. In certain embodiments, at least one $R^d$ is —OH when attached to an $sp^3$ carbon atom. In certain embodiments, at least one $R^d$ is —$SR^e$. In certain embodiments, at least one $R^d$ is —SH when attached to an $sp^3$ carbon atom. In certain embodiments, at least one $R^d$ is —$N(R^e)_2$. In certain embodiments, at least one $R^d$ is —$NH_2$ when attached to an $sp^3$ carbon atom. In certain embodiments, at least one $R^d$ is —CN. In certain embodiments, at least one $R^d$ is —SCN. In certain embodiments, at least one $R^d$ is —$C(=NR^e)R^e$, —$C(=NR^e)OR^e$, or —$C(=NR^e)N(R^e)_2$. In certain embodiments, at least one $R^d$ is —$C(=O)R^e$, —$C(=O)OR^e$, or —$C(=O)N(R^e)_2$. In certain embodiments, at least one $R^d$ is —$NO_2$. In certain embodiments, at least one $R^d$ is —$NR^eC(=O)R^e$, —$NR^eC(=O)OR^e$, or —$NR^eC(=O)N(R^e)_2$. In certain embodiments, at least one $R^d$ is —$OC(=O)R^e$, —$OC(=O)OR^e$, or —$OC(=O)N(R^e)_2$. In certain embodiments, at least one $R^d$ is —$ON(R^e)_2$.

In certain embodiments, n is 1. In certain embodiments, n is 2. In certain embodiments, n is 3. In certain embodiments, n is 4. In certain embodiments, n is 5.

Compounds of Formulae (II-1) and (F) include a substituent $R^7$. In certain embodiments, $R^7$ is H. In certain embodiments, $R^7$ is halogen. In certain embodiments, $R^7$ is F. In certain embodiments, $R^7$ is Cl. In certain embodiments, $R^7$ is Br. In certain embodiments, $R^7$ is I (iodine). In certain embodiments, $R^7$ is substituted acyl. In certain embodiments, $R^7$ is unsubstituted acyl. In certain embodiments, $R^7$ is —$C(=O)R^e$. In certain embodiments, $R^7$ is acetyl. In certain embodiments, $R^7$ is —$C(=O)OR^e$. In certain embodiments, $R^7$ is —$C(=O)N(R^e)_2$. In certain embodiments, $R^7$ is substituted alkyl. In certain embodiments, $R^7$ is unsubstituted alkyl. In certain embodiments, $R^7$ is $C_{1-6}$ alkyl. In certain embodiments, $R^7$ is methyl. In certain embodiments, $R^7$ is ethyl. In certain embodiments, $R^7$ is propyl. In certain embodiments, $R^7$ is butyl. In certain embodiments, $R^7$ is Ad. In certain embodiments, $R^7$ is substituted alkenyl. In certain embodiments, $R^7$ is unsubstituted alkenyl. In certain embodiments, $R^7$ is vinyl. In certain embodiments, $R^7$ is substituted alkynyl. In certain embodiments, $R^7$ is unsubstituted alkynyl. In certain embodiments, $R^7$ is ethynyl. In certain embodiments, $R^7$ is substituted carbocyclyl. In certain embodiments, $R^7$ is unsubstituted carbocyclyl. In certain embodiments, $R^7$ is cyclopropyl. In certain embodiments, $R^7$ is cyclobutyl. In certain embodiments, $R^7$ is cyclopentyl. In certain embodiments, $R^7$ is cyclohexyl. In certain embodiments, $R^7$ is cycloheptyl. In certain embodiments, $R^7$ is substituted heterocyclyl. In certain embodiments, $R^7$ is unsubstituted heterocyclyl. In certain embodiments, $R^7$ is substituted aryl. In certain embodiments, $R^7$ is unsubstituted aryl. In certain embodiments, $R^7$ is substituted phenyl. In certain embodiments, $R^7$ is unsubstituted phenyl. In certain embodiments, $R^7$ is substituted naphthyl. In certain embodiments, $R^7$ is unsubstituted naphthyl. In certain embodiments, $R^7$ is substituted heteroaryl. In certain embodiments, $R^7$ is unsubstituted heteroaryl. In certain embodiments, $R^7$ is monocyclic heteroaryl. In certain embodiments, $R^7$ is 5-membered monocyclic heteroaryl. In certain embodiments, $R^7$ is 5-membered monocyclic heteroaryl, wherein only one of the five atoms in the ring of the heteroaryl is selected from the group consisting of nitrogen, oxygen, and sulfur. In certain embodiments, $R^7$ is 5-membered monocyclic heteroaryl, wherein only two of the five atoms in the ring of the heteroaryl are independently selected from the group consisting of nitrogen, oxygen, and sulfur. In certain embodiments, $R^7$ is 5-membered monocyclic heteroaryl, wherein only three of the five atoms in the ring of the heteroaryl are independently selected from the group consisting of nitrogen, oxygen, and sulfur. In certain embodiments, $R^7$ is tetrazolyl. In certain embodiments, $R^7$ is 6-membered monocyclic heteroaryl. In certain embodiments, $R^7$ is 6-membered monocyclic heteroaryl, wherein only one of the six atoms in the ring of the heteroaryl is selected from the group consisting of nitrogen, oxygen, and sulfur. In certain embodiments, $R^7$ is 6-membered monocyclic heteroaryl, wherein only two of the six atoms in the ring of the heteroaryl are independently selected from the group consisting of nitrogen, oxygen, and sulfur. In certain embodiments, $R^7$ is triazinyl. In certain embodiments, $R^7$ is tetrazinyl. In certain embodiments, $R^7$ is bicyclic heteroaryl, wherein the point of attachment may be at any atom of the heteroaryl, as valency permits. In certain embodiments, $R^7$ is a monocyclic heteroaryl fused with phenyl. In certain embodiments, $R^7$ is a 5-membered monocyclic heteroaryl fused with phenyl. In certain embodiments, $R^7$ is a 6-membered monocyclic heteroaryl fused with phenyl. In certain embodiments, $R^7$ is a monocyclic heteroaryl fused with another monocyclic heteroaryl. In certain embodiments, $R^7$ is a 5-membered monocyclic heteroaryl fused with another 5-membered monocyclic heteroaryl. In certain embodiments, $R^7$ is a 5-membered monocyclic heteroaryl fused with a 6-membered monocyclic heteroaryl. In certain embodiments, $R^7$ is a 6-membered monocyclic heteroaryl fused with another 6-membered monocyclic heteroaryl. In certain embodiments, $R^7$ is —$OR^e$. In certain embodiments, $R^7$ is —OH when attached to an $sp^3$ carbon atom. In certain embodiments, $R^7$ is —$SR^e$. In certain embodiments, $R^7$ is —SH when attached to an $sp^3$ carbon atom. In certain embodiments, $R^7$ is —$N(R^e)_2$. In certain embodiments, $R^7$ is —$NH_2$ when attached to an $sp^3$ carbon atom. In certain embodiments, $R^7$ is —CN. In certain embodiments, $R^7$ is —SCN. In certain embodiments, $R^7$ is —$C(=NR^e)R^e$, —$C(=NR^e)OR^e$, or —$C(=NR^e)N(R^e)_2$. In certain embodiments, $R^7$ is —$C(=O)R^e$, —$C(=O)OR^e$, or —$C(=O)N(R^e)_2$. In certain embodiments, $R^7$ is —$NO_2$. In certain embodiments, $R^7$ is —$NR^eC(=O)R^e$, —$NR^eC(=O)OR^e$, or —$NR^eC(=O)N(R^e)_2$. In certain embodiments, $R^7$ is —$OC(=O)R^e$, —$OC(=O)OR^e$, or —$OC(=O)N(R^e)_2$. In certain embodiments, $R^7$ is —$ON(R^e)_2$.

Compounds of Formulae (II-1) and (F) also include a substituent $R^8$. In certain embodiments, $R^8$ is H. In certain embodiments, $R^8$ is halogen. In certain embodiments, $R^8$ is F. In certain embodiments, $R^8$ is Cl. In certain embodiments, $R^8$ is Br. In certain embodiments, $R^8$ is I (iodine). In certain embodiments, $R^8$ is substituted acyl. In certain embodiments, $R^8$ is unsubstituted acyl. In certain embodiments, $R^8$ is —C(=O)$R^e$. In certain embodiments, $R^8$ is acetyl. In certain embodiments, $R^8$ is —C(=O)O$R^e$. In certain embodiments, $R^8$ is —C(=O)N($R^e$)$_2$. In certain embodiments, $R^8$ is substituted alkyl. In certain embodiments, $R^8$ is unsubstituted alkyl. In certain embodiments, $R^8$ is $C_{1-6}$ alkyl. In certain embodiments, $R^8$ is methyl. In certain embodiments, $R^8$ is ethyl. In certain embodiments, $R^8$ is propyl. In certain embodiments, $R^8$ is butyl. In certain embodiments, $R^8$ is Ad. In certain embodiments, $R^8$ is substituted alkenyl. In certain embodiments, $R^8$ is unsubstituted alkenyl. In certain embodiments, $R^8$ is vinyl. In certain embodiments, $R^8$ is substituted alkynyl. In certain embodiments, $R^8$ is unsubstituted alkynyl. In certain embodiments, $R^8$ is ethynyl. In certain embodiments, $R^8$ is substituted carbocyclyl. In certain embodiments, $R^8$ is unsubstituted carbocyclyl. In certain embodiments, $R^8$ is cyclopropyl. In certain embodiments, $R^8$ is cyclobutyl. In certain embodiments, $R^8$ is cyclopentyl. In certain embodiments, $R^8$ is cyclohexyl. In certain embodiments, $R^8$ is cycloheptyl. In certain embodiments, $R^8$ is substituted heterocyclyl. In certain embodiments, $R^8$ is unsubstituted heterocyclyl. In certain embodiments, $R^8$ is substituted aryl. In certain embodiments, $R^8$ is unsubstituted aryl. In certain embodiments, $R^8$ is substituted phenyl. In certain embodiments, $R^8$ is unsubstituted phenyl. In certain embodiments, $R^8$ is substituted naphthyl. In certain embodiments, $R^8$ is unsubstituted naphthyl. In certain embodiments, $R^8$ is substituted heteroaryl. In certain embodiments, $R^8$ is unsubstituted heteroaryl. In certain embodiments, $R^8$ is monocyclic heteroaryl. In certain embodiments, $R^8$ is 5-membered monocyclic heteroaryl. In certain embodiments, $R^8$ is 5-membered monocyclic heteroaryl, wherein only one of the five atoms in the ring of the heteroaryl is selected from the group consisting of nitrogen, oxygen, and sulfur. In certain embodiments, $R^8$ is 5-membered monocyclic heteroaryl, wherein only two of the five atoms in the ring of the heteroaryl are independently selected from the group consisting of nitrogen, oxygen, and sulfur. In certain embodiments, $R^8$ is 5-membered monocyclic heteroaryl, wherein only three of the five atoms in the ring of the heteroaryl are independently selected from the group consisting of nitrogen, oxygen, and sulfur. In certain embodiments, $R^8$ is tetrazolyl. In certain embodiments, $R^8$ is 6-membered monocyclic heteroaryl. In certain embodiments, $R^8$ is 6-membered monocyclic heteroaryl, wherein only one of the six atoms in the ring of the heteroaryl is selected from the group consisting of nitrogen, oxygen, and sulfur. In certain embodiments, $R^8$ is 6-membered monocyclic heteroaryl, wherein only two of the six atoms in the ring of the heteroaryl are independently selected from the group consisting of nitrogen, oxygen, and sulfur. In certain embodiments, $R^8$ is triazinyl. In certain embodiments, $R^8$ is tetrazinyl. In certain embodiments, $R^8$ is bicyclic heteroaryl, wherein the point of attachment may be at any atom of the heteroaryl, as valency permits. In certain embodiments, $R^8$ is a monocyclic heteroaryl fused with phenyl. In certain embodiments, $R^8$ is a 5-membered monocyclic heteroaryl fused with phenyl. In certain embodiments, $R^8$ is a 6-membered monocyclic heteroaryl fused with phenyl. In certain embodiments, $R^8$ is a monocyclic heteroaryl fused with another monocyclic heteroaryl. In certain embodiments, $R^8$ is a 5-membered monocyclic heteroaryl fused with another 5-membered monocyclic heteroaryl. In certain embodiments, $R^8$ is a 5-membered monocyclic heteroaryl fused with a 6-membered monocyclic heteroaryl. In certain embodiments, $R^8$ is a 6-membered monocyclic heteroaryl fused with another 6-membered monocyclic heteroaryl. In certain embodiments, $R^8$ is —O$R^e$. In certain embodiments, $R^8$ is —OH when attached to an $sp^3$ carbon atom. In certain embodiments, $R^8$ is —S$R^e$. In certain embodiments, $R^8$ is —SH when attached to an $sp^3$ carbon atom. In certain embodiments, $R^8$ is —N($R^e$)$_2$. In certain embodiments, $R^8$ is —NH$_2$ when attached to an $sp^3$ carbon atom. In certain embodiments, $R^8$ is —CN. In certain embodiments, $R^8$ is —SCN. In certain embodiments, $R^8$ is —C(=N$R^e$)$R^e$, —C(=N$R^e$)O$R^e$, or —C(=N$R^e$)N($R^e$)$_2$. In certain embodiments, $R^8$ is —C(=O)$R^e$, —C(=O)O$R^e$, or —C(=O)N($R^e$)$_2$. In certain embodiments, $R^8$ is —NO$_2$. In certain embodiments, $R^8$ is —N$R^e$C(=O)$R^e$, —N$R^e$C(=O)O$R^e$, or —N$R^e$C(=O)N($R^e$)$_2$. In certain embodiments, $R^8$ is —OC(=O)$R^e$, —OC(=O)O$R^e$, or —OC(=O)N($R^e$)$_2$. In certain embodiments, $R^8$ is —ON($R^e$)$_2$.

Compounds of Formulae (II-1) and (F) further include a substituent $R^9$. In certain embodiments, $R^9$ is H. In certain embodiments, $R^9$ is halogen. In certain embodiments, $R^9$ is F. In certain embodiments, $R^9$ is Cl. In certain embodiments, $R^9$ is Br. In certain embodiments, $R^9$ is I (iodine). In certain embodiments, $R^9$ is substituted acyl. In certain embodiments, $R^9$ is —C(=O)$R^e$. In certain embodiments, $R^9$ is acetyl. In certain embodiments, $R^9$ is —C(=O)O$R^e$. In certain embodiments, $R^9$ is —C(=O)N($R^e$)$_2$. In certain embodiments, $R^9$ is substituted alkyl. In certain embodiments, $R^9$ is unsubstituted alkyl. In certain embodiments, $R^9$ is $C_{1-6}$ alkyl. In certain embodiments, $R^9$ is methyl. In certain embodiments, $R^9$ is ethyl. In certain embodiments, $R^9$ is propyl. In certain embodiments, $R^9$ is butyl. In certain embodiments, $R^9$ is Ad. In certain embodiments, $R^9$ is substituted alkenyl. In certain embodiments, $R^9$ is unsubstituted alkenyl. In certain embodiments, $R^9$ is vinyl. In certain embodiments, $R^9$ is substituted alkynyl. In certain embodiments, $R^9$ is unsubstituted alkynyl. In certain embodiments, $R^9$ is ethynyl. In certain embodiments, $R^9$ is substituted carbocyclyl. In certain embodiments, $R^9$ is unsubstituted carbocyclyl. In certain embodiments, $R^9$ is cyclopropyl. In certain embodiments, $R^9$ is cyclobutyl. In certain embodiments, $R^9$ is cyclopentyl. In certain embodiments, $R^9$ is cyclohexyl. In certain embodiments, $R^9$ is cycloheptyl. In certain embodiments, $R^9$ is substituted heterocyclyl. In certain embodiments, $R^9$ is unsubstituted heterocyclyl. In certain embodiments, $R^9$ is substituted aryl. In certain embodiments, $R^9$ is unsubstituted aryl. In certain embodiments, $R^9$ is substituted phenyl. In certain embodiments, $R^9$ is unsubstituted phenyl. In certain embodiments, $R^9$ is substituted naphthyl. In certain embodiments, $R^9$ is unsubstituted naphthyl. In certain embodiments, $R^9$ is substituted heteroaryl. In certain embodiments, $R^9$ is unsubstituted heteroaryl. In certain embodiments, $R^9$ is monocyclic heteroaryl. In certain embodiments, $R^9$ is 5-membered monocyclic heteroaryl. In certain embodiments, $R^9$ is 5-membered monocyclic heteroaryl, wherein only one of the five atoms in the ring of the heteroaryl is selected from the group consisting of nitrogen, oxygen, and sulfur. In certain embodiments, $R^9$ is 5-membered monocyclic heteroaryl, wherein only two of the five atoms in the ring of the heteroaryl are independently selected from the group consisting of nitrogen, oxygen, and sulfur. In certain embodiments, $R^9$ is 5-membered monocyclic heteroaryl, wherein only three of the five atoms in the ring of the heteroaryl are independently selected from the group consisting of nitrogen, oxygen, and sulfur. In certain embodiments, $R^9$ is tetrazolyl. In certain embodiments, $R^9$ is 6-membered monocyclic heteroaryl. In certain embodiments, $R^9$ is 6-membered monocyclic heteroaryl, wherein only one of the six atoms in the ring of the heteroaryl is selected from the group consisting of nitrogen, oxygen, and sulfur. In certain embodiments, $R^9$ is 6-membered monocyclic heteroaryl, wherein only two of the six atoms in the ring of the heteroaryl are independently selected from the group consisting of nitrogen, oxygen, and sulfur. In certain embodiments, $R^9$ is triazinyl. In certain embodiments, $R^9$ is tetrazinyl. In certain embodiments, $R^9$ is bicyclic heteroaryl, wherein the point of attachment may be at any atom of the heteroaryl, as valency permits. In certain embodiments, $R^9$ is a monocyclic heteroaryl fused with phenyl. In certain embodiments, $R^9$ is a 5-membered monocyclic heteroaryl fused with phenyl. In certain embodiments, $R^9$ is a 6-membered monocyclic heteroaryl fused with phenyl. In certain embodiments, $R^9$ is a monocyclic heteroaryl fused with another monocyclic heteroaryl. In certain embodiments, $R^9$ is a 5-membered monocyclic heteroaryl fused with another 5-membered monocyclic heteroaryl. In certain embodiments, $R^9$ is a 5-membered monocyclic heteroaryl fused with a 6-membered monocyclic heteroaryl. In certain embodiments, $R^9$ is a 6-membered monocyclic heteroaryl fused with another 6-membered monocyclic heteroaryl. In certain embodiments, $R^9$ is —$OR^e$. In certain embodiments, $R^9$ is —OH when attached to an $sp^3$ carbon atom. In certain embodiments, $R^9$ is —$SR^e$. In certain embodiments, $R^9$ is —SH when attached to an $sp^3$ carbon atom. In certain embodiments, $R^9$ is —$N(R^e)_2$. In certain embodiments, $R^9$ is —$NH_2$ when attached to an $sp^3$ carbon atom. In certain embodiments, $R^9$ is —CN. In certain embodiments, $R^9$ is —SCN. In certain embodiments, $R^9$ is —C(=$NR^e$)$R^e$, —C(=$NR^e$)$OR^e$, or —C(=$NR^e$)$N(R^e)_2$. In certain embodiments, $R^9$ is —C(=O)$R^e$, —C(=O)$OR^e$, or —C(=O)N$(R^e)_2$. In certain embodiments, $R^9$ is —$NO_2$. In certain embodiments, $R^9$ is —$NR^e$C(=O)$R^e$, —$NR^e$C(=O)$OR^e$, or —$NR^e$C(=O)N$(R^e)_2$. In certain embodiments, $R^9$ is —OC(=O)$R^e$, —OC(=O)$OR^e$, or —OC(=O)N$(R^e)_2$. In certain embodiments, $R^9$ is —ON$(R^e)_2$.

Compounds of Formulae (II-1) and (F) still include a substituent $R^{10}$. In certain embodiments, $R^{10}$ is H. In certain embodiments, $R^{10}$ is halogen. In certain embodiments, $R^{10}$ is F. In certain embodiments, $R^{10}$ is Cl. In certain embodiments, $R^{10}$ is Br. In certain embodiments, $R^{10}$ is I (iodine). In certain embodiments, $R^{10}$ is substituted acyl. In certain embodiments, $R^{10}$ is unsubstituted acyl. In certain embodiments, $R^{10}$ is —C(=O)$R^e$. In certain embodiments, $R^{10}$ is acetyl. In certain embodiments, $R^{10}$ is —C(=O)$OR^e$. In certain embodiments, $R^{10}$ is —C(=O)$N(R^e)_2$. In certain embodiments, $R^{10}$ is substituted alkyl. In certain embodiments, $R^{10}$ is unsubstituted alkyl. In certain embodiments, $R^{10}$ is $C_{1-6}$ alkyl. In certain embodiments, $R^{10}$ is methyl. In certain embodiments, $R^{10}$ is ethyl. In certain embodiments, $R^{10}$ is propyl. In certain embodiments, $R^{10}$ is butyl. In certain embodiments, $R^{10}$ is Ad. In certain embodiments, $R^{10}$ is substituted alkenyl. In certain embodiments, $R^{10}$ is unsubstituted alkenyl. In certain embodiments, $R^{10}$ is vinyl. In certain embodiments, $R^{10}$ is substituted alkynyl. In certain embodiments, $R^{10}$ is unsubstituted alkynyl. In certain embodiments, $R^{10}$ is ethynyl. In certain embodiments, $R^{10}$ is substituted carbocyclyl. In certain embodiments, $R^{10}$ is unsubstituted carbocyclyl. In certain embodiments, $R^{10}$ is cyclopropyl. In certain embodiments, $R^{10}$ is cyclobutyl. In certain embodiments, $R^{10}$ is cyclopentyl. In certain embodiments, $R^{10}$ is cyclohexyl. In certain embodiments, $R^{10}$ is cycloheptyl. In certain embodiments, $R^{10}$ is substituted heterocyclyl. In certain embodiments, $R^{10}$ is unsubstituted heterocyclyl. In certain embodiments, $R^{10}$ is substituted aryl. In certain embodiments, $R^{10}$ is unsubstituted aryl. In certain embodiments, $R^{10}$ is substituted phenyl. In certain embodiments, $R^{10}$ is unsubstituted phenyl. In certain embodiments, $R^{10}$ is substituted naphthyl. In certain embodiments, $R^{10}$ is unsubstituted naphthyl. In certain embodiments, $R^{10}$ is substituted heteroaryl. In certain embodiments, $R^{10}$ is unsubstituted heteroaryl. In certain embodiments, $R^{10}$ is monocyclic heteroaryl. In certain embodiments, $R^{10}$ is 5-membered monocyclic heteroaryl. In certain embodiments, $R^{10}$ is 5-membered monocyclic heteroaryl, wherein only one of the five atoms in the ring of the heteroaryl is selected from the group consisting of nitrogen, oxygen, and sulfur. In certain embodiments, $R^{10}$ is 5-membered monocyclic heteroaryl, wherein only two of the five atoms in the ring of the heteroaryl are independently selected from the group consisting of nitrogen, oxygen, and sulfur. In certain embodiments, $R^{10}$ is 5-membered monocyclic heteroaryl, wherein only three of the five atoms in the ring of the heteroaryl are independently selected from the group consisting of nitrogen, oxygen, and sulfur. In certain embodiments, $R^{10}$ is tetrazolyl. In certain embodiments, $R^{10}$ is 6-membered monocyclic heteroaryl. In certain embodiments, $R^{10}$ is 6-membered monocyclic heteroaryl, wherein only one of the six atoms in the ring of the heteroaryl is selected from the group consisting of nitrogen, oxygen, and sulfur. In certain embodiments, $R^{10}$ is 6-membered monocyclic heteroaryl, wherein only two of the six atoms in the ring of the heteroaryl are independently selected from the group consisting of nitrogen, oxygen, and sulfur. In certain embodiments, $R^{10}$ is triazinyl. In certain embodiments, $R^{10}$ is tetrazinyl. In certain embodiments, $R^{10}$ is bicyclic heteroaryl, wherein the point of attachment may be at any atom of the heteroaryl, as valency permits. In certain embodiments, $R^{10}$ is a monocyclic heteroaryl fused with phenyl. In certain embodiments, $R^{10}$ is a 5-membered monocyclic heteroaryl fused with phenyl. In certain embodiments, $R^{10}$ is a 6-membered monocyclic heteroaryl fused with phenyl. In certain embodiments, $R^{10}$ is a monocyclic heteroaryl fused with another monocyclic heteroaryl. In certain embodiments, $R^{10}$ is a 5-membered monocyclic heteroaryl fused with another 5-membered monocyclic heteroaryl. In certain embodiments, $R^{10}$ is a 5-membered monocyclic heteroaryl fused with a 6-membered monocyclic heteroaryl. In certain embodiments, $R^{10}$ is a 6-membered monocyclic heteroaryl fused with another 6-membered monocyclic heteroaryl. In certain embodiments, $R^{10}$ is —$OR^e$. In certain embodiments, $R^{10}$ is —OH when attached to an $sp^3$ carbon atom. In certain embodiments, $R^{10}$ is —$SR^e$. In certain embodiments, $R^{10}$ is —SH when attached to an $sp^3$ carbon atom. In certain embodiments, $R^{10}$ is —$N(R^e)_2$. In certain embodiments, $R^{10}$ is —$NH_2$ when attached to an $sp^3$ carbon atom. In certain embodiments, $R^{10}$ is —CN. In certain embodiments, $R^{10}$ is —SCN. In certain embodiments, $R^{10}$ is —C(=$NR^e$)$R^e$, —C(=$NR^e$)$OR^e$, or —C(=$NR^e$)$N(R^e)_2$. In certain embodiments, $R^{10}$ is —C(=O)$R^e$, —C(=O)$OR^e$, or —C(=O)N$(R^e)_2$. In certain embodiments, $R^{10}$ is —$NO_2$. In certain embodiments, $R^{10}$ is —$NR^e$C(=O)$R^e$, —$NR^e$C(=O)$OR^e$, or —$NR^e$C(=O)N$(R^e)$. In certain embodiments, $R^{10}$ is —OC(=O)$R^e$, —OC(=O)$OR^e$, or —OC(=O)N$(R^e)_2$. In certain embodiments, $R^{10}$ is —ON$(R^e)_2$.

In certain embodiments, at least one $R^e$ is H. In certain embodiments, at least one $R^e$ is substituted acyl. In certain embodiments, at least one $R^e$ is unsubstituted acyl. In certain embodiments, at least one $R^e$ is acetyl. In certain embodiments, at least one $R^e$ is substituted alkyl. In certain embodiments, at least one $R^e$ is unsubstituted alkyl. In certain embodiments, at least one $R^e$ is $C_{1-6}$ alkyl. In certain embodiments, at least one $R^e$ is methyl. In certain embodiments, at least one $R^e$ is ethyl. In certain embodiments, at least one $R^e$ is propyl. In certain embodiments, at least one $R^e$ is butyl. In certain embodiments, at least one $R^e$ is substituted alkenyl. In certain embodiments, at least one $R^e$ is unsubstituted alkenyl. In certain embodiments, at least one $R^e$ is vinyl. In certain embodiments, at least one $R^e$ is substituted alkynyl. In certain embodiments, at least one $R^e$ is unsubstituted alkynyl. In certain embodiments, at least one $R^e$ is ethynyl. In certain embodiments, at least one $R^e$ is substituted carbocyclyl. In certain embodiments, at least one $R^e$ is unsubstituted carbocyclyl. In certain embodiments, at least one $R^e$ is cyclopropyl. In certain embodiments, at least one $R^e$ is cyclobutyl. In certain embodiments, at least one $R^e$ is cyclopentyl. In certain embodiments, at least one $R^e$ is cyclohexyl. In certain embodiments, at least one $R^e$ is cycloheptyl. In certain embodiments, at least one $R^e$ is substituted heterocyclyl. In certain embodiments, at least one $R^e$ is unsubstituted heterocyclyl. In certain embodiments, at least one $R^e$ is substituted aryl. In certain embodiments, at least one $R^e$ is unsubstituted aryl. In certain embodiments, at least one $R^e$ is substituted phenyl. In certain embodiments, at least one $R^e$ is unsubstituted phenyl. In certain embodiments, at least one $R^e$ is substituted heteroaryl. In certain embodiments, at least one $R^e$ is unsubstituted heteroaryl. In certain embodiments, at least one $R^e$ is substituted pyridyl. In certain embodiments, at least one $R^e$ is unsubstituted pyridyl. In certain embodiments, at least one $R^e$ is a nitrogen protecting group when attached to a nitrogen atom. In certain embodiments, at least one $R^e$ is Bn, Boc, Cbz, Fmoc, trifluoroacetyl, triphenylmethyl, or Ts when attached to a nitrogen atom. In certain embodiments, at least one $R^e$ is an oxygen protecting group when attached to an oxygen atom. In certain embodiments, at least one $R^e$ is silyl, TBDPS, TBDMS, TIPS, TES, TMS, MOM, THP, t-Bu, Bn, allyl, acetyl, pivaloyl, or benzoyl when attached to an oxygen atom. In certain embodiments, two $R^e$ groups are joined to form a substituted heterocyclic ring. In certain embodiments, two $R^e$ groups are joined to form an unsubstituted heterocyclic ring. In certain embodiments, two $R^e$ groups are joined to form a substituted heteroaryl ring. In certain embodiments, two $R^e$ groups are joined to form an unsubstituted heteroaryl ring.

In compounds of Formulae (II-1) and (F), any two of $R^7$, $R^8$, $R^9$, $R^{10}$, $R^c$, and $R^d$ groups may be joined to form a optionally substituted carbocyclyl ring, or optionally substituted heterocyclic ring. In certain embodiments, two of $R^7$, $R^8$, $R^9$, $R^{10}$, $R^c$, and $R^d$ groups are joined to form a optionally substituted cyclopropyl ring. In certain embodiments, two of $R^7$, $R^8$, $R^9$, $R^{10}$, $R^c$, and $R^d$ groups are joined to form a optionally substituted cyclobutyl ring. In certain embodiments, two of $R^7$, $R^8$, $R^9$, $R^{10}$, $R^c$, and $R^d$ groups are joined to form a optionally substituted cyclopentyl ring. In certain embodiments, two of $R^7$, $R^8$, $R^9$, $R^{10}$, $R^c$, and $R^d$ groups are joined to form a optionally substituted cyclohexyl ring. In certain embodiments, two of $R^7$, $R^8$, $R^9$, $R^{10}$, $R^c$, and $R^d$ groups are joined to form a optionally substituted cycloheptyl ring. In certain embodiments, two of $R^7$, $R^8$, $R^9$, $R^{10}$, $R^c$, and $R^d$ groups are joined to form a optionally substituted cyclooctyl ring. In certain embodiments, two of $R^7$, $R^8$, $R^9$, $R^{10}$, $R^c$, and $R^d$ groups are joined to form a optionally substituted cyclononyl ring. In certain embodiments, two of $R^7$, $R^8$, $R^9$, $R^{10}$, $R^c$, and $R^d$ groups are joined to form a optionally substituted cyclodecyl ring. In certain embodiments, two of $R^7$, $R^8$, $R^9$, $R^{10}$, $R^c$, and $R^d$ groups are joined to form a optionally substituted 4-membered heterocyclic ring. In certain embodiments, two of $R^7$, $R^8$, $R^9$, $R^{10}$, $R^c$, and $R^d$ groups are joined to form a optionally substituted 5-membered heterocyclic ring. In certain embodiments, two of $R^7$, $R^8$, $R^9$, $R^{10}$, $R^c$, and $R^d$ groups are joined to form a optionally substituted 6-membered heterocyclic ring. In certain embodiments, two of $R^7$, $R^8$, $R^9$, $R^{10}$, $R^c$, and $R^d$ groups are joined to form a optionally substituted 7-membered heterocyclic ring. In certain embodiments, two of $R^7$, $R^8$, $R^9$, $R^{10}$, $R^e$, and $R^d$ groups are joined to form a optionally substituted 8-membered heterocyclic ring. In certain embodiments, two of $R^7$, $R^8$, $R^9$, $R^{10}$, $R^e$, and $R^d$ groups are joined to form a optionally substituted 9-membered heterocyclic ring. In certain embodiments, two of $R^7$, $R^8$, $R^9$, $R^{10}$, $R^c$, and $R^d$ groups are joined to form a optionally substituted 10-membered heterocyclic ring. In certain embodiments, $R^7$ and $R^8$ are joined to form a optionally substituted carbocyclyl ring. In certain embodiments, $R^7$ and $R^8$ are joined to form a optionally substituted heterocyclic ring. In certain embodiments, $R^7$ and $R^9$ are joined to form a optionally substituted carbocyclyl ring. In certain embodiments, $R^7$ and $R^9$ are joined to form a optionally substituted heterocyclic ring. In certain embodiments, $R^7$ and $R^{10}$ are joined to form a optionally substituted carbocyclyl ring. In certain embodiments, $R^7$ and $R^{10}$ are joined to form a optionally substituted heterocyclic ring. In certain embodiments, $R^7$ and $R^c$ are joined to form a optionally substituted carbocyclyl ring. In certain embodiments, $R^7$ and $R^c$ are joined to form a optionally substituted heterocyclic ring. In certain embodiments, $R^7$ and $R^d$ are joined to form a optionally substituted carbocyclyl ring. In certain embodiments, $R^7$ and $R^d$ are joined to form a optionally substituted heterocyclic ring. In certain embodiments, $R^8$ and $R^9$ are joined to form a optionally substituted carbocyclyl ring. In certain embodiments, $R^8$ and $R^9$ are joined to form a optionally substituted heterocyclic ring. In certain embodiments, $R^8$ and $R^{10}$ are joined to form a optionally substituted carbocyclyl ring. In certain embodiments, $R^8$ and $R^{10}$ are joined to form a optionally substituted heterocyclic ring. In certain embodiments, $R^8$ and $R^c$ are joined to form a optionally substituted carbocyclyl ring. In certain embodiments, $R^8$ and $R^c$ are joined to form a optionally substituted heterocyclic ring. In certain embodiments, $R^8$ and $R^d$ are joined to form a optionally substituted carbocyclyl ring. In certain embodiments, $R^e$ and $R^d$ are joined to form a optionally substituted heterocyclic ring. In certain embodiments, $R^9$ and $R^{10}$ are joined to form a optionally substituted carbocyclyl ring. In certain embodiments, $R^9$ and $R^{10}$ are joined to form a optionally substituted heterocyclic ring. In certain embodiments, $R^9$ and $R^c$ are joined to form a optionally substituted carbocyclyl ring. In certain embodiments, $R^9$ and $R^c$ are joined to form a optionally substituted heterocyclic ring. In certain embodiments, $R^9$ and $R^d$ are joined to form a optionally substituted carbocyclyl ring. In certain embodiments, $R^9$ and $R^d$ are joined to form a optionally substituted heterocyclic ring. In certain embodiments, $R^{10}$ and $R^c$ are joined to form a optionally substituted carbocyclyl ring. In certain embodiments, $R^{10}$ and $R^c$ are joined to form a optionally substituted heterocyclic ring. In certain embodiments, $R^{10}$ and $R^d$ are joined to form a optionally substituted carbocyclyl ring. In certain embodiments, $R^{10}$ and $R^d$ are joined to form a optionally substituted heterocyclic ring. In certain embodiments, $R^c$ and $R^d$ are joined to form a optionally substituted carbocyclyl ring. In certain embodiments, $R^c$ and $R^d$ are joined to form a optionally substituted heterocyclic ring.

In certain embodiments, $R^7$ and $R^8$ are each independently selected from the group consisting of substituted alkyl, unsubstituted alkyl, substituted alkenyl, unsubstituted alkenyl, substituted alkynyl, and unsubstituted alkynyl. In certain embodiments, $R^7$ and $R^8$ are each independently selected from the group consisting of substituted alkyl and unsubstituted alkyl. In certain embodiments, $R^7$ and $R^8$ are each $C_{1-6}$ alkyl. In certain embodiments, $R^7$ and $R^8$ are each methyl. In certain embodiments, $R^7$ and $R^8$ are each independently selected from the group consisting of methyl, ethyl, propyl, and butyl.

In certain embodiments, $R^7$ is optionally substituted alkyl; and $R^8$ is optionally substituted aryl. In certain embodiments, $R^7$ is optionally substituted alkyl; and $R^8$ is optionally substituted phenyl. In certain embodiments, $R^7$ is $C_{1-6}$ alkyl; and $R^8$ is optionally substituted aryl. In certain embodiments, $R^7$ is $C_{1-6}$ alkyl; and $R^8$ is optionally substituted phenyl. In certain embodiments, $R^7$ is methyl; and $R^8$ is phenyl. In certain embodiments, $R^8$ is optionally substituted alkyl; and $R^7$ is optionally substituted aryl. In certain embodiments, $R^8$ is optionally substituted alkyl; and $R^7$ is optionally substituted phenyl. In certain embodiments, $R^8$ is $C_{1-6}$ alkyl; and $R^7$ is optionally substituted aryl. In certain embodiments, $R^8$ is $C_{1-6}$ alkyl; and $R^7$ is optionally substituted phenyl. In certain embodiments, $R^8$ is methyl; and $R^7$ is phenyl.

In certain embodiments, $R^7$ is H; and $R^8$ is substituted alkyl. In certain embodiments, $R^7$ is H; and $R^8$ is unsubstituted alkyl. In certain embodiments, $R^7$ is H; and $R^8$ is $C_{1-6}$ alkyl. In certain embodiments, $R^7$ is H; and $R^8$ is methyl. In certain embodiments, $R^7$ is H; and $R^8$ is ethyl. In certain embodiments, $R^7$ is H; and $R^8$ is propyl. In certain embodiments, $R^7$ is H; and $R^8$ is butyl. In certain embodiments, $R^7$ is H; and $R^8$ is substituted alkenyl. In certain embodiments, $R^7$ is H; and $R^8$ is unsubstituted alkenyl. In certain embodiments, $R^7$ is H; and $R^8$ is $C_{1-6}$ alkenyl. In certain embodiments, $R^7$ is H; and $R^8$ is vinyl. In certain embodiments, $R^7$ is H; and $R^8$ is allyl. In certain embodiments, $R^7$ is H; and $R^8$ is 4-butenyl. In certain embodiments, $R^7$ is H; and $R^8$ is substituted alkynyl. In certain embodiments, $R^7$ is H; and $R^8$ is unsubstituted alkynyl. In certain embodiments, $R^7$ is H; and $R^8$ is $C_{1-6}$ alkynyl. In certain embodiments, $R^7$ is H; and $R^8$ is ethynyl. In certain embodiments, $R^7$ is H; and $R^8$ is substituted aryl. In certain embodiments, $R^7$ is H; and $R^8$ is unsubstituted aryl. In certain embodiments, $R^7$ is H; and $R^8$ is substituted phenyl. In certain embodiments, $R^7$ is H; and $R^8$ is unsubstituted phenyl. In certain embodiments, $R^7$ is H; and $R^8$ is substituted heteroaryl. In certain embodiments, $R^7$ is H; and $R^8$ is unsubstituted heteroaryl. In certain embodiments, $R^7$ is H; and $R^8$ is substituted pyridyl. In certain embodiments, $R^7$ is H; and $R^8$ is unsubstituted pyridyl. In certain embodiments, $R^7$ is H; and $R^8$ is $—OR^e$. In certain embodiments, $R^7$ is H; and $R^8$ is —O-aryl. In certain embodiments, $R^7$ is H; and $R^8$ is —OPh. In certain embodiments, $R^7$ is H; and $R^8$ is $—O—C_{1-6}$ alkyl. In certain embodiments, $R^7$ is H; and $R^8$ is —OH. In certain embodiments, $R^7$ is H; and $R^8$ is $—N(R^e)_2$. In certain embodiments, $R^7$ is H; and $R^8$ is $—N(C_{1-6}$ alkyl$)_2$. In certain embodiments, $R^7$ is H; and $R^8$ is $—NH_2$. In certain embodiments, $R^7$ is H; and $R^8$ is $—C(=O)OR^e$. In certain embodiments, $R^7$ is H; and $R^8$ is —C(=O)OMe. In certain embodiments, $R^7$ is H; and $R^8$ is —C(=O)OEt.

In certain embodiments, $R^8$ is H; and $R^7$ is substituted alkyl. In certain embodiments, $R^8$ is H; and $R^7$ is unsubstituted alkyl. In certain embodiments, $R^8$ is H; and $R^7$ is $C_{1-6}$ alkyl. In certain embodiments, $R^8$ is H; and $R^7$ is methyl. In certain embodiments, $R^8$ is H; and $R^7$ is ethyl. In certain embodiments, $R^8$ is H; and $R^7$ is propyl. In certain embodiments, $R^8$ is H; and $R^7$ is butyl. In certain embodiments, $R^8$ is H; and $R^7$ is substituted alkenyl. In certain embodiments, $R^8$ is H; and $R^7$ is unsubstituted alkenyl. In certain embodiments, $R^8$ is H; and $R^7$ is $C_{1-6}$ alkenyl. In certain embodiments, $R^8$ is H; and $R^7$ is vinyl. In certain embodiments, $R^8$ is H; and $R^7$ is allyl. In certain embodiments, $R^8$ is H; and $R^7$ is 4-butenyl. In certain embodiments, $R^8$ is H; and $R^7$ is substituted alkynyl. In certain embodiments, $R^8$ is H; and $R^7$ is unsubstituted alkynyl. In certain embodiments, $R^8$ is H; and $R^7$ is $C_{1-6}$ alkynyl. In certain embodiments, $R^8$ is H; and $R^7$ is ethynyl. In certain embodiments, $R^8$ is H; and $R^7$ is substituted aryl. In certain embodiments, $R^8$ is H; and $R^7$ is unsubstituted aryl. In certain embodiments, $R^8$ is H; and $R^7$ is substituted phenyl. In certain embodiments, $R^8$ is H; and $R^7$ is unsubstituted phenyl. In certain embodiments, $R^8$ is H; and $R^7$ is substituted heteroaryl. In certain embodiments, $R^8$ is H; and $R^7$ is unsubstituted heteroaryl. In certain embodiments, $R^8$ is H; and $R^7$ is substituted pyridyl. In certain embodiments, $R^8$ is H; and $R^7$ is unsubstituted pyridyl. In certain embodiments, $R^8$ is H; and $R^7$ is $—OR^e$. In certain embodiments, $R^8$ is H; and $R^7$ is —O-aryl. In certain embodiments, $R^8$ is H; and $R^7$ is —OPh. In certain embodiments, $R^8$ is H; and $R^7$ is $—O—C_{1-4}$ alkyl. In certain embodiments, $R^8$ is H; and $R^7$ is —OH. In certain embodiments, $R^8$ is H; and $R^7$ is $—N(R^e)_2$. In certain embodiments, $R^8$ is H; and $R^7$ is $—N(C_{1-6}$ alkyl$)_2$. In certain embodiments, $R^8$ is H; and $R^7$ is $—NH_2$. In certain embodiments, $R^8$ is H; and $R^7$ is $—C(=O)OR^e$. In certain embodiments, $R^8$ is H; and $R^7$ is —C(=O)OMe. In certain embodiments, $R^8$ is H; and $R^7$ is —C(=O)OEt.

In certain embodiments, $R^7$ and $R^8$ are each H.

In certain embodiments, $R^9$ and $R^{10}$ are each independently selected from the group consisting of substituted alkyl, unsubstituted alkyl, substituted alkenyl, unsubstituted alkenyl, substituted alkynyl, and unsubstituted alkynyl. In certain embodiments, $R^9$ and $R^{10}$ are each independently selected from the group consisting of substituted alkyl and unsubstituted alkyl. In certain embodiments, $R^9$ and $R^{10}$ are each $C_{1-6}$ alkyl. In certain embodiments, $R^9$ and $R^{10}$ are each methyl. In certain embodiments, $R^9$ and $R^{10}$ are each independently selected from the group consisting of methyl, ethyl, propyl, and butyl.

In certain embodiments, $R^9$ is optionally substituted alkyl; and $R^{10}$ is optionally substituted aryl. In certain embodiments, $R^9$ is optionally substituted alkyl; and $R^1$ is optionally substituted phenyl. In certain embodiments, $R^9$ is $C_{1-4}$ alkyl; and $R^{10}$ is optionally substituted aryl. In certain embodiments, $R^9$ is $C_{1-6}$ alkyl; and $R^{10}$ is optionally substituted phenyl. In certain embodiments, $R^9$ is methyl; and $R^{10}$ is phenyl. In certain embodiments, $R^{10}$ is optionally substituted alkyl; and $R^9$ is optionally substituted aryl. In certain embodiments, $R^{10}$ is optionally substituted alkyl; and $R^9$ is optionally substituted phenyl. In certain embodiments, $R^{10}$ is $C_{1-6}$ alkyl; and $R^9$ is optionally substituted aryl. In certain embodiments, $R^{10}$ is $C_{1-6}$ alkyl; and $R^9$ is optionally substituted phenyl. In certain embodiments, $R^{10}$ is methyl; and $R^9$ is phenyl.

In certain embodiments, $R^9$ is H; and $R^{10}$ is substituted alkyl. In certain embodiments, $R^9$ is H; and $R^{10}$ is unsubstituted alkyl. In certain embodiments, $R^9$ is H; and $R^{10}$ is $C_{1-6}$ alkyl. In certain embodiments, $R^9$ is H; and $R^{10}$ is methyl. In certain embodiments, $R^9$ is H; and $R^{10}$ is ethyl. In certain embodiments, $R^9$ is H; and $R^{10}$ is propyl. In certain embodiments, $R^9$ is H; and $R^{10}$ is butyl. In certain embodiments, $R^9$ is H; and $R^{10}$ is substituted alkenyl. In certain embodiments, $R^9$ is H; and $R^{10}$ is unsubstituted alkenyl. In certain embodiments, $R^9$ is H; and $R^{10}$ is $C_{1-6}$ alkenyl. In certain embodiments, $R^9$ is H; and $R^{10}$ is vinyl. In certain embodiments, $R^9$ is H; and $R^{10}$ is allyl. In certain embodiments, $R^9$ is H; and $R^{10}$ is 4-butenyl. In certain embodiments, $R^9$ is H; and $R^{10}$ is substituted alkynyl. In certain embodiments, $R^9$ is H; and $R^{10}$ is unsubstituted alkynyl. In certain embodiments, $R^9$ is H; and $R^{10}$ is $C_{1-6}$ alkynyl. In certain embodiments, $R^9$ is H; and $R^{10}$ is ethynyl. In certain embodiments, $R^9$ is H; and $R^{10}$ is substituted aryl. In certain embodiments, $R^9$ is H; and $R^{10}$ is unsubstituted aryl. In certain embodiments, $R^9$ is H; and $R^{10}$ is substituted phenyl. In certain embodiments, $R^9$ is H; and $R^{10}$ is unsubstituted phenyl. In certain embodiments, $R^9$ is H; and $R^{10}$ is substituted heteroaryl. In certain embodiments, $R^9$ is H; and $R^{10}$ is unsubstituted heteroaryl. In certain embodiments, $R^9$ is H; and $R^{10}$ is substituted pyridyl. In certain embodiments, $R^9$ is H; and $R^{10}$ is unsubstituted pyridyl. In certain embodiments, $R^9$ is H; and $R^{10}$ is —$OR^e$. In certain embodiments, $R^9$ is H; and $R^{10}$ is —O-aryl. In certain embodiments, $R^9$ is H; and $R^{10}$ is —OPh. In certain embodiments, $R^9$ is H; and $R^{10}$ is —O—$C_{1-6}$ alkyl. In certain embodiments, $R^9$ is H; and $R^{10}$ is —OH. In certain embodiments, $R^9$ is H; and $R^{10}$ is —$N(R^e)_2$. In certain embodiments, $R^9$ is H; and $R^{10}$ is —$N(C_{1-6}$ alkyl$)_2$. In certain embodiments, $R^9$ is H; and $R^{10}$ is —$NH_2$. In certain embodiments, $R^9$ is H; and $R^{10}$ is —C(=O)$OR^e$. In certain embodiments, $R^9$ is H; and $R^{10}$ is —C(=O)OMe. In certain embodiments, $R^9$ is H; and $R^{10}$ is —C(=O)OEt.

In certain embodiments, $R^{10}$ is H; and $R^9$ is substituted alkyl. In certain embodiments, $R^{10}$ is H; and $R^9$ is unsubstituted alkyl. In certain embodiments, $R^{10}$ is H; and $R^9$ is $C_{1-6}$ alkyl. In certain embodiments, $R^{10}$ is H; and $R^9$ is methyl. In certain embodiments, $R^{10}$ is H; and $R^9$ is ethyl. In certain embodiments, $R^{10}$ is H; and $R^9$ is propyl. In certain embodiments, $R^{10}$ is H; and $R^9$ is butyl. In certain embodiments, $R^{10}$ is H; and $R^9$ is substituted alkenyl. In certain embodiments, $R^{10}$ is H; and $R^9$ is unsubstituted alkenyl. In certain embodiments, $R^{10}$ is H; and $R^9$ is $C_{1-6}$ alkenyl. In certain embodiments, $R^{10}$ is H; and $R^9$ is vinyl. In certain embodiments, $R^{10}$ is H; and $R^9$ is allyl. In certain embodiments, $R^{10}$ is H; and $R^9$ is 4-butenyl. In certain embodiments, $R^{10}$ is H; and $R^9$ is substituted alkynyl. In certain embodiments, $R^{10}$ is H; and $R^9$ is unsubstituted alkynyl. In certain embodiments, $R^{10}$ is H; and $R^9$ is $C_{1-6}$ alkynyl. In certain embodiments, $R^{10}$ is H; and $R^9$ is ethynyl. In certain embodiments, $R^{10}$ is H; and $R^9$ is substituted aryl. In certain embodiments, $R^{10}$ is H; and $R^9$ is unsubstituted aryl. In certain embodiments, $R^{10}$ is H; and $R^9$ is substituted phenyl. In certain embodiments, $R^{10}$ is H; and $R^9$ is unsubstituted phenyl. In certain embodiments, $R^{10}$ is H; and $R^9$ is substituted heteroaryl. In certain embodiments, $R^{10}$ is H; and $R^9$ is unsubstituted heteroaryl. In certain embodiments, $R^{10}$ is H; and $R^9$ is substituted pyridyl. In certain embodiments, $R^{10}$ is H; and $R^9$ is unsubstituted pyridyl. In certain embodiments, $R^{10}$ is H; and $R^9$ is —$OR^e$. In certain embodiments, $R^{10}$ is H; and $R^9$ is —O-aryl. In certain embodiments, $R^{10}$ is H; and $R^9$ is —OPh. In certain embodiments, $R^{10}$ is H; and $R^9$ is —O—$C_{1-6}$ alkyl. In certain embodiments, $R^{10}$ is H; and $R^9$ is —OH. In certain embodiments, $R^{10}$ is H; and $R^9$ is —$N(R^e)_2$. In certain embodiments, $R^{10}$ is H; and $R^9$ is —$N(C_{1-6}$ alkyl$)_2$. In certain embodiments, $R^{10}$ is H; and $R^9$ is —$NH_2$. In certain embodiments, $R^{10}$ is H; and $R^9$ is —C(=O)$OR^e$. In certain embodiments, $R^{10}$ is H; and $R^9$ is —C(=O)OMe. In certain embodiments, $R^{10}$ is H; and $R^9$ is —C(=O)OEt.

In certain embodiments, $R^9$ and $R^{10}$ are each H.

In certain embodiments, $R^7$, $R^8$, $R^9$, and $R^{10}$ are each H.

Compounds of Formula (G) include a ligand Y bound to the $Fe^{II}$ atom. Y may be any ligand capable of binding to the $Fe^{II}$ atom to form a coordination complex. In certain embodiments, Y is a compound including one or more electron donating moieties. In certain embodiments, Y a compound including one or more heteroatoms. In certain embodiments, Y is a solvent. In certain embodiments, Y is $N(R^f)_3$. In certain embodiments, Y is $NEt_3$. In certain embodiments, Y is (i-Pr)$_2$NEt. In certain embodiments, Y is $R^f$—O—$R^f$. In certain embodiments, Y is $R^f$—O—$R^f$; and each occurrence of $R^f$ is independently optionally substituted alkyl. In certain embodiments, Y is $R^f$—O—$R^f$; and each occurrence of $R^f$ is independently $C_{1-6}$ alkyl. In certain embodiments, Y is diethyl ether. In certain embodiments, Y is methyl t-butyl ether. In certain embodiments, Y is $R^f$—S—$R^f$. In certain embodiments, Y is dimethyl sulfide. In certain embodiments, Y is diethyl sulfide. In certain embodiments, Y is substituted heterocyclyl. In certain embodiments, Y is unsubstituted heterocyclyl. In certain embodiments, Y is substituted tetrahydrofuran. In certain embodiments, Y is 2-methyltetrahydrofuran. In certain embodiments, Y is unsubstituted tetrahydrofuran. In certain embodiments, Y is substituted tetrahydropyran. In certain embodiments, Y is unsubstituted tetrahydropyran. In certain embodiments, Y is substituted heteroaryl. In certain embodiments, Y is unsubstituted heteroaryl. In certain embodiments, Y is substituted pyridine. In certain embodiments, Y is 2,6-lutidine. In certain embodiments, Y is unsubstituted pyridine.

In certain embodiments, $R^f$ is substituted alkyl. In certain embodiments, $R^f$ is unsubstituted alkyl. In certain embodiments, $R^f$ is $C_{1-6}$ alkyl. In certain embodiments, $R^f$ is methyl. In certain embodiments, $R^f$ is ethyl. In certain embodiments, $R^f$ is propyl. In certain embodiments, $R^f$ is butyl. In certain embodiments, $R^f$ is Ad. In certain embodiments, $R^f$ is substituted alkenyl. In certain embodiments, $R^f$ is unsubstituted alkenyl. In certain embodiments, $R^f$ is vinyl. In certain embodiments, $R^f$ is substituted alkynyl. In certain embodiments, $R^f$ is unsubstituted alkynyl. In certain embodiments, $R^f$ is ethynyl. In certain embodiments, $R^f$ is substituted carbocyclyl. In certain embodiments, $R^f$ is unsubstituted carbocyclyl. In certain embodiments, $R^f$ is cyclopropyl. In certain embodiments, $R^f$ is cyclobutyl. In certain embodiments, $R^f$ is cyclopentyl. In certain embodiments, $R^f$ is cyclohexyl. In certain embodiments, $R^f$ is cycloheptyl. In certain embodiments, $R^f$ is substituted heterocyclyl. In certain embodiments, $R^f$ is unsubstituted heterocyclyl. In certain embodiments, $R^f$ is substituted aryl. In certain embodiments, $R^f$ is unsubstituted aryl. In certain embodiments, $R^f$ is substituted phenyl. In certain embodiments, $R^f$ is unsubstituted phenyl. In certain embodiments, $R^f$ is substituted heteroaryl. In certain embodiments, $R^f$ is unsubstituted heteroaryl. In certain embodiments, $R^f$ is substituted pyridyl. In certain embodiments, $R^f$ is unsubstituted pyridyl.

Figure 3:
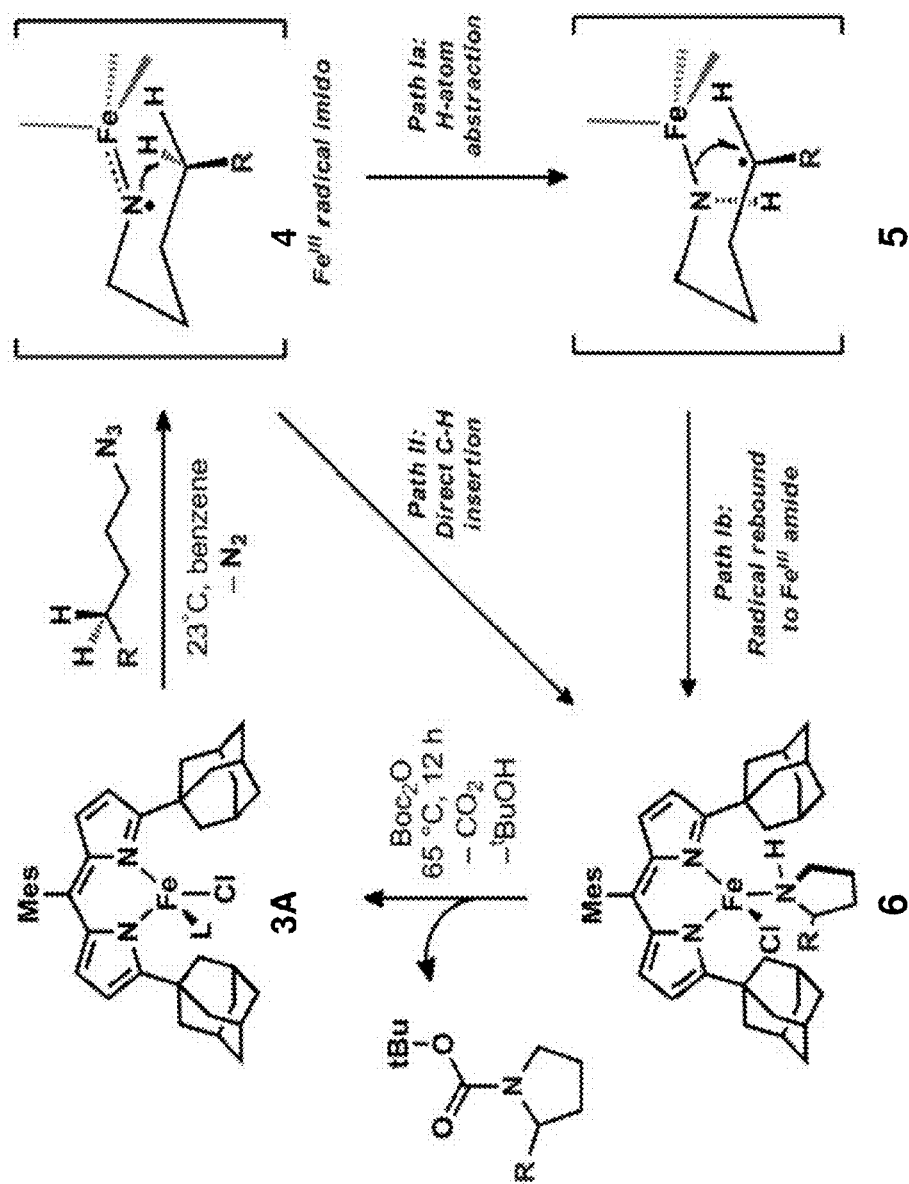
FIG. 3 illustrates a proposed mechanism of an intramolecular C—H amination reaction catalyzed by $Fe^{II}$-dipyrromethene complex 3A to yield cyclic amines.

Shown in FIG. 3 is a proposed mechanism for the intramolecular C—H amination reaction of an azide R″CH(R‴)$N_3$ (e.g., R(CH$_2$)$_4$N$_3$), catalyzed by a $Fe^{II}$Cl(L)-dipyrromethene complex (e.g., 3A), to yield a

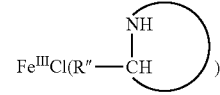

dipyrromethene complex

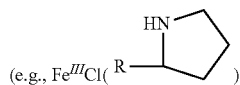

dipyrromethene complex). First, the $Fe^{II}Cl(L)$-dipyrromethene complex undergoes a ligand exchange to form radical imido intermediate 4. The intermediate 4 abstracts a hydrogen atom intramolecularly from a C—H moiety of intermediate 4 to give rise to intermediate 5. Radical recombination furnishes the C—H amination product 6. The net effect of the reaction is the transfer of the nitrene group N: of R"CH(R'")N: (e.g., $R(CH_2)_4N$:) to the C—H of R"CH (R'")N. The mechanism for a similar reaction using compound 3B as the catalyst instead of 3A is similar to or the same as the mechanism described herein.

The acyclic secondary amines may be synthesized under any suitable conditions described herein.

Synthesis of Protected Cyclic Secondary Amines

The method of preparing a compound of Formula (II-1), or a salt or stereoisomer thereof, which is a coordination complex of a cyclic secondary amine and ferrous compound, may further comprise the step of:

reacting the compound of Formula (II-1), or a salt or stereoisomer thereof, with $Boc_2O$ to provide a compound of Formula (II-2-A), which is a Boc-protected cyclic secondary amine:

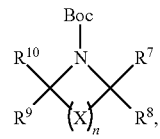

(II-2-A)

or a salt or stereoisomer thereof; wherein X, n, $R^7$, $R^8$, $R^9$, and $R^{10}$ are as defined herein.

Exemplary compounds of Formula (II-2-A) that can be prepared by the inventive methods include, but are not limited to:

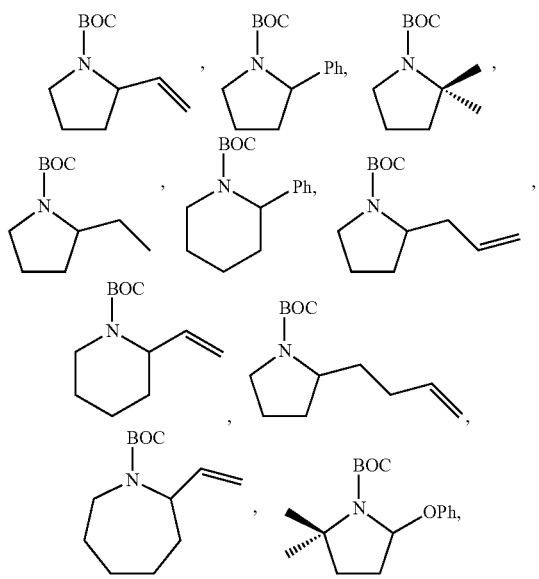

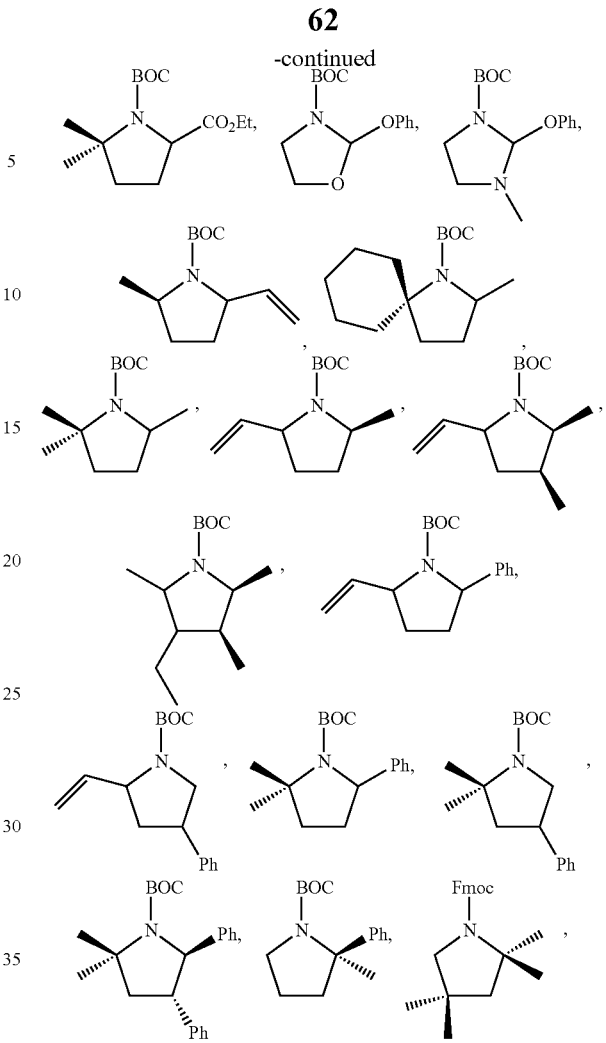

and salts and stereoisomers thereof.

The method of preparing a compound of Formula (II-1), or a salt or stereoisomer thereof, which is a coordination complex of a cyclic secondary amine and ferrous compound, may further comprise the step of:

reacting the compound of Formula (II-1), or a salt or stereoisomer thereof, with Fmoc-OSuc to provide a compound of Formula (II-2-B), which is a Fmoc-protected cyclic secondary amine:

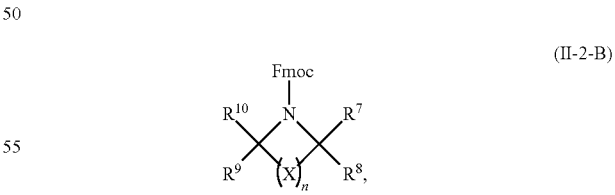

(II-2-B)

or a salt or stereoisomer thereof; wherein X, n, $R^7$, $R^8$, $R^9$, and $R^{10}$ are as defined herein.

The protected cyclic secondary amines may be synthesized under any suitable conditions described herein.

Synthesis of Cyclic Secondary Amines

The method of preparing a compound of Formula (II-2-A) or (II-2-B), or a salt or stereoisomer thereof, which is a Boc- or Fmoc-protected cyclic secondary amine, may further comprise the step of:

deprotecting the compound of Formula (II-2-A) or (II-2-B), or a salt or stereoisomer thereof, to provide a cyclic amine of Formula (II-3):

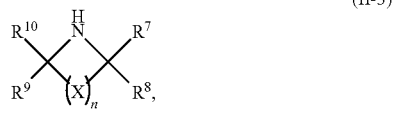

(II-3)

or a salt or stereoisomer thereof; wherein X, n, $R^7$, $R^8$, $R^9$, and $R^{10}$ are as defined herein.

The step of deprotecting a compound of Formula (II-2-A) or (II-2-B), or a salt or stereoisomer thereof, may also comprise deprotecting the compound of Formula (II-2-A) or (II-2-B), or a salt or stereoisomer thereof, under suitable conditions to remove the protecting group. The step of deprotecting a compound of Formula (II-2-A), or a salt or stereoisomer thereof, may comprise increasing the temperature of the compound of Formula (II-2-A), or a salt or stereoisomer thereof, above room temperature. In certain embodiments, the temperature of the compound of Formula (II-2-A), or a salt or stereoisomer thereof, is increased to at least 100° C. In certain embodiments, the temperature of the compound of Formula (II-2-A), or a salt or stereoisomer thereof, is increased to at least 150° C. In certain embodiments, the temperature of the compound of Formula (II-2-A), or a salt or stereoisomer thereof, is increased to at least 200° C. In certain embodiments, the temperature of the compound of Formula (II-2-A), or a salt or stereoisomer thereof, is increased to at least 250° C.

The suitable conditions in the step of deprotecting a compound of Formula (II-2-A), or a salt or stereoisomer thereof, may be acidic conditions. In certain embodiments, the deprotection step comprises reacting an acidic compound with the compound of Formula (II-2-A), or a salt or stereoisomer thereof, to remove the protecting group. In certain embodiments, the acidic compound is an inorganic acid. In certain embodiments, the inorganic acid is HCl. In certain embodiments, the inorganic acid is HBr. In certain embodiments, the inorganic acid is HI. In certain embodiments, the inorganic acid is $HClO_4$. In certain embodiments, the inorganic acid is $HNO_3$. In certain embodiments, the inorganic acid is $H_2SO_4$. In certain embodiments, the inorganic acid is $H_3PO_4$. In certain embodiments, the acidic compound is an organic acid. In certain embodiments, the organic acid is trifluoroacetic acid. In certain embodiments, the organic acid is a sulfonic acid. In certain embodiments, the organic acid is methanesulfonic acid. In certain embodiments, the organic acid is trifluoromethanesulfonic acid. In certain embodiments, the organic acid is p-toluenesulfonic acid. In certain embodiments, the organic acid is benzenesulfonatic acid. In certain embodiments, the acidic compound is a trialkylsilyl halide. In certain embodiments, the trialkylsilyl halide is trimethylsilyl chloride. In certain embodiments, the trialkylsilyl halide is trimethylsilyl bromide. In certain embodiments, the trialkylsilyl halide is trimethylsilyl iodide. In certain embodiments, the acidic compound is trimethylsilyl trifluoromethanesulfonate. In certain embodiments, the acidic compound is tetrabutylammonium fluoride. In certain embodiments, the acidic compound is a Lewis acid. In certain embodiments, the Lewis acid is boron trifluoride etherate.

The suitable conditions in the step of deprotecting a compound of Formula (II-2-A) or (II-2-B), or a salt or stereoisomer thereof, may be nucleophilic conditions. In certain embodiments, the deprotection step comprises reacting an nucleophilic compound with the compound of Formula (II-2-A) or (II-2-B), or a salt or stereoisomer thereof, to remove the protecting group. In certain embodiments, the suitable conditions in the deprotection step comprise use of a nucleophilic compound. In certain embodiments, the nucleophilic compound is alkyl lithium. In certain embodiments, the nucleophilic compound is LiMe. In certain embodiments, the nucleophilic compound is n-BuLi. In certain embodiments, the nucleophilic compound is sec-BuLi. In certain embodiments, the nucleophilic compound is t-BuLi. In certain embodiments, the nucleophilic compound is aryl lithium. In certain embodiments, the nucleophilic compound is LiPh. In certain embodiments, the nucleophilic compound is a Grignard reagent. In certain embodiments, the nucleophilic compound is MeMgCl, MeMgBr, or MeMgI. In certain embodiments, the nucleophilic compound is EtMgCl, EtMgBr, or EtMgI. In certain embodiments, the nucleophilic compound is PhMgCl, PhMgBr, or PhMgI. In certain embodiments, the nucleophilic compound is TMSMgCl or TMSMgBr. In certain embodiments, the nucleophilic compound is ammonia. In certain embodiments, the nucleophilic compound is ammonium hydroxide. In certain embodiments, the nucleophilic compound is a primary amine. In certain embodiments, the nucleophilic compound is methylamine, ethylamine, n-propylamine, isopropylamine, n-butylamine, n-pentylamine, n-hexylamine, cyclohexylamine, ethanolamine (i.e., 2-aminoethanol), Tris (i.e., 2-amino-2-hydroxymethyl-propane-1,3-diol), ethylenediamine, triethylenediamine, or aniline. In certain embodiments, the nucleophilic compound is a secondary amine. In certain embodiments, the nucleophilic compound is dimethylamine, diethylamine, di-n-propylamine, diisopropylamine, ethylisopropylamine, dicyclohexylamine, methylethanolamine, pyrrolidine, piperidine, morpholine, piperazine, or 1,4-bis-(3-aminopropyl)piperazine. In certain embodiments, the nucleophilic compound is a tertiary amine. In certain embodiments, the nucleophilic compound is trimethylamine, triethylamine, diisopropylethylamine (DIPEA), tri-n-butylamine, 4-dimethylaminopyridine (DMAP), or 1,8-diazabicyclo[5.4.0]undec-7-ene (DBU).

The suitable conditions in the step of deprotecting a compound of Formula (II-2-B), or a salt or stereoisomer thereof, may be basic conditions. In certain embodiments, the deprotection step comprises reacting an basic compound with the compound of Formula (II-2-B), or a salt or stereoisomer thereof, to remove the protecting group. In certain embodiments, the suitable conditions in the deprotection step comprise use of a basic compound. In certain embodiments, the basic compound is alkyl lithium. In certain embodiments, the basic compound is LiMe. In certain embodiments, the basic compound is n-BuLi. In certain embodiments, the basic compound is sec-BuLi. In certain embodiments, the basic compound is t-BuLi. In certain embodiments, the basic compound is aryl lithium. In certain embodiments, the basic compound is LiPh. In certain embodiments, the basic compound is a Grignard reagent. In certain embodiments, the basic compound is MeMgCl, MeMgBr, or MeMgI. In certain embodiments, the basic compound is EtMgCl, EtMgBr, or EtMgI. In certain embodiments, the basic compound is PhMgCl, PhMgBr, or PhMgI. In certain embodiments, the basic compound is TMSMgCl or TMSMgBr. In certain embodiments, the basic compound is ammonia. In certain embodiments, the basic compound is ammonium hydroxide. In certain embodiments, the basic compound is a primary amine. In certain embodiments, the basic compound is methylamine, ethylamine, n-propylamine, isopropylamine, n-butylamine, n-pentylamine, n-hexylamine, cyclohexylamine, ethanolamine (i.e., 2-aminoethanol), Tris (i.e., 2-amino-2-hydroxymethyl-propane-1,3-diol), ethylenediamine, triethylenediamine, or aniline. In certain embodiments, the basic compound is a secondary amine. In certain embodiments, the basic compound is dimethylamine, diethylamine, di-n-propylamine, diisopropylamine, ethylisopropylamine, dicyclohexylamine, methylethanolamine, pyrrolidine, piperidine, morpholine, piperazine, or 1,4-bis-(3-aminopropyl) piperazine. In certain embodiments, the basic compound is a tertiary amine. In certain embodiments, the basic compound is trimethylamine, triethylamine, diisopropylethylamine (DIPEA), tri-n-butylamine, 4-dimethylaminopyridine (DMAP), 1,8-diazabicyclo[5.4.0]undec-7-ene (DBU), pyridine, or 2,6-lutidine.

The suitable conditions in the step of deprotecting a compound of Formula (II-2-A) or (II-2-B), or a salt or stereoisomer thereof, may be reductive conditions. In certain embodiments, the deprotection step comprises reacting an reductive compound with the compound of Formula (II-2-A) or (II-2-B), or a salt or stereoisomer thereof, to remove the protecting group. In certain embodiments, the suitable conditions in the deprotection step comprise use of a reductive compound. In certain embodiments, the reductive compound is a mixture of zinc and HCl. In certain embodiments, the reductive compound is LiAlH$_4$. In certain embodiments, the reductive compound is a mixture of rhodium and hydrogen. In certain embodiments, the reductive compound is a mixture of sodium and ammonia.

The suitable conditions in the step of deprotecting a compound of Formula (II-2-B), or a salt or stereoisomer thereof, may be oxidative conditions. In certain embodiments, the deprotection step comprises reacting an oxidative compound with the compound of Formula (II-2-B), or a salt or stereoisomer thereof, to remove the protecting group. In certain embodiments, the oxidative compound is a mixture of CrO$_3$ and pyridine.

In certain embodiments, the compound of Formula (II-3) is of Formula (II-4):

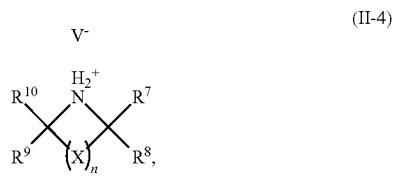

(II-4)

or a stereoisomer thereof, wherein V is an anionic counterion. All anionic counterions described herein are contemplated as being within the scope of the invention. In certain embodiments, the anionic counterion is F$^-$, Cl$^-$, Br$^-$, or I$^-$. In certain embodiments, the anionic counterion is ClO$_4^-$. In certain embodiments, the anionic counterion is NO$_3^-$. In certain embodiments, the anionic counterion is HSO$_4^-$. In certain embodiments, the anionic counterion is H$_2$PO$_4^-$. In certain embodiments, the anionic counterion is a sulfonate ion. In certain embodiments, the anionic counterion is a methansulfonate, trifluoromethanesulfonate, p-toluenesulfonate, or benzenesulfonate ion. In certain embodiments, the anionic counterion is BF$_4^-$.

A compound of Formula (II-4), or a stereoisomer thereof, may be further reacted by contacting with a base to provide a compound of Formula (II-3), or a stereoisomer thereof. In certain embodiments, the base is an inorganic base. In certain embodiments, the inorganic base is ammonia. In certain embodiments, the inorganic base is ammonium carbonate. In certain embodiments, the inorganic base is ammonium hydroxide. In certain embodiments, the inorganic base is an alkali metal carbonate. In certain embodiments, the inorganic base is Li$_2$CO$_3$, Na$_2$CO$_3$, K$_2$CO$_3$, Rb$_2$CO$_3$, or Cs$_2$CO$_3$. In certain embodiments, the inorganic base is an alkali metal bicarbonate. In certain embodiments, the inorganic base is LiHCO$_3$, NaHCO$_3$, KHCO$_3$, RbHCO$_3$, or CsHCO$_3$. In certain embodiments, the inorganic base is an alkali metal hydroxide. In certain embodiments, the inorganic base is LiOH, NaOH, KOH, RbOH, or CsOH. In certain embodiments, the inorganic base is an alkaline earth metal carbonate. In certain embodiments, the inorganic base is BeCO$_3$, MgCO$_3$, CaCO$_3$, SrCO$_3$, or BaCO$_3$. In certain embodiments, the inorganic base is an alkaline earth metal bicarbonate. In certain embodiments, the inorganic base is Be(HCO$_3$)$_2$, Mg(HCO$_3$)$_2$, Ca(HCO$_3$)$_2$, Sr(HCO$_3$)$_2$, or Ba(HCO$_3$)$_2$. In certain embodiments, the inorganic base is an alkaline earth metal hydroxide. In certain embodiments, the inorganic base is Be(OH)$_2$, Mg(OH)$_2$, Ca(OH)$_2$, Sr(OH)$_2$, or Ba(OH)$_2$. In certain embodiments, the base is an organic base. In certain embodiments, the organic base is an aliphatic amine. In certain embodiments, the organic base is an aromatic amine. In certain embodiments, the organic base is a primary amine. In certain embodiments, the organic base is a secondary amine. In certain embodiments, the organic base is a tertiary amine. In certain embodiments, the organic base is triethylamine, DIPEA, or DBU. In certain embodiments, the organic base is substituted pyridine. In certain embodiments, the organic base is 2,6-lutidine or DMAP. In certain embodiments, the organic base is unsubstituted pyridine.

A compound of Formula (II-3), or a stereoisomer thereof, may be further reacted with an acid to provide a salt of compound of Formula (II-3), or a stereoisomer thereof. The acid is as described herein.

The cyclic secondary amines may be synthesized under any suitable conditions described herein.

The compounds synthesized by the inventive methods may be screened for a wide range of biological activities, e.g., for anti-proliferative, anti-microbial, anti-arrhythmic, anti-hypertensive, anti-neurodegenerative, and/or anti-diabetic activities. The compounds prepared by the inventive methods, or salts or stereoisomers thereof, may be administered to a subject to treat and/or prevent a disease (e.g., a proliferative disease, infectious disease, inflammatory disease, autoimmune disease, cardiovascular disease, gastrointestinal disease, neurodegenerative disease, or metabolic disease) in the subject.

EXAMPLES

In order that the invention described herein may be more fully understood, the following examples are set forth. These examples are for illustrative purposes only and are not to be construed as limiting this invention in any manner.
Preparation of the Iron-Based Catalysts The iron-based catalysts described herein that are useful in the inventive methods (e.g., a ferrous compound of Formula (B) or (G), or a salt thereof, such as compounds 3A and 3B) may be synthesized according to reported processes, such as ones described in King et al., *J. Am. Chem. Soc.* 133, 4917 (2011), which is incorporated herein by reference.
Preparation of Acyclic Secondary Amines Acyclic secondary amines (e.g., compounds 25A-25D) may be synthesized according to the general method shown in Scheme 4 through a reaction of an azide (e.g., R$^A$N$_3$) with an substituted or unsubstituted, branched or unbranched, cyclic or acyclic olefin (e.g., compounds 26A-26C) catalyzed by a compound of Formula (B) or (G) (e.g., compound 3, 3A, or 3B). Any suitable conditions may be employed. For example, compounds 25A-25D may be prepared at about 25° C., about 60° C., about 100° C., or about 120° C. for about 6 hours, about 12 hours, or about 24 hours, using benzene as the solvent or no solvent (i.e., neat). When 1 equiv. of R$^4$N$_3$ and 1 or more equiv. of the olefin are used, the loading of compound 3 may be about 10% (i.e., 0.1 equiv.) or about 20% (i.e., 0.2 equiv.). The reactions may be conducted under an atmosphere of nitrogen or argon. Compounds 25A-25D may be purified and characterized using methods known in the art (e.g., flash chromatography).

tion. Volatiles were removed under reduced pressure to yield the acyclic secondary amine product. The yields were determined by $^1$H NMR via integration against ferrocene, averaging over three runs for each substrate.

Alternatively, the following procedure may be used to make acyclic secondary amines, especially, allylic acyclic secondary amines. Under an inert N$_2$ atmosphere, 1-azidoadamantane (30.5 mg, 0.14 mmol, 5 equiv., or 60.9 mg, 0.28 mmol, 10 equiv.) was added to a stirring solution of compound 3B (20 mg, 0.028 mmol, 1 equiv.) in 2 mL of an olefin

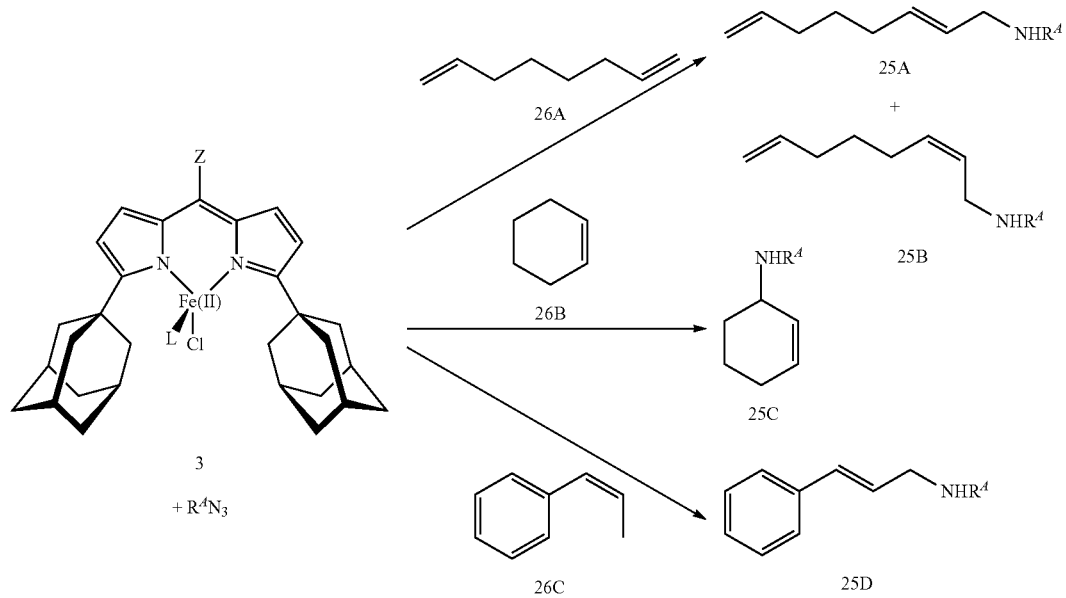

Scheme 4.

For example, a wide range of acyclic secondary amines may be prepared by a method similar to the following procedure. Under an inert N$_2$ atmosphere, 1-azidoadamantane (60.9 mg, 0.28 mmol, 10 equiv.) was added to a stirring solution of compound 3B (20 mg, 0.028 mmol, 1 equiv.) in 1 mL of an olefin (e.g., styrene) in a 20 mL scintillation vial. The resultant inky, dark red solution was stirred for 12 hours at 25° C. The mixture was purified by flash chromatography using a short pipette of triethylamine-treated silica gel eluted with 10:1 hexanes:EtOAc to yield a brightly colored soluin a 20 mL scintillation vial. The resultant inky, dark red solution was stirred for 12 hours at the indicated temperature. The mixture was concentrated and purified by flash chromatography eluted with 9:1 DCM:methanol to yield a yellow solution. Volatiles were removed under reduced pressure to yield the allylic amine product. The yields were determined by $^1$H NMR via integration against ferrocene.

Yields of exemplary acyclic secondary amines synthesized using the inventive methods are shown in Table 5.

TABLE 5

Synthesis of acyclic amines 25.

R—CH=CH$_2$ →(AdN$_3$, 3B, neat)→ R—CH=CH—NHAd

26 → 25

| 26 | 3B Loading (mol %) | Temperature (° C.) | 25 | Yield | E/Z ratio |
|---|---|---|---|---|---|
| indene | 10 | 100 | indene-NHAd | 49 | |

TABLE 5-continued

Synthesis of acyclic amines 25.

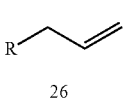

| 26 | 3B Loading (mol %) | Temperature (° C.) | 25 | Yield | E/Z ratio |
|---|---|---|---|---|---|
| 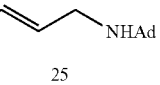 | 20<br>20<br>10 | 25<br>60<br>100 | 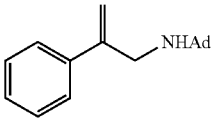 | 35<br>51<br>53 | |
| 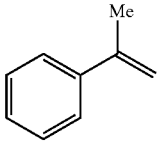 | 20<br>10 | 25<br>100 | 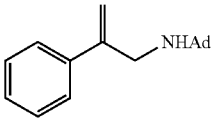 | 26<br>38 | Only E isomer observed |
|  | 20<br>10 | 25<br>100 | 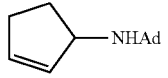 | 12<br>29 | |
|  | 20<br>20<br>10 | 25<br>60<br>100 | 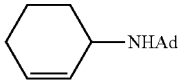 | 10<br>38<br>39 | |
| 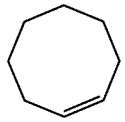 | 10 | 100 | 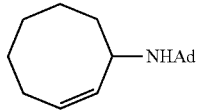 | 14 | |
|  | 10 | 100 | 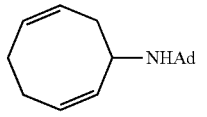 | 17 | |
|  | 20<br>20<br>10<br>10 | 25<br>60<br>100<br>120 |  | 23<br>50<br>48<br>25 | 5:1 E:Z<br>6:1 E:Z<br>6:1 E:Z<br>3:1 E:Z |
| 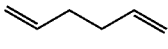 | 20<br>10 | 60<br>100 |  | 68<br>49 | 7:1 E:Z<br>5:1 E:Z |
| 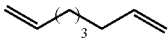 | 20<br>10 | 60<br>100 |  | 71<br>57 | 5:1 E:Z<br>4:1 E:Z |
| 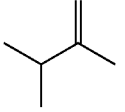 | 10 | 60 | 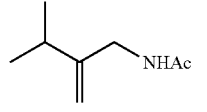 | 17 | |

Preparation of Protected Cyclic Secondary Amines

Boc- or Fmoc-protected cyclic secondary amines may be synthesized according to the general method shown in Scheme 5.

Scheme 5.

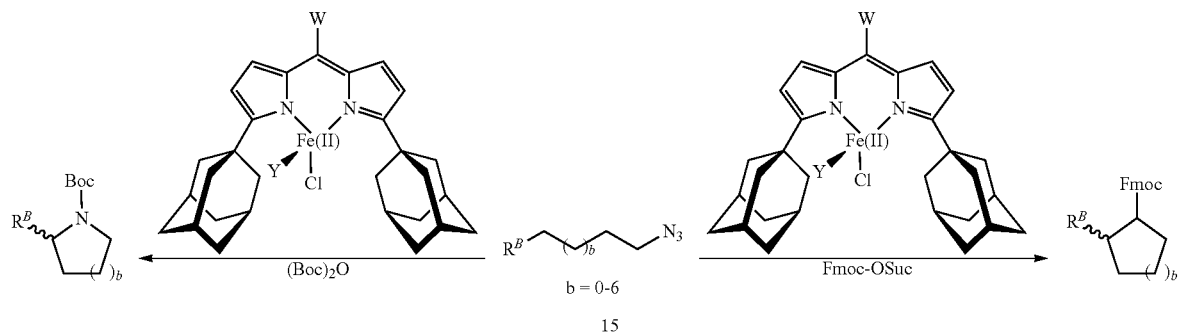

For example, a variety of substituted aliphatic azides (e.g., 1-azido-5-hexene) were subjected to compound 3A. Exposure of 1-azido-5-hexene to compound 3A at room temperature in benzene quickly consumed the azide, as ascertained by the disappearance of the azide stretch in the IR spectrum and afforded a new paramagnetically shifted $^1$H NMR spectrum. Crystallization was induced by slow diffusion of a hexanes solution of the product at 23° C. to yield crystals in which 2-vinylpyrrolidine was bound to the iron-based complex to give compound 8 (Scheme 6 and FIG. 5A). Similarly, treatment of 1-azido-4-phenylbutane with 3A afforded the cyclized product 2-phenylpyrrolidine as an iron-bound adduct 9 (FIG. 5B). In addition to allylic and benzylic C—H bonds, less reactive tertiary C—H bonds could similarly be functionalized. The reaction of 1-azido-5-methylpentane and 3A under standard conditions gave the 2,2-dimethylpyrrolidine iron-bound product. Gratifyingly, even secondary aliphatic C—H bonds could be functionalized through this method. Addition of 1-azidohexane to 3A resulted in the rapid consumption of the azide to afford a single product, which was determined to be the 2-ethylpyrrolidine complex 10 (FIG. 5C). In an attempt to activate the primary C—H bond of an aliphatic azide substrate, 1-azidobutane was exposed to 3A. However, the only products observed in this transformation were linear n-butylamine and n-butylimine. To eliminate the potential for imine formation, through a process involving intermolecular C—H bond activation or β-hydride elimination, the gem-dimethyl substrate 2-azido-2-methylpentane was prepared and subjected to 3A at room temperature for 6 h to afford the cyclized 2,2-dimethylpyrrolidine complex 11 (FIG. 5D) in quantitative yield. The presence of the two α-Me substituents may facilitate the C—H bond functionalization/cyclization process through the Thorpe-Ingold effect (Beesley et al., *J. Chem. Soc., Trans.*, 107, 1080 (1915)).

-continued

9

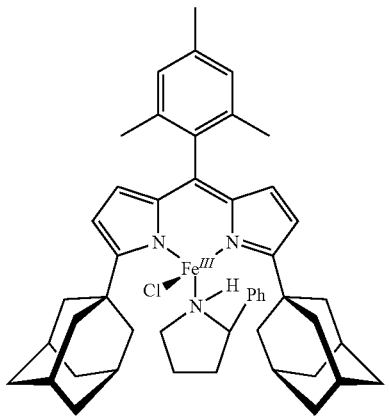

10

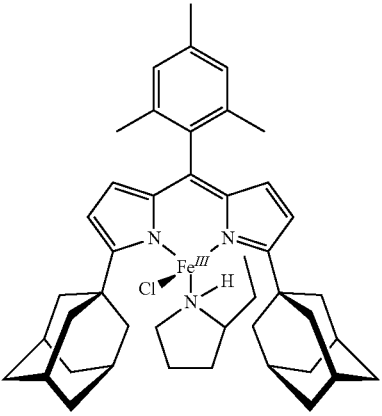

8

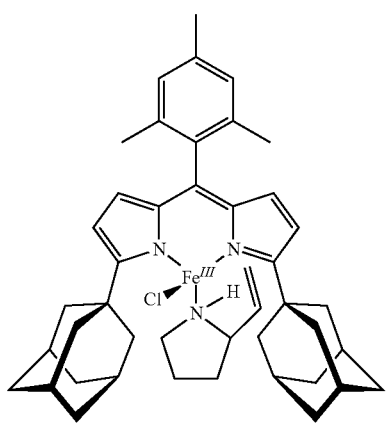

11

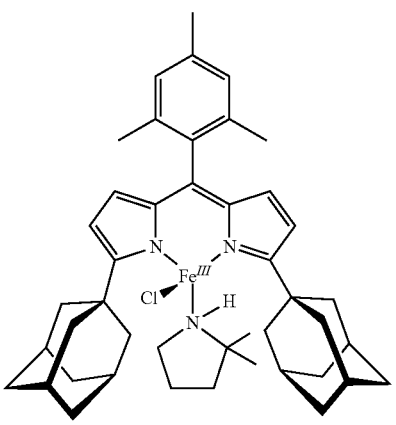

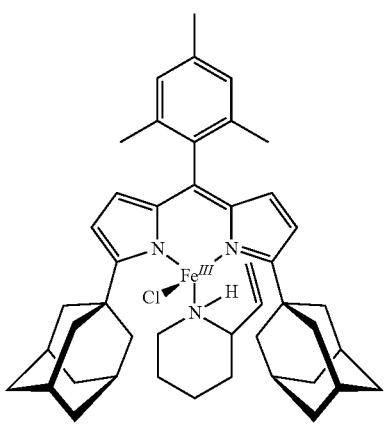

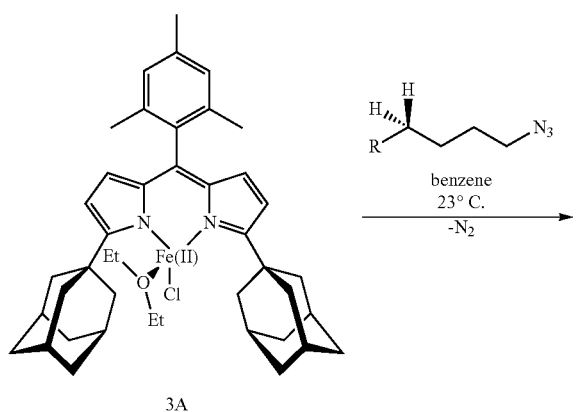

Scheme 6.

3A

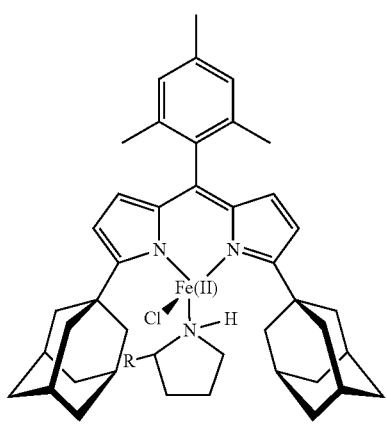

R = C₂H₃, Ph, Et

With a reliable protocol for the stoichiometric C—H functionalization/cyclization of aliphatic azides in hand, attempts to render the reaction catalytic were undertaken (5-10 equiv. of azide per 1 equiv. of compound 3A or 3B). Unfortunately, examination of the cyclization reaction under catalytic conditions did not markedly increase the yield of the resultant free heterocyclic product. The lack of catalyst turnover may be attributed to product inhibition, in which a tight Lewis-acid/base pair between the dipyrromethene-iron and the heterocyclic nitrogen atom is formed. This hypothesis is supported by the ease with which crystals of the corresponding dipyrromethene-iron complexes were obtained (FIGS. 4 and 5).

To overcome this problem, the cyclization reaction was performed in the presence of an in situ protection reagent, which would reduce the nucleophilicity of the product cyclic amines while avoiding the generation of byproducts that might retard or prevent catalysis. Accordingly, treatment of a solution of 1-azido-4-phenylbutane and 9-fluorenylmethyl N-succinimidyl carbonate (Fmoc-OSuc) in benzene at room temperature with a stoichiometric amount of compound 3A for 12 h afforded the Fmoc-protected 2-phenylpyrrolidine in 98% yield. Similarly, addition of an equivalent of compound 3A to a solution of 1-azido-4-phenylbutane and di-t-butyl dicarbonate (Boc₂O) under similar reaction conditions afforded the 1-butyloxycarbonyl (Boc) protected product 1-Boc-2-phenylpyrrolidine in 93% yield. As catalyst loading was decreased, it was discovered that the N-hydroxysuccinimide byproduct of Fmoc-protection led to catalyst decomposition through ligand protonation and limited the reaction to a single turnover. Fortunately, the byproducts of protection with Boc₂O (i.e., t-BuOH and CO₂) did not inhibit catalyst turnover, permitting the cyclic amines to be synthesized with catalytic amounts of compound 3B (chosen to eliminate benzylic C—H bonds from catalyst meso-aryl substituent).

Application of catalytic quantities of compound 3B to the established in situ protection protocol for C—H functionalization/cyclization was investigated (Table 2). Exposure of azides 13 containing allylic, benzylic, or tertiary C—H bonds to compound 3B (10 mol %) provided the corresponding Boc-protected pyrrolidine 14 in good yield (57-64%, entries 1-3). Next, catalytic functionalization of a secondary C—H bond was also possible, affording 1-Boc-2-ethylpyrrolidine in modest yield (27%, entry 4). Even, a primary C—H bond in 2-azido-2-methylpentane could be functionalized to give 1-Boc-2,2-dimethylpyrrolidine in 17% yield (entry 6). The substrate scope was then expanded to include hetero-atom containing functional groups. Exposure of ethyl-5-azidopentanoate to compound 3B under standard catalytic conditions only resulted in linear primary amine and imine products (entry 7). Again, blocking the α-position of the azide 13 with gem-dimethyl substituents led to productive cyclization (entry 8). Introduction of heteroatoms between the reactive functionalities allowed for the formation of 1-Boc-2-phenyloxazolidine in 47% yield (entry 9).

TABLE 2

Amination reactions of azides 13 catalyzed by compound 3B yielding pyrrolidines 14.

| Entry | 13 | 14 | Yield (%)[a] |
|---|---|---|---|
| 1 | | | 64 |
| 2 | | | 57 |
| 3 | | | 60 |
| 4 | | | 27 |
| 5 | | | 0 |
| 6 | | | 17 (7)[b] |
| 7 | | | 0 |
| 8 | | | 11[b] |
| 9 | | | 47[b] |

[a] Yield determined by $^1$H NMR using ferrocene or trimethoxybenzene as the internal standard.
[b] 20 mol% loading of compound 3B.

Figure 6:
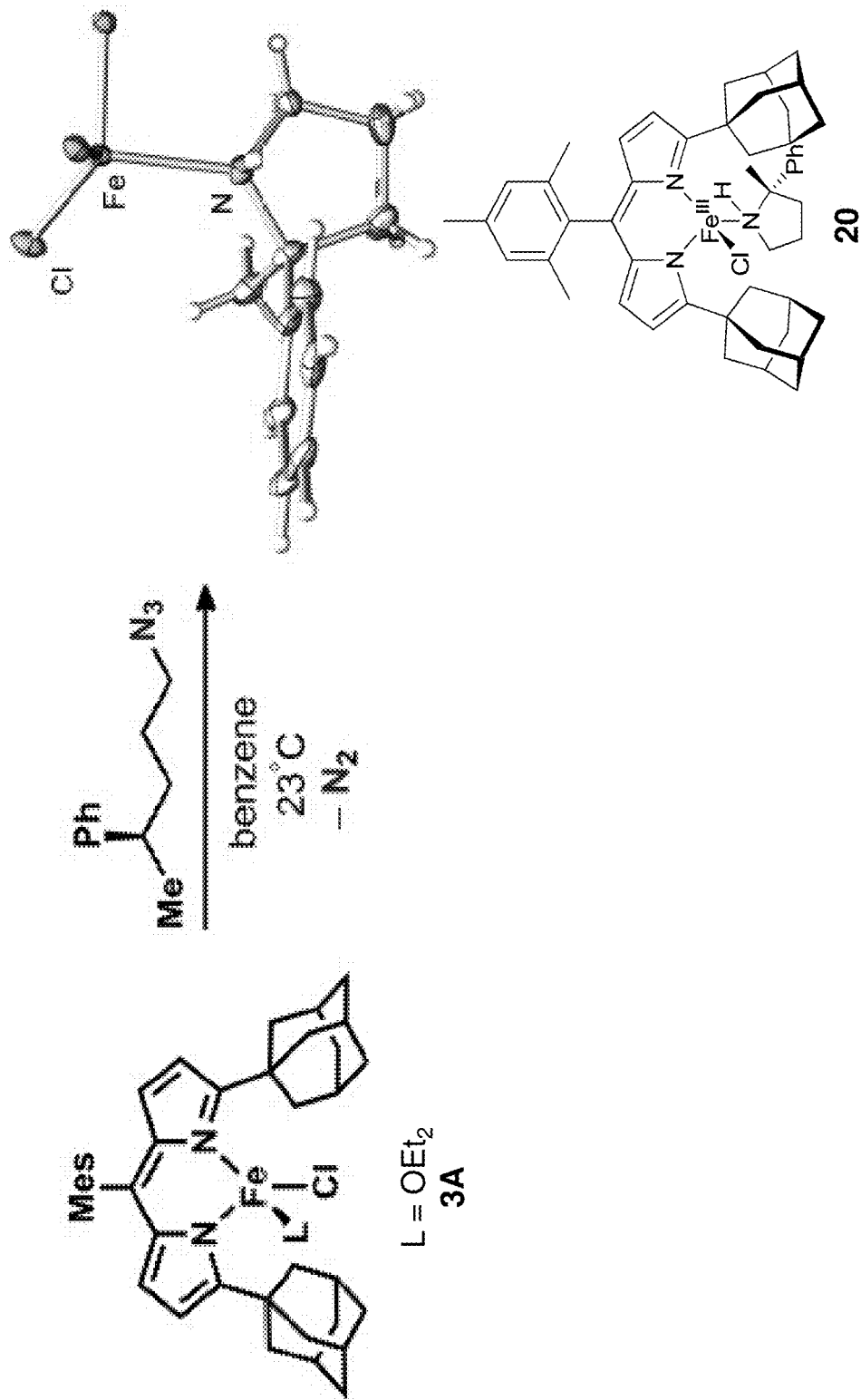
FIG. 6 shows a X-ray crystal structure of (S)-2-methyl-2-phenylpyrrolidine iron-bound adduct 20 obtained from a reaction of (R)-2-phenyl-5-azidopentane (95% enantiomeric excess (ee)) with stoichiometric quantities of compound 3A.

The scope of C—H functionalization/cyclization was further explored in substrates accessible via cuprate-assisted epoxide opening (Drouin et al., *Tetrahedron* 36, 1195 (1980)) followed by azide formation (Table 3). The use of epoxides 15 and alkyl halides (which may be transformed into Grignard reagents 16) permits virtually any substitution pattern to be programmed into the ensuing heterocyclic product. After Li$_2$[CuCl$_4$] promoted epoxide opening, the resultant primary or secondary alcohols were tosylated and displaced with sodium azide to provide the desired cyclization precursor 17. Alternatively, tertiary and benzylic alcohols were directly converted to the corresponding azide (e.g., compound 18) by exposure to trimethylsilylazide and boron trifluoride diethyl etherate (Mukaiyama et al., *Heterocycles* 80, 63 (2010)). Allylic, tertiary and secondary C—H bond substrates available through either reaction sequence underwent facile C—H functionalization/cyclization to give protected (e.g., protected with Boc) cyclic amines 19 (entries 1-9, 58-98% yield). Notably, this method provides access to an all-carbon spiro-center (entry 7, 67%). Functionalization of primary C—H bonds may require a higher loading of the catalyst (e.g., compound 3A or 3B) than a catalytic amount (entry 10). For example, a stoichiometric reaction similar to the reaction in Table 3, entry 10, except that Fmoc-OSuc was used instead of $Boc_2O$ and that 1 equiv. of compound 3B was employed, gave rise to in 78% yield. Interestingly, use of (R)-2-phenyl-5-azidopentane (95% enantiomeric excess (ee)) in the catalytic transformation resulted in (S)-2-methyl-2-phenylpyrrolidine with retention of configuration (entry 5, 75%, 93% ee). A similar reaction using stoichiometric quantities of compound 3A gave the corresponding (S)-2-methyl-2-phenylpyrrolidine iron-bound adduct 20 whose absolute stereochemistry was verified by X-ray diffraction (FIG. 6).

TABLE 3

Synthesis of 1,2,3,4-substituted pyrrolidines 19.

| Entry | 15 | 16 | 17 or 18 | 19[a] | Yield (%)[b] | dr[c] |
|---|---|---|---|---|---|---|
| 1 | styrene oxide (±) | CH₂=CHCH₂CH₂MgBr | CH₂=CHCH₂CH₂CH(Ph)N₃ | 2-vinyl-5-phenyl-N-Boc-pyrrolidine | 60 | 3.9:1 |
| 2 | | CH₂=CHCH₂CH₂MgBr | PhCH(CH₂N₃)CH₂CH₂CH=CH₂ | 2-vinyl-4-phenyl-N-Boc-pyrrolidine | 66 | 1.5:1 |
| 3 | | Me₂CHCH₂MgBr | Me₂CHCH₂CH₂CH(Ph)N₃ | 2,2-dimethyl-5-phenyl-N-Boc-pyrrolidine | 70 | |

TABLE 3-continued
Synthesis of 1,2,3,4-substituted pyrrolidines 19.
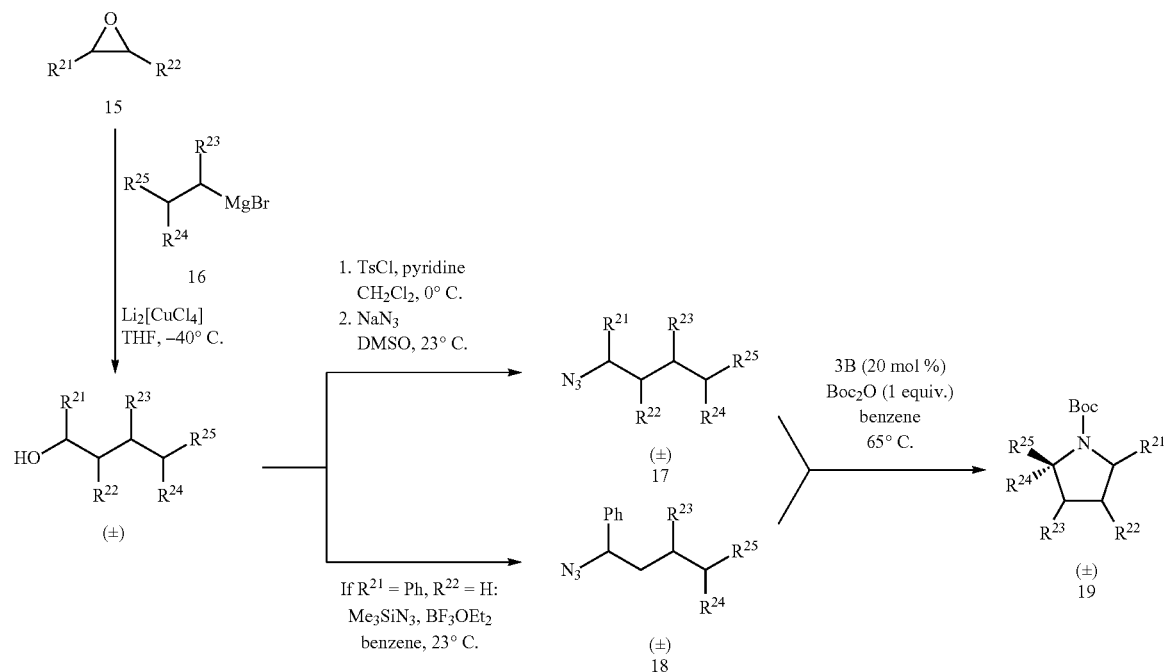
| Entry | 15 | 16 | 17 or 18 | 19[a] | Yield (%)[b] | dr[c] |
|---|---|---|---|---|---|---|
| 4 | | | | | 98 | |
| 5 | | | | | 75 | |
| 6 | | | | | 84 | 1.1:1 |
| 7 | | | | | 67 | |
| 8 | | | | | 73 | 2.1:1 |

TABLE 3-continued

Synthesis of 1,2,3,4-substituted pyrrolidines 19.

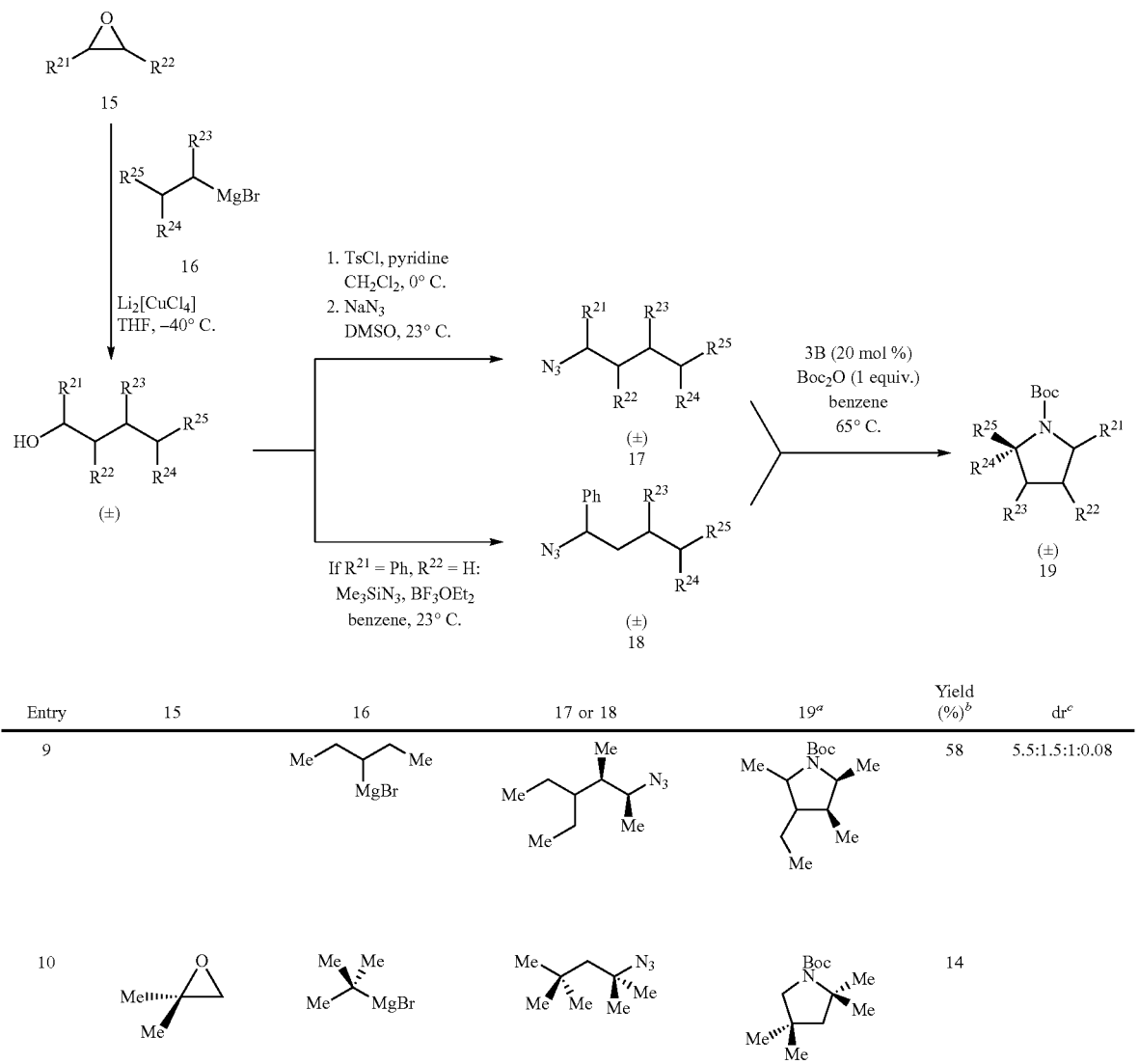

| Entry | 15 | 16 | 17 or 18 | 19[a] | Yield (%)[b] | dr[c] |
|---|---|---|---|---|---|---|
| 9 | | Me-CH(MgBr)-CH(Me)-Me | Me-CH(Me)-CH(CH2Me)-CH(Me)-N3 | Me-pyrrolidine(Boc, Me, Me, CH2Me) | 58 | 5.5:1.5:1:0.08 |
| 10 | Me-epoxide-Me,Me | Me2C(MgBr)-Me | Me2C(N3)-CH2-CMe3 | pyrrolidine(Boc, Me, Me, Me, Me, Me) | 14 | |

[a]Pyrrolidines 19 are racemic unless otherwise noted.
[b]Yields are representative of cyclization reactions only and are determined by $^1$H NMR using ferrocene or trimethoxybenzene as the internal standard.
[c]The term "dr" refers to diastereomeric ratio.

The potential of the inventive methods to generate cyclic amines of various ring sizes was also explored. It was expected that a vinyl directing group could be employed to encourage the site-selective functionalization of the allylic C—H bond within the acyclic precursor. Treatment of 1-azido-6-heptene and Boc$_2$O (1 equiv.) with compound 3B (1 equiv.) at room temperature generated the 6-membered 1-Boc-2-vinylpiperidine (entry 1, Table 4) as the exclusive reaction product. Unfortunately, use of the vinyl activating group to target 7-membered azepane products led to exclusive formation of the corresponding pyrrolidine (entry 4). In contrast, a phenyl activating group was not effective in favoring the formation of a 6-membered ring product. Addition of compound 3B to 1-azido-5-phenyl-pentane under standard conditions resulted in a 1:0.85 mixture of both 1-Boc-2-phenylpiperidine and 1-Boc-2-benzylpyrrolidine (entry 2). Similarly, the use of a tertiary C—H bond to favor 6-membered ring formation in the case of 1-azido-5-methylhexane resulted in a mixture of piperidine and pyrrolidine products (entry 3). An attempt was made to block the potential for pyrrolidine formation; exposure of 2-azido-2, 5,5-trimethylhexane and Fmoc-OSuc to compound 3B resulted in both the anticipated 1-Fmoc-2,2,5,5-tetramethylpiperidine and the unexpected 1-Fmoc-2,2-dimethyl-4-tert-butylazetidine (entry 5). Alternatively, use of compound 3A and omission of Fmoc-OSuc allowed for the characterization of the corresponding iron-bound adducts by X-ray analysis (FIGS. 7B and 7C).

TABLE 4

Synthesis of cyclic amines 24 of various ring sizes.

[Reaction scheme: azide 23 (R₂, H, R₃, R₃ substituents on carbon chain with (CH₂)ₙ and N₃; n = 1, 2, 3) → with 3B (1 equiv), Boc₂O (1 equiv), benzene, 23° C., 12 h → cyclic amine product 24 (N-Boc ring with R₁, R₂, R₃ substituents)]

| Entry | Azide 23 | Product(s) 24 | Conv. (%)[a,b] |
|---|---|---|---|
| 1 | CH₂=CH-(CH₂)₄-N₃ | 2-vinyl-N-Boc-piperidine | 45 |
| 2 | CH₂=CH-(CH₂)₅-N₃ | 2-allyl-N-Boc-pyrrolidine | 82 |
| 3 | Ph-(CH₂)₄-N₃ | 2-Ph-N-Boc-piperidine + 2-Bn-N-Boc-pyrrolidine | 52 (1.0:0.9) |
| 4 | (CH₃)₂CH-(CH₂)₃-N₃ | 2,2-dimethyl-N-Boc-piperidine + 2-iPr-N-Boc-pyrrolidine | 47 (1.0:1.5) |
| 5 | (CH₃)₃C-CH₂-CH(CH₃)-N₃ (with stereochem) | gem-dimethyl N-Boc-piperidine + 2-tBu-N-Boc-azetidine | 47 (1.0:1.5) |

[a]Yields are determined by ¹H NMR using ferrocene or trimethoxybenzene as the internal standard.
[b]Ratios are deteremined by integration of GC/MS peaks.

As illustrated in FIG. 3, it is hypothesize that the C—H bond functionalization/cyclization reaction occurs via a three-step process involving: (1) oxidation of the $Fe^{II}$ catalyst (e.g., compound 3A) to an $Fe^{III}$ imido radical (e.g., compound 4) by the alkyl azide substrate; (2) intramolecular H-atom abstraction to generate an alkyl radical and an $Fe^{III}$ amide (e.g., compound 5) (path Ia); and (3) radical recombination to form the observed cyclic amine product (e.g., compound 6) (path Ib). Alternatively, a direct C—H bond insertion by the $Fe^{III}$ imido radical intermediate cannot be excluded (path II). Both mechanisms require that the substrate C—H bond be brought into close proximity to the reactive Fe-imido radical. Based on previous findings, the imido radical likely resides in the plane defined by the iron and the dipyrrin ligand, flanked by large pyrrolide adamantyl substituents. Such a conformation requires that the C—H bond substrate approach the imido radical opposite the chloride ligand. It is expected that once this orientation is obtained, C—H bond functionalization is rapid. This hypothesis is supported by the retention of stereochemical information during the cyclization of (R)-2-phenyl-5-azidopentane. Additionally, cyclization of 1-azido-4-deutero-4-phenylbutane (Scheme 7) provides an intramolecular kinetic isotope effect (KIE) of 5.3 at 25° C. and 5.1(2) at 65° C. This value is similar to the KIE observed in the hydroxylation of 1,3-dideuteroadamantane catalyzed by tetramesitylporphyrin iron with oxone [$k_H/k_D$=4.1(2)](Sorokin et al., J. Am. Chem. Soc. 115, 7293 (1993)). Finally, addition of the radical clock substrate (2-(4-azidobutyl)cyclopropyl)benzene to compound 3B exclusively furnishes the pyrrolidine product 1-Boc-2-(2-phenylcyclopropyl)pyrrolidine with the cyclopropyl unit intact (Scheme 8). The non-unity intramolecular kinetic isotope effect suggests a stepwise mechanism for benzylic substrates (FIG. 3, Path I (i.e., Ia and Ib)), which is consistent with previously reported intermolecular amination reaction (King et al., J. Am. Chem. Soc. 133, 4917 (2011)). The stereospecificity of the cyclization and the preservation of the cyclopropyl unit in the radical clock experiment suggest that if a stepwise mechanism is operative, the radical intermediate following H-atom abstraction is short-lived [recombination rate>1011 s⁻¹ (Newcomb et al., Acc. Chem. Res. 33, 449 (2000))]. Alternatively, the reaction mechanism may change to a direct insertion mechanism (FIG. 3, path II) when stronger substrate C—H bonds are functionalized.

Scheme 7.

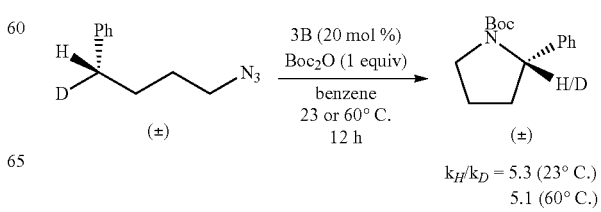

$k_H/k_D$ = 5.3 (23° C.)
5.1 (60° C.)

Scheme 8.

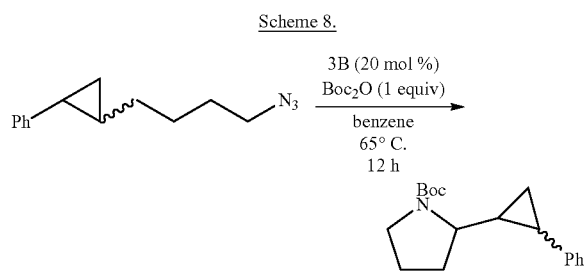

The results described herein have demonstrated the oxidative potency of the transiently formed, high-spin iron imido radical for the functionalization of both activated and unactivated aliphatic C—H bond substrates. This iron-mediated cyclization of linear azides provides facile entry into complex acyclic and cyclic amines from readily available substrates that cannot be achieved by azide photolysis (Barton et al., *J. Chem. Soc.* 2444 (1965)) or via classic Hoffmann-Löffler-Freytag methodologies (Hoffman, *Berichte* 18, 105 (1885)). It is expected that the methods of the invention can be extended to produce a wide variety of acyclic and cyclic amines (e.g., saturated cyclic amines). The oxidative amination of aliphatic C—H bonds over more electron-rich C—H bonds (olefins and aromatics) is made possible by the unique electronic structure of the putative iron-stabilized imido radical intermediate.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of preparing a compound of Formula (II-1):

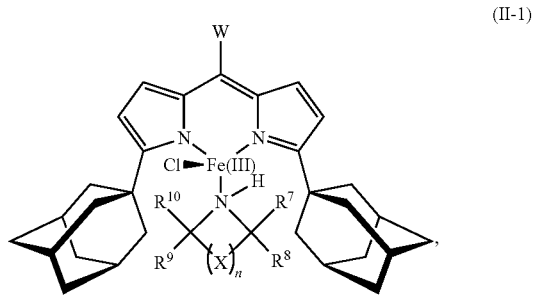

or a salt thereof, the method comprising reacting an azide of Formula (F), or a salt thereof, with a ferrous compound of Formula (G), or a salt thereof:

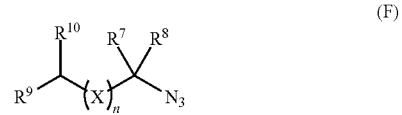

-continued

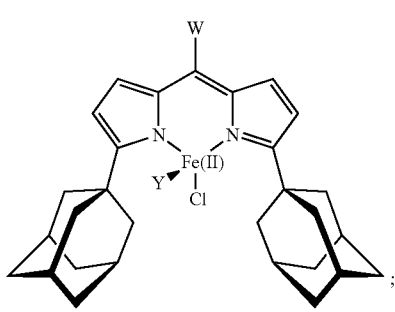

(G)

wherein:
W is selected from the group consisting of mesityl and 2,6-dichlorophenyl;
each occurrence of X is independently selected from the group consisting of —O—, —S—, —NR$^c$—, and —C(R$^d$)$_2$—;
R$^c$ is selected from the group consisting of hydrogen, a nitrogen protecting group, optionally substituted acyl, optionally substituted alkyl, optionally substituted alkenyl, optionally substituted alkynyl, optionally substituted carbocyclyl, optionally substituted heterocyclyl, optionally substituted aryl, and optionally substituted heteroaryl;
each one of R$^7$, R$^8$, R$^9$, and R$^{10}$, and each occurrence of R$^d$, are independently selected from the group consisting of hydrogen, halogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^e$, —N(R$^e$)$_2$, —SR$^e$, —CN, —C(=NR$^e$)R$^e$, —C(=NR$^e$)OR$^e$, —C(=NR$^e$)N(R$^e$)$_2$, —NO$_2$, —NR$^e$C(=O)R$^e$, —NR$^e$C(=O)OR$^e$, —NR$^e$C(=O)N(R$^e$)$_2$, —OC(=O)R$^e$, —OC(=O)OR$^e$, —OC(=O)N(R$^e$)$_2$, and —ON(R$^e$)$_2$;
each occurrence of R$^e$ is independently selected from the group consisting of hydrogen, optionally substituted acyl, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group when attached to a nitrogen atom, an oxygen protecting group when attached to an oxygen atom, and a sulfur protecting group when attached to a sulfur atom, or two R$^e$ groups are joined to form an optionally substituted heterocyclic ring;
or two of R$^7$, R$^8$, R$^9$, R$^{10}$, R$^c$, and R$^d$ groups are joined to form an optionally substituted carbocyclyl or optionally substituted heterocyclic ring;
Y is selected from the group consisting of N(R$^f$)$_3$, R$^f$—O—R$^f$, R$^f$—S—R$^f$, optionally substituted heterocyclyl, and optionally substituted heteroaryl;
each occurrence of R$^f$ is independently selected from the group consisting of optionally substituted alkyl, optionally substituted alkenyl, optionally substituted alkynyl, optionally substituted carbocyclyl, optionally substituted heterocyclyl, optionally substituted aryl, and optionally substituted heteroaryl; and
n is 1, 2, 3, 4, or 5.

2. The method of claim 1, further comprising reacting the compound of Formula (II-1), or a salt thereof, with di-t-butyl dicarbonate (Boc$_2$O) to provide a compound of Formula (II-2-A), or a salt thereof, or with 9-fluorenylmethyl N-succinimidyl carbonate (Fmoc-OSuc) to provide a compound of Formula (II-2-B), or a salt thereof:

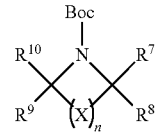

(II-2-A)

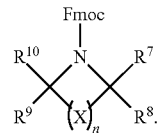

(II-2-B)

3. The method of claim 2, further comprising deprotecting the compound of Formula (II-2-A) or (II-2-B), or a salt thereof, to provide a cyclic amine of Formula (II-3):

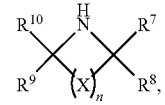

(II-3)

or a salt thereof.

4. The method of claim 3, wherein the deprotection step comprises reacting an acidic compound, a nucleophilic compound, or a reductive compound with the compound of Formula (II-2-A), or a salt thereof, or reacting a nucleophilic compound, a basic compound, a reductive compound, or an oxidative compound with the compound of Formula (II-2-B), or a salt thereof, to provide the cyclic amine of Formula (II-3), or a salt thereof.

5. The method of claim 1, wherein R$^7$ and R$^8$ are each hydrogen.

6. The method of claim 1, wherein R$^7$ is hydrogen; and R$^8$ is optionally substituted alkyl.

7. The method of claim 1, wherein R$^7$ and R$^8$ are each optionally substituted alkyl.

8. The method of claim 1, wherein Y is R$^f$—O—R$^f$; and each occurrence of R$^f$ is independently optionally substituted alkyl.

9. The method of claim 1, wherein Y is optionally substituted heterocyclyl.

10. The method of claim 1, wherein Y is optionally substituted tetrahydrofuran or optionally substituted tetrahydropyran.

11. The method of claim 1, wherein Y is optionally substituted heteroaryl.

12. The method of claim 1, wherein Y is optionally substituted pyridine.

13. The method of claim 1, wherein n is 2.

14. The method of claim 1, wherein n is 3.

15. The method of claim 1, wherein n is 4.

16. The method of claim 1, wherein W is mesityl.

17. The method of claim 1, wherein W is 2,6-dichlorophenyl.

18. The method of claim 1, wherein Y is diethyl ether.

19. The method of claim 1, wherein the ferrous compound of Formula (G) is of Formula (3A):
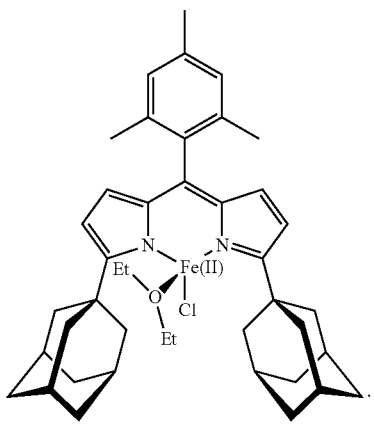
(3A)
20. The method of claim 1, wherein the ferrous compound of Formula (G) is of Formula (3B):
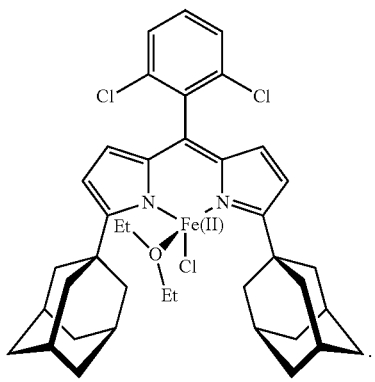
(3B)
* * * * *